(12) United States Patent
Shen

(10) Patent No.: US 9,499,862 B2
(45) Date of Patent: *Nov. 22, 2016

(54) PHOSPHOLINKED DYE ANALOGS WITH AN AMINO ACID LINKER

(71) Applicant: Pacific Biosciences of California, Inc., Menlo Park, CA (US)

(72) Inventor: Gene Shen, Santa Clara, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/667,869

(22) Filed: Mar. 25, 2015

(65) Prior Publication Data

US 2015/0197794 A1    Jul. 16, 2015

Related U.S. Application Data

(63) Continuation of application No. 13/218,436, filed on Aug. 25, 2011, now Pat. No. 8,993,737.

(60) Provisional application No. 61/377,004, filed on Aug. 25, 2010, provisional application No. 61/377,022, filed on Aug. 25, 2010, provisional application No. 61/377,031, filed on Aug. 25, 2010, provisional application No. 61/377,038, filed on Aug. 25, 2010, provisional application No. 61/377,048, filed on Aug. 25, 2010.

(51) Int. Cl.
| | | |
|---|---|---|
| *C07H 17/00* | (2006.01) |
| *C12Q 1/68* | (2006.01) |
| *C07K 9/00* | (2006.01) |
| *C09B 23/10* | (2006.01) |
| *C07D 209/14* | (2006.01) |
| *C07D 401/14* | (2006.01) |
| *C07D 405/14* | (2006.01) |
| *G01N 33/58* | (2006.01) |
| *C09B 23/01* | (2006.01) |
| *C09B 23/06* | (2006.01) |
| *C09B 23/08* | (2006.01) |
| *C07H 19/10* | (2006.01) |
| *C07K 5/09* | (2006.01) |
| *C07K 5/11* | (2006.01) |

(52) U.S. Cl.
CPC ........... *C12Q 1/6869* (2013.01); *C07D 209/14* (2013.01); *C07D 401/14* (2013.01); *C07D 405/14* (2013.01); *C07H 19/10* (2013.01); *C07K 5/0815* (2013.01); *C07K 5/1019* (2013.01); *C09B 23/0025* (2013.01); *C09B 23/0033* (2013.01); *C09B 23/0066* (2013.01); *C09B 23/06* (2013.01); *C09B 23/083* (2013.01); *C09B 23/105* (2013.01); *C12Q 1/6844* (2013.01); *C12Q 1/6876* (2013.01); *G01N 33/582* (2013.01)

(58) Field of Classification Search
CPC .................................................... C12Q 1/6869
USPC ........................... 536/4.1; 530/322; 435/6.11
See application file for complete search history.

(56) References Cited

U.S. PATENT DOCUMENTS

| | | | |
|---|---|---|---|
| 4,711,955 | A | 12/1987 | Ward et al. |
| 5,106,990 | A | 4/1992 | Ohno et al. |
| 5,332,567 | A | 7/1994 | Goldenberg |
| 5,627,027 | A | 5/1997 | Waggoner |
| 5,688,648 | A | 11/1997 | Mathies et al. |
| 5,808,044 | A | 9/1998 | Brush et al. |
| 5,986,086 | A | 11/1999 | Brush et al. |
| 6,114,350 | A | 9/2000 | Randall et al. |
| 6,197,956 | B1 | 3/2001 | Randall et al. |
| 6,224,644 | B1 | 5/2001 | Randall et al. |
| 6,255,083 | B1 | 7/2001 | Williams |
| 6,265,193 | B1 | 7/2001 | Brandis et al. |
| 6,331,632 | B1 | 12/2001 | Reedy et al. |
| 6,399,335 | B1 | 6/2002 | Kao et al. |
| 6,437,141 | B2 | 8/2002 | Randall et al. |
| 6,544,797 | B1 | 4/2003 | Buechler et al. |
| 6,917,726 | B2 | 7/2005 | Levene et al. |
| 7,013,054 | B2 | 3/2006 | Levene et al. |
| 7,033,764 | B2 | 4/2006 | Korlach et al. |

(Continued)

FOREIGN PATENT DOCUMENTS

| | | |
|---|---|---|
| EP | 1627635 A2 | 2/2006 |
| JP | 03-233444 A | 10/1991 |

(Continued)

OTHER PUBLICATIONS

Abu El-Hamd, R.M., et al., "Some New Fused Heterocyclic Cyanine Dyes with Ring Junction Heteroatom," Chem. Papers, vol. 51, No. 2, p. 117-127 (1997).

Akeson, M. et al., "Microsecond time-scale discrimination among polycytidylic acid, polyadenylic acid, and polyuridylic acid as homopolymers or as segments within single RNA molecules," Biophys. J., 77:3227-3233 (1999).

Braslavsky, I. et al., "Sequence information can be obtained from single DNA molecules," Proc. Natl. Acad. Sci. USA, 100:3960-3964 (2003).

Chudinov, A.V. et al., Document No. 149:493676, retrieved from CAPLUS, Oct. 24, 2008.

(Continued)

*Primary Examiner* — Jezia Riley
(74) *Attorney, Agent, or Firm* — Morgan, Lewis & Bockius LLP

(57) ABSTRACT

In various embodiments, the present invention provides fluorescent dyes that are linked to another species through an amino acid or peptide linker. In an exemplary embodiment, the dye is linked to a polyphosphate nucleic acid through an amino acid or peptide linker. These conjugates find use in single molecule DNA sequencing and other applications. In various embodiments, the dye moiety is a cyanine dye. Cyanine dyes that are highly charged, such as those including multiple sulfonate, alkylsulfonate, carboxylate and/or alkylcarboxylate moieties are examples of cyanine dyes of use in the compounds of the invention.

22 Claims, 29 Drawing Sheets

(56) References Cited

U.S. PATENT DOCUMENTS

| | | | |
|---|---|---|---|
| 7,041,812 B2 | 5/2006 | Kumar et al. | |
| 7,052,839 B2 | 5/2006 | Nelson et al. | |
| 7,052,847 B2 | 5/2006 | Korlach et al. | |
| 7,056,661 B2 | 6/2006 | Korlach et al. | |
| 7,056,676 B2 | 6/2006 | Korlach et al. | |
| 7,170,050 B2 | 1/2007 | Turner et al. | |
| 7,181,122 B1 | 2/2007 | Levene et al. | |
| 7,223,541 B2 | 5/2007 | Fuller et al. | |
| 7,292,742 B2 | 11/2007 | Levene et al. | |
| 7,302,146 B2 | 11/2007 | Turner et al. | |
| 7,393,640 B2 | 7/2008 | Kumar et al. | |
| 7,405,281 B2 | 7/2008 | Xu et al. | |
| 7,777,013 B2 | 8/2010 | Xu | |
| 7,968,702 B2 | 6/2011 | Wegener et al. | |
| 7,973,146 B2 | 7/2011 | Shen | |
| 8,058,031 B2 | 11/2011 | Xu | |
| 8,133,702 B2 | 3/2012 | Shen | |
| 8,148,516 B2 | 4/2012 | Williams et al. | |
| 8,889,886 B2 | 11/2014 | Yue et al. | |
| 8,993,737 B2* | 3/2015 | Shen | C07D 401/14 435/6.11 |
| 9,315,864 B2 | 4/2016 | Yue | |
| 2002/0156288 A1 | 10/2002 | Caputo et al. | |
| 2003/0124576 A1 | 7/2003 | Kumar et al. | |
| 2003/0190564 A1 | 10/2003 | Hioki et al. | |
| 2004/0023413 A1 | 2/2004 | Opalsky | |
| 2005/0170367 A1 | 8/2005 | Quake et al. | |
| 2005/0244863 A1 | 11/2005 | Mir | |
| 2006/0240439 A1 | 10/2006 | Smith et al. | |
| 2006/0281109 A1 | 12/2006 | Ost et al. | |
| 2007/0036511 A1 | 2/2007 | Lundquist et al. | |
| 2007/0072196 A1 | 3/2007 | Xu et al. | |
| 2007/0099212 A1 | 5/2007 | Harris | |
| 2007/0104649 A1 | 5/2007 | Fischer et al. | |
| 2007/0161017 A1 | 7/2007 | Eid et al. | |
| 2007/0196846 A1 | 8/2007 | Hanzel et al. | |
| 2008/0267883 A1 | 10/2008 | Rajopadhye et al. | |
| 2008/0277595 A1 | 11/2008 | Lundquist et al. | |
| 2009/0208957 A1 | 8/2009 | Korlach | |
| 2009/0233302 A1 | 9/2009 | Wegener et al. | |
| 2009/0269759 A1 | 10/2009 | Menchen et al. | |
| 2009/0275036 A1 | 11/2009 | Hardin et al. | |
| 2009/0325260 A1 | 12/2009 | Otto | |
| 2010/0152424 A1 | 6/2010 | Korlach | |
| 2010/0255488 A1 | 10/2010 | Kong | |
| 2010/0323389 A1 | 12/2010 | Xu | |
| 2011/0313129 A1 | 12/2011 | Hu et al. | |
| 2012/0052506 A1 | 3/2012 | Yue | |
| 2012/0052507 A1 | 3/2012 | Shen | |
| 2012/0058469 A1 | 3/2012 | Shen | |
| 2012/0058473 A1 | 3/2012 | Yue | |
| 2012/0058482 A1 | 3/2012 | Shen | |
| 2012/0077189 A1 | 3/2012 | Shen | |
| 2012/0329042 A1 | 12/2012 | Beechem et al. | |

FOREIGN PATENT DOCUMENTS

| | | |
|---|---|---|
| JP | 03-284987 A | 12/1991 |
| JP | 2000-063690 A | 2/2000 |
| JP | 2000-094834 A | 4/2000 |
| JP | 2001-222086 A | 8/2001 |
| JP | 2006-248180 A | 9/2006 |
| JP | 2009-191213 A | 8/2009 |
| WO | WO 00/35920 A2 | 6/2000 |
| WO | WO 2004/072238 A2 | 8/2004 |
| WO | WO 2005/033245 A1 | 4/2005 |
| WO | WO 2005/056689 A2 | 6/2005 |
| WO | WO 2006/111726 A1 | 10/2006 |
| WO | WO 2007/075873 | 7/2007 |
| WO | WO 2007/075987 | 7/2007 |
| WO | WO 2007/076057 | 7/2007 |
| WO | WO 2007/095119 | 8/2007 |
| WO | WO 2009/068751 A1 | 6/2009 |
| WO | WO 2009/091847 | 7/2009 |
| WO | WO 2012/054749 A1 | 4/2012 |
| WO | WO 2012/054784 A1 | 4/2012 |
| WO | WO 2013/189265 A1 | 12/2013 |

OTHER PUBLICATIONS

Eid. J., "Real-Time DNA Sequencing from Single Polymerase Molecules," Science, vol. 323, p. 133-138, 2009.

Dörwald, F. Zaragoza, "Side Reactions in Organic Sysntheses," 2005, Wiley: VCH Weinheim Preface, p. 1-15 & chapter 8, p. 279-308.

Fagan, Adrian et al., "Rigid Cyanine Dye Nucleic aciod Labels," Chem. Comm., 2008, 2004-2006; The Royal Society of Chemistry, 2008, p. 2004-2006.

Halpin, D.R. et al., "DNA Display III. Solid-Phase Organic Synthesis on Unprotected DNA," PLOS Biology, vol. 2, No. 7, p. 1031-1038 (2004).

Jett, J. H. et al., "High-speed DNA sequencing: An approach based upon fluorescence detection of single molecules," J. Biomol. Struct. Dynamics, 7:301-309 (1989).

Knorre, D.G., et al., "General Method for the Synthesis of ATP Gamma-Derivates," FEBS Letters, vol. 70, No. 1 p. 105-108 (Nov. 1976).

Kumar, Shiv, et al., "Terminal Phosphate Labeled Nucleotides: Sunthesis, Applications, and Linker effect on Incorporation by DNA Polymerases," Nucleosides, Nucleotides, and Nucleic Acid, v. 24, No. 5-7, p. 401-408, (2005).

Lagerqvist, J. et al., "Fast DNA sequencing via transverse electronic transport," Nano Lett., 6:779-782 (2006).

Levene, M. J. et al., "Zero-mode waveguides for single-molecule analysis at high concentrations," Science, 299:682-686 (2003).

Lewis E.K.., et al., "Color-Blind Fluorescence Detection for Four-Color DNA Sequencing," Proc.Nat.Academy of Sci., vol. 102, No. 15, p. 5346-5351 (2005).

Licha, K., et al., Document No. 128:218365, retrieved from STN; Feb. 18, 1998, Accession No. 1998:93133 ZCAPLUS, "Synthesis and Characterization of Cyanine Dye-poly(Ethylene Glycol) Conjugates as Contrast Agents for in vivo Fluorescence Imaging").

Licha. K., et al., Document No. 125:81266, retrieved from STN; Jul. 25, 1996, Accesion No. 1996:437966 ZCAPLUS, "Dye-Biomolecule Conjugates as Contrast Agents for in-vivo near-IR Diagnostic Methods".

Metzker, M. L., "Emerging Technologies in DNA Sequencing," Genome Res., 15:1767-1776 (2005).

Narayanan, S., et al., "Clamping Down on Weak Terminal Base Pairs: Oligonucleotides with Molecular Caps as Fidelity-Enhancing Elements at the 5'—and 3'-Terminal Residues", Nucleic Acids Research, 2004, v. 32, n. 9, p. 2901-2911.

Rhee, K. J. et al., "Predicting the utilization of helicopter emergency medical services: an approach based on need," Annals of emergency medicine, 13:916-923 (1984).

Schuler, Benjamin et al., "Polyproline and the 'Spectroscopic Ruler' Revisited with Single-Molecule Fluorescence," PNAS, vol. 102, No. 8, p. 2754-2759 (Feb. 22, 2005).

Stephan, J. et al., "Towards a general procedure for sequencing single DNA molecules," J. Biotechnol., 86:255-267 (2001).

Wang, Li, et al., "Novel Asymmetric Cy5 Dyes: Synthesis, Photostabilities and High Sensitivity in Protein Fluorescence Labeling," J. of Photochem. and Photobio. A: Chem., vol. 210, p. 168-172, 2010.

Werner, J. H. et al., "Progress towards single-molecule DNA sequencing: a one color demonstration," J. Biotechnol., 102:1-14 (2003).

Ishchenko, A.A., et al., Journal of Information Recording Materials, v. 17, No. 1 p. 39-51, 1989.

Supplementary European Search Report issued Jan. 28, 2016, related EP application No. EP13791524.5.

\* cited by examiner

1

2

3

Table 1

FIGURE 4(b)

| Entry # | R1 | R2 | R3 | R4 | R5 | R1' | R2' | R3' | R4' | R5' | absorption |
|---|---|---|---|---|---|---|---|---|---|---|---|
| 1 | H | H | H | H | D | H | H | H | H | D | 642 nm |
| 2 | H | H | COOH | H | D | H | H | COOH | H | D | 650 nm |
| 3 | H | A | H | A | D | H | H | H | COOH | D | 642 nm |
| 4 | H | A | H | A | D | H | H | H | B | D | 641 nm |
| 5 | H | A | H | A | D | H | A | H | A | D | 640 nm |
| 6 | H | A | H | A | D | H | H | COOH | H | D | 648 nm |
| 7 | H | H | SO₃H | H | D | H | H | COOH | H | D | 650 nm |
| 8 | H | H | SO₃H | H | D | H | H | SO₃H | H | D | 649 nm |
| 9 | H | H | G | H | D | H | H | G | H | D | 671 nm |
| 10 | H | H | H | F | D | H | H | H | F | D | 650 nm |
| 11 | H | H | F | H | D | H | H | F | H | C | 671 nm |
| 12 | H | H | F | H | D | H | H | F | H | D | 672 nm |
| 13 | H | H | F | H | C | H | H | F | H | C | 671 nm |
| 14 | OCH₃ | H | F | H | D | OCH₃ | H | F | H | C | 690 nm |
| 15 | H | SO₃H | H | E | D | H | H | H | COOH | D | 637 nm |
| 16 | H | E | H | E | D | H | H | H | COOH | D | 638 nm |
| 17 | H | E | H | E | D | H | SO₃H | H | COOH | D | 640 nm |
| 18 | H | SO₃H | H | E | D | H | SO₃H | H | COOH | D | 640 nm |
| 19 | H | SO₃H | H | COOH | D | H | SO₃H | H | COOH | D | 641 nm |
| 20 | H | A | H | A | D | H | SO₃H | H | COOH | D | 641 nm |
| 21 | H | SO₃H | H | SO₃H | D | H | SO₃H | H | COOH | D | 648 nm |
| 22 | SO₃H | H | SO₃H | H | D | H | SO₃H | H | COOH | D | 650 nm |
| 23 | H | H | NH₂CH₂ | H | D | H | H | SO₃H | H | C | 648 nm |
| 24 | H | SO₃H | H | E | D | H | SO₃H | H | E | D | 640 nm |
| 25 | H | A | H | A | D | H | SO₃H | H | E | D | 640 nm |
| 26 | H | SO₃H | H | SO₃H | D | H | H | H | COOH | D | 648 nm |
| 27 | SO₃H | H | SO₃H | H | D | H | H | H | COOH | D | 650 nm |
| 28 | H | SO₃H | H | SO₃H | D | H | H | COOH | H | D | 653 nm |
| 29 | SO₃H | H | SO₃H | H | D | H | H | COOH | H | D | 658 nm |
| 30 | H | SO₃H | H | SO₃H | D | H | H | SO₃H | H | C | 651 nm |
| 31 | SO₃H | H | SO₃H | H | D | H | H | SO₃H | H | C | 653 nm |
| 32 | H | A | H | A | D | H | COOH | H | E | D | 641 nm |
| 33 | H | E | H | E | D | H | COOH | H | E | D | 639 nm |

Table 2

FIGURE 5(b)

| Entry # | R1 | R2 | R3 | R4 | R5 | R1' | R2' | R3' | R4' | R5' | absorption |
|---|---|---|---|---|---|---|---|---|---|---|---|
| 1 | H | J | H | SO$_3$H | D | H | J | H | SO$_3$H | D | 674 nm |
| 2 | H | J | H | SO$_3$H | D | H | J | H | SO$_3$H | C | 674 nm |
| 3 | H | J | H | SO$_3$H | C | H | J | H | SO$_3$H | C | 675 nm |
| 4 | H | SO$_3$H | H | J | D | H | SO$_3$H | H | J | D | 675 nm |
| 5 | H | SO$_3$H | H | J | D | H | SO$_3$H | H | J | C | 675 nm |
| 6 | H | J | H | J | D | H | J | H | J | D | 675 nm |
| 7 | H | J | H | J | D | H | J | H | J | C | 676 nm |
| 8 | H | J | H | J | C | H | J | H | J | C | 677 nm |
| 9 | H | K | H | SO$_3$H | D | H | K | H | SO$_3$H | D | 675 nm |
| 10 | H | K | H | SO$_3$H | D | H | K | H | SO$_3$H | C | 676 nm |
| 11 | H | K | H | SO$_3$H | C | H | K | H | SO$_3$H | C | 676 nm |
| 12 | H | SO$_3$H | H | K | D | H | SO$_3$H | H | K | D | 675 nm |
| 13 | H | K | H | K | D | H | K | H | K | D | 677 nm |
| 14 | H | H | F | H | D | H | H | F | H | D | 691 nm |
| 15 | SO$_3$H | H | F | H | D | SO$_3$H | H | F | H | C | 689 nm |
| 16 | H | H | SO$_3$H | H | D | H | H | H | H | C | 682 nm |
| 17 | H | H | SO$_3$H | H | D | H | H | SO$_3$H | H | C | 686 nm |
| 18 | H | SO$_3$H | H | SO$_3$H | D | H | SO$_3$H | H | SO$_3$H | C | 677 nm |

Table 3

FIGURE 6(b)

| Entry # | R1 | R2 | R3 | R4 | R5 | R1' | R2' | R3' | R4' | R5' | absorption |
|---|---|---|---|---|---|---|---|---|---|---|---|
| 1 | H | H | H | H | D | H | H | H | H | D | 546 nm |
| 2 | H | H | COOH | H | D | H | H | COOH | H | D | 557 nm |
| 3 | H | H | H | COOH | D | H | H | H | COOH | D | 546 nm |
| 4 | H | A | H | A | D | H | H | H | COOH | D | 546 nm |
| 5 | H | H | H | A | D | H | H | COOH | H | D | 551 nm |
| 6 | H | A | H | A | D | H | H | COOH | H | D | 551 nm |
| 7 | H | OCH$_3$ | H | H | D | H | H | H | COOH | D | 549 nm |
| 8 | H | H | SO$_3$H | H | D | H | H | COOH | H | D | 553 nm |
| 9 | H | H | COOH | H | D | H | H | COOH | H | D | 556 nm |
| 10 | H | COOH | H | COOH | D | H | COOH | H | COOH | D | 545 nm |
| 11 | H | COOH | H | COOH | D | H | A | H | A | C | 551 nm |
| 12 | H | A | H | A | D | H | COOH | H | COOH | D | 547 nm |
| 13 | H | COOH | H | COOH | D | H | H | SO$_3$H | H | C | 549 nm |
| 14 | SO$_3$H | H | F | H | D | SO$_3$H | H | F | H | D | 568 nm |
| 15 | H | H | H | F | D | H | H | H | F | C | 552 nm |
| 16 | H | H | H | F | D | H | F | H | F | D | 552 nm |
| 17 | OCH$_3$ | H | F | H | D | OCH$_3$ | H | F | H | C | 593 nm |
| 18 | H | H | SO$_3$H | H | D | H | H | SO$_3$H | H | D | 550 nm |
| 19 | SO$_3$H | H | SO$_3$H | H | D | H | H | SO$_3$H | H | C | 560 nm |
| 20 | H | SO$_3$H | H | SO$_3$H | D | H | H | SO$_3$H | H | C | 558 nm |
| 21 | H | H | SO$_3$H | H | D | H | H | SO$_3$H | H | C | 551 nm |
| 22 | H | H | H | H | D | H | H | SO$_3$H | H | C | 547 nm |
| 23 | H | H | SO$_3$H | H | D | H | H | H | H | C | 549 nm |
| 24 | H | H | H | H | C | H | H | H | H | C | 549 nm |
| 25 | H | H | H | H | CH$_3$ | H | H | H | H | C | 545 nm |
| 26 | H | H | H | H | CH$_3$ | H | H | H | H | CH$_3$ | 543 nm |
| 27 | H | H | SO$_3$H | H | C | H | H | SO$_3$H | H | C | 553 nm |
| 28 | H | H | H | H | CH$_3$ | H | H | SO$_3$H | H | C | 548 nm |
| 29 | H | H | NH$_2$CH$_2$ | H | D | H | H | COOH | H | C | 549 nm |
| 30 | H | E | H | E | D | H | SO$_3$H | H | COOH | D | 542 nm |
| 31 | H | E | H | E | D | H | E | H | E | D | 540 nm |
| 32 | H | SO$_3$H | H | COOH | D | H | SO$_3$H | H | COOH | D | 543 nm |
| 33 | H | SO$_3$H | H | E | D | H | SO$_3$H | H | COOH | D | 543 nm |
| 34 | H | A | H | A | D | H | SO$_3$H | H | COOH | D | 544 nm |
| 35 | H | SO$_3$H | H | E | D | H | SO$_3$H | H | E | D | 540 nm |
| 36 | H | A | H | A | D | H | SO$_3$H | H | E | D | 543 nm |
| 37 | H | SO$_3$H | H | SO$_3$H | D | H | H | H | COOH | D | 550 nm |
| 38 | SO$_3$H | H | SO$_3$H | H | D | H | H | H | COOH | D | 554 nm |

Table 4

FIGURE 7(b)

| Entry # | R1 | R2 | R3 | R4 | R5 | R1' | R2' | R3' | R4' | R5' | absorption |
|---|---|---|---|---|---|---|---|---|---|---|---|
| 1 | H | J | H | SO₃H | D | H | J | H | SO₃H | D | 579 nm |
| 2 | H | J | H | SO₃H | D | H | J | H | SO₃H | C | 579 nm |
| 3 | H | SO₃H | H | J | D | H | SO₃H | H | J | D | 581 nm |
| 4 | H | SO₃H | H | J | D | H | SO₃H | H | J | C | 581 nm |
| 5 | H | J | H | J | D | H | J | H | J | D | 579 nm |
| 6 | H | J | H | J | D | H | J | H | J | C | 580 nm |
| 7 | H | J | H | J | C | H | J | H | J | C | 581 nm |
| 8 | H | K | H | SO₃H | D | H | K | H | SO₃H | D | 580 nm |
| 9 | H | SO₃H | H | K | D | H | SO₃H | H | K | D | 578 nm |
| 10 | H | K | H | K | D | H | K | H | K | D | 580 nm |
| 11 | H | K | H | SO₃H | D | H | K | H | SO₃H | C | 580 nm |
| 12 | H | H | F | H | D | H | H | F | H | D | 602 nm |
| 13 | SO₃H | H | F | H | D | SO₃H | H | F | H | C | 595 nm |
| 14 | H | H | SO₃H | H | D | H | H | H | H | C | 587 nm |
| 15 | H | SO₃H | H | SO₃H | D | H | H | H | H | C | 582 nm |
| 16 | H | SO₃H | H | SO₃H | D | H | H | SO₃H | H | C | 584 nm |
| 17 | H | H | SO₃H | H | D | H | H | SO₃H | H | D | 587 nm |
| 18 | H | H | SO₃H | H | D | H | H | SO₃H | H | C | 587 nm |
| 19 | H | H | SO₃H | H | C | H | H | SO₃H | H | C | 590 nm |
| 20 | H | H | NH₂CH₂ | H | D | H | H | SO₃H | H | C | 585 nm |
| 21 | H | SO₃H | H | SO₃H | D | H | SO₃H | H | SO₃H | C | 581 nm |
| 22 | H | SO₃H | H | SO₃H | D | H | SO₃H | H | SO₃H | D | 581 nm |
| 23 | SO₃H | H | COOH | H | D | SO₃H | H | COOH | H | D | 590 nm |

FIGURE 8(b)

| Entry # | R1 | R2 | R3 | R4 | R5 | R6 | R7 | R1' | R2' | R3' | R4' | R5' | R6' | absorption |
|---|---|---|---|---|---|---|---|---|---|---|---|---|---|---|
| 1 | H | H | SO₃H | H | D | D | L | H | H | SO₃H | H | D | D | 650 nm |
| 2 | H | H | SO₃H | H | D | D | L | H | H | SO₃H | H | D | D | 653 nm |
| 3 | H | H | SO₃H | H | D | D | M | H | H | SO₃H | H | D | D | 650 nm |
| 4 | H | H | SO₃H | H | D | D | M | H | H | SO₃H | H | D | D | 650 nm |
| 5 | H | H | SO₃H | H | D | CH₃ | M | H | H | SO₃H | H | D | D | 645 nm |
| 6 | H | A | H | A | D | CH₃ | M | H | A | H | A | D | CH₃ | 638 nm |
| 7 | H | A | H | A | D | CH₃ | P | H | A | H | A | D | CH₃ | 640 nm |
| 8 | | | | | | | | | | | | | | |

FIGURE 9(b)

| Entry # | R1 | R2 | R3 | R4 | R5 | R6 | R7 | R1' | R2' | R3' | R4' | R5' | R6' | absorption |
|---|---|---|---|---|---|---|---|---|---|---|---|---|---|---|
| 1 | H | SO₃H | H | SO₃H | D | CH₃ | M | H | SO₃H | H | SO₃H | D | CH₃ | 672 nm |
| 2 | H | SO₃H | H | SO₃H | D | D | M | H | SO₃H | H | SO₃H | D | D | 680 nm |
| 3 | H | SO₃H | H | SO₃H | D | D | M | H | SO₃H | H | SO₃H | D | D | 678 nm |
| 4 | H | SO₃H | H | SO₃H | D | CH₃ | N | H | SO₃H | H | SO₃H | D | CH₃ | 666 nm |
| 5 | | | | | | | | | | | | | | |
| 18 | | | | | | | | | | | | | | |

FIGURE 10(b)

| Entry # | R1 | R2 | R3 | R4 | R5 | R1' | R2' | R3' | R4' | R5' | absorption |
|---|---|---|---|---|---|---|---|---|---|---|---|
| 2009 | SO$_3$H | H | H | F | D | SO$_3$H | H | H | L | D | 612 nm |
| 2010 | SO$_3$H | H | H | L | D | SO$_3$H | H | H | L | D | 612 nm |
| 2011 | SO$_3$H | H | H | F | D | SO$_3$H | H | H | F | D | 612 nm |
| 2013 | H | H | H | F | D | H | H | H | L | D | 614 nm |
| 2014 | H | H | H | L | D | H | H | H | L | D | 616 nm |
| 2016 | H | H | H | F | D | H | H | H | F | D | 616 nm |
| 2018 | H | H | H | SO$_3$H | D | H | H | H | SO$_2$NXY* | D | 607 nm |
| 2019 | H | H | H | SO$_3$H | D | H | H | H | SO$_2$NHZ* | D | 606 nm |
| 2021 | H | H | H | SO$_3$H | D | H | H | H | SO$_3$H | D | 594 nm |
| 2022 | H | H | H | F | D | H | H | H | M | D | 617 nm |
| 2023 | H | H | H | M | D | H | H | H | M | D | 616 nm |
| 2024 | SO$_3$H | H | H | M | D | SO$_3$H | H | H | N | D | 611 nm |
| 2026 | H | H | H | F | D | H | H | H | N | D | 611 nm |
| 2027 | H | H | H | N | D | H | H | H | N | D | 610 nm |
| 2028 | SO$_3$H | H | H | F | D | SO$_3$H | H | H | M | D | 611 nm |
| 2029 | SO$_3$H | H | H | F | D | SO$_3$H | H | H | N | D | 610 nm |
| 2030 | H | H | H | F | D | H | H | H | O | D | 613 nm |
| 2031 | SO$_3$H | H | H | SO$_3$H | C | SO$_3$H | H | H | SO$_3$H | D | 606 nm |
| 2032 | SO$_3$H | SO$_3$H | H | SO$_3$H | D | SO$_3$H | H | H | SO$_3$H | D | 607 nm |
| 2033 | SO$_3$H | H | H | M | D | SO$_3$H | H | H | M | D | 614 nm |

| Entry # | R1 | R2 | R3 | R4 | R5 | R6 | R1' | R2' | R3' | R4' | R5' | R6' | absorption |
|---|---|---|---|---|---|---|---|---|---|---|---|---|---|
| 1 | H | H | H | H | D | CH₃ | H | H | H | H | D | CH₃ | 546 nm |
| 2 | H | H | COOH | H | D | CH₃ | H | H | COOH | H | D | CH₃ | 557 nm |
| 3 | H | H | H | COOH | D | CH₃ | H | H | H | COOH | D | CH₃ | 546 nm |
| 4 | H | A | H | A | D | CH₃ | H | H | H | COOH | D | CH₃ | 546 nm |
| 5 | H | H | H | A | D | CH₃ | H | H | COOH | H | D | CH₃ | 551 nm |
| 6 | H | A | H | A | D | CH₃ | H | H | COOH | H | D | CH₃ | 551 nm |
| 7 | H | OCH₃ | H | H | D | CH₃ | H | H | H | COOH | D | CH₃ | 549 nm |
| 8 | H | H | SO₃H | H | D | CH₃ | H | H | COOH | H | D | CH₃ | 553 nm |
| 9 | H | H | COOH | H | D | CH₃ | H | H | COOH | H | D | CH₃ | 556 nm |
| 10 | H | COOH | H | COOH | D | CH₃ | H | COOH | H | COOH | D | CH₃ | 545 nm |
| 11 | H | COOH | H | COOH | D | CH₃ | H | A | H | A | C | CH₃ | 551 nm |
| 12 | H | A | H | A | D | CH₃ | H | COOH | H | COOH | D | CH₃ | 547 nm |
| 13 | H | COOH | H | COOH | D | CH₃ | H | H | SO₃H | H | C | CH₃ | 549 nm |
| 14 | SO₃H | H | F | H | D | CH₃ | SO₃H | H | F | H | D | CH₃ | 568 nm |
| 15 | H | H | H | F | D | CH₃ | H | H | H | F | C | CH₃ | 552 nm |
| 16 | H | H | H | F | D | CH₃ | H | F | H | F | D | CH₃ | 552 nm |
| 17 | OCH₃ | H | F | H | D | CH₃ | OCH₃ | H | F | H | C | CH₃ | 593 nm |
| 18 | H | H | SO₃H | H | D | CH₃ | H | H | SO₃H | H | D | CH₃ | 550 nm |
| 19 | SO₃H | H | SO₃H | H | D | CH₃ | H | H | SO₃H | H | C | CH₃ | 560 nm |
| 20 | H | SO₃H | H | SO₃H | D | CH₃ | H | H | SO₃H | H | C | CH₃ | 558 nm |
| 21 | H | H | SO₃H | H | D | CH₃ | H | H | SO₃H | H | C | CH₃ | 551 nm |
| 22 | H | H | H | H | D | CH₃ | H | H | SO₃H | H | C | CH₃ | 547 nm |
| 23 | H | H | SO₃H | H | D | CH₃ | H | H | H | H | C | CH₃ | 549 nm |
| 24 | H | H | H | H | C | CH₃ | H | H | H | H | C | CH₃ | 549 nm |
| 25 | H | H | H | H | CH₃ | CH₃ | H | H | H | H | C | CH₃ | 545 nm |
| 26 | H | H | H | H | CH₃ | CH₃ | H | H | H | H | CH₃ | CH₃ | 543 nm |
| 27 | H | H | SO₃H | H | C | CH₃ | H | H | SO₃H | H | C | CH₃ | 553 nm |
| 28 | H | H | H | H | CH₃ | CH₃ | H | H | SO₃H | H | C | CH₃ | 548 nm |
| 29 | H | H | NH₂CH₂ | H | D | CH₃ | H | H | COOH | H | C | CH₃ | 549 nm |
| 30 | H | E | H | E | D | CH₃ | H | SO₃H | H | COOH | D | CH₃ | 542 nm |
| 31 | H | E | H | E | D | CH₃ | H | E | H | E | D | CH₃ | 540 nm |
| 32 | H | SO₃H | H | COOH | D | CH3 | H | SO₃H | H | COOH | D | CH₃ | 543 nm |
| 33 | H | SO₃H | H | E | D | CH₃ | H | SO₃H | H | COOH | D | CH₃ | 543 nm |
| 34 | H | A | H | A | D | CH₃ | H | SO₃H | H | COOH | D | CH₃ | 544 nm |
| 35 | H | SO₃H | H | E | D | CH₃ | H | SO₃H | H | E | D | CH₃ | 540 nm |
| 36 | H | A | H | A | D | CH₃ | H | SO₃H | H | E | D | CH₃ | 543 nm |

| Entry # | R1 | R2 | R3 | R4 | R5 | R6 | R1' | R2' | R3' | R4' | R5' | R6' | absorption |
|---|---|---|---|---|---|---|---|---|---|---|---|---|---|
| 37 | H | SO₃H | H | SO₃H | D | CH₃ | H | H | H | COOH | D | CH₃ | 550 nm |
| 38 | SO₃H | H | SO₃H | H | D | CH₃ | H | H | H | COOH | D | CH₃ | 554 nm |
| 39 | H | H | SO₃H | H | D | D | H | COOH | H | E | D | CH₃ | 550 nm |
| 40 | H | A | H | A | D | CH₃ | H | COOH | H | E | D | D | 545 nm |
| 41 | H | E | H | E | D | CH₃ | H | COOH | H | E | D | D | 542 nm |
| 42 | H | H | SO₃H | H | D | CH₃ | H | H | SO₃H | H | C | D | 555 nm |

FIGURE 11(c)

PHOSPHOLINKED DYE ANALOGS WITH AN AMINO ACID LINKER

CROSS-REFERENCE TO RELATED APPLICATIONS

This application is a continuation of U.S. patent application Ser. No. 13/218,436 filed on Aug. 25, 2011 which claims priority to U.S. Provisional Application Nos. 61/377,004, filed on Aug. 25, 2010, 61/377,022, filed on Aug. 25, 2010, 61/377,031, filed on Aug. 25, 2010, 61/377,038, filed on Aug. 25, 2010, and 61/377,048, filed on Aug. 25, 2010 the disclosures of which are incorporated herein by reference in their entirety for all purposes.

BACKGROUND OF THE INVENTION

1. Field of Invention

The present invention relates generally to the synthesis of fluorescent compounds that are analogues of cyanine dyes. The compounds of the invention are fluorophores that are derivatized to allow their facile attachment to another moiety. The invention also relates to improved methods for sequencing and genotyping nucleic acid in a single molecule configuration. An exemplary method involves detection of single molecules of fluorescent labels released from a nucleic acid during synthesis of an oligonucleotide.

2. Background

There is a continuous and expanding need for rapid, highly specific methods of detecting and quantifying chemical, biochemical and biological substances as analytes in research and diagnostic mixtures. Of particular value are methods for measuring small quantities of nucleic acids, peptides, saccharides, pharmaceuticals, metabolites, microorganisms and other materials of diagnostic value. Examples of such materials include narcotics and poisons, drugs administered for therapeutic purposes, hormones, pathogenic microorganisms and viruses, peptides, e.g., antibodies and enzymes, and nucleic acids, particularly those implicated in disease states.

The presence of a particular analyte can often be determined by binding methods that exploit the high degree of specificity, which characterizes many biochemical and biological systems. Frequently used methods are based on, for example, antigen-antibody systems, nucleic acid hybridization techniques, and protein-ligand systems. In these methods, the existence of a complex of diagnostic value is typically indicated by the presence or absence of an observable "label" which is attached to one or more of the interacting materials. The specific labeling method chosen often dictates the usefulness and versatility of a particular system for detecting an analyte of interest. Preferred labels are inexpensive, safe, and capable of being attached efficiently to a wide variety of chemical, biochemical, and biological materials without significantly altering the important binding characteristics of those materials. The label should give a highly characteristic signal, and should be rarely, and preferably never, found in nature. The label should be stable and detectable in aqueous systems over periods of time ranging up to months. Detection of the label is preferably rapid, sensitive, and reproducible without the need for expensive, specialized facilities or the need for special precautions to protect personnel. Quantification of the label is preferably relatively independent of variables such as temperature and the composition of the mixture to be assayed.

A wide variety of labels have been developed, each with particular advantages and disadvantages. For example, radioactive labels are quite versatile, and can be detected at very low concentrations. However, such labels are expensive, hazardous, and their use requires sophisticated equipment and trained personnel. Thus, there is wide interest in non-radioactive labels, particularly in labels that are observable by spectrophotometric, spin resonance, and luminescence techniques, and reactive materials, such as enzymes that produce such molecules.

Labels that are detectable using fluorescence spectroscopy are of particular interest because of the large number of such labels that are known in the art. Moreover, as discussed below, the literature is replete with syntheses of fluorescent labels that are derivatized to allow their attachment to other molecules, and many such fluorescent labels are commercially available.

Fluorescent nucleic acid probes are important tools for genetic analysis, in both genomic research and development, and in clinical medicine. As information from the Human Genome Project accumulates, the level of genetic interrogation mediated by fluorescent probes will expand enormously. One particularly useful class of fluorescent probes includes self-quenching probes, also known as fluorescence energy transfer probes, or FET probes. The design of different probes using this motif may vary in detail. In an exemplary FET probe, both a fluorophore and a quencher are tethered to a nucleic acid. The probe is configured such that the fluorophore is proximate to the quencher and the probe produces a signal only as a result of its hybridization to an intended target. Despite the limited availability of FET probes, techniques incorporating their use are rapidly displacing alternative methods.

To enable the coupling of a fluorescent label with a group of complementary reactivity on a carrier molecule, a reactive derivative of the fluorophore is prepared. For example, Reedy et al. (U.S. Pat. No. 6,331,632) describe cyanine dyes that are functionalized at an endocyclic nitrogen of a heteroaryl moiety with hydrocarbon linker terminating in a hydroxyl moiety. The hydroxyl moiety is converted to the corresponding phosphoramidite, providing a reagent for conjugating the cyanine dye to a nucleic acid. Waggoner (U.S. Pat. No. 5,627,027) has prepared derivatives of cyanine and related dyes that include a reactive functional group through which the dye is conjugated to another species. The compounds set forth in Ohno et al. (U.S. Pat. No. 5,106,990) include cyanine dyes that have a $C_1$-$C_5$ hydrocarbyl linker terminated with a sulfonic acid, a carboxyl or a hydroxyl group. Randall et al. (U.S. Pat. Nos. 6,197,956; 6,114,350; 6,224,644; and 6,437,141) disclose cyanine dyes with a linker arm appended to an endocyclic heteroaryl nitrogen atom. The linkers include a thiol, amine or hydroxyl group, or a protected analogue of these residues. Additional linker arm-cyanine dyes are disclosed by Brush et al. (U.S. Pat. Nos. 5,808,044; 5,986,086). These cyanine dyes are derivatized at both endocyclic heteroaryl nitrogen atoms with a hydrocarbyl linker terminating in a hydroxyl moiety. One hydroxyl moiety is converted to the corresponding phosphoramidite and the other is protected as a dimethoxytrityl ether.

Cyanine dyes are particularly popular fluorophores and are widely used in many biological applications due to their high quantum yield and high molar absorbtivity. Cyanine dyes are, however, susceptible to photobleaching during prolonged excitation. Moreover, due the rigid planar structure of these compounds, they have a tendency to stack and self-quench. Thus, provision of cyanine dyes having an enhanced brightness and decreased tendency to stack, thereby mitigating the effects of photobleaching and stacking is an important object. Furthermore, cyanine dyes that are hydrophilic are less attracted to other species such as proteins and surfaces, which reduces adventitious binding of the fluorophore and enhances the precision and accuracy of assays and other analyses utilizing cyanine fluorophores. The present invention meets these objects and other needs.

SUMMARY OF THE INVENTION

The present invention provides a class of cyanine-based fluorophores modified to improve their fluorescent and other physicochemical properties. Thus, it is a general object of the invention to provide cyanine dyes that are hydrophilic, are resistant to photobleaching, or maintain a high level of brightness despite photobleaching, and have a lower tendency to stack or otherwise aggregate than current cyanine fluorophores.

Exemplary dyes of the invention find particular use in DNA sequencing modalities, particularly single molecule sequencing modalities. Previous dyes used in such applications have had less than ideal properties. For example, certain dyes give suboptimal performance, because, as was discovered, the dyes are insufficiently hydrophilic, insufficiently bright, do not emit steadily (i.e., blink), undergo photobleaching upon prolonged irradiation or they aggregate. These deficiencies can cause misreads in DNA sequencing analyses, providing inaccurate results. In various embodiments, the present invention provides a solution to one or more of these factors contributing to suboptimal dye performance. In various embodiments, the hydrophilicity of the dyes is enhanced by the addition of to the cyanine core or a side group attached to the cyanine core of a water-soluble polymer, sulfonic acid, or carboxylic acid moieties or groups containing sulfonic acid or carboxylic acid moieties. Moreover, it was discovered that substitution of a cyanine dye with charged, hydrophilic moieties protects the cyanine chromophore from the dye's microenvironment and reduces blinking, aggregation and photobleaching. Thus, in various embodiments, the dyes are brighter, more photostable and their emission is more constant. Furthermore, for DNA sequencing, particularly single molecule sequencing, resolution of the absorbance of the dye emissions is important to sensitivity and accuracy of the measurements underlying the sequence determination. Accordingly, in various embodiments, the present invention provides dyes with emissions tuned to achieve useful levels of resolution in the emission peaks of the dyes when they are used in combinations of 2, 3, 4 or more different dyes attached to nucleic acids. Thus, in various embodiments, the present invention provides a solution to the problem. In exemplary embodiments, the dyes of the invention provide at least a 2%, at least a 5%, at least a 7% or at least a 10% improvement in readlength in a single molecule DNA sequencing protocol when compared with dyes that are not functionalized as are the dyes of the invention.

In exemplary embodiments, the dyes of the invention are utilized in DNA sequencing in real time using a single polymerase enzyme attached to the bottom of the small nano-meter size hole called zero-mode waveguide (ZMW). Fluorescent signals of 4 different colors that correspond to 4 different DNA bases: A, G, C, T are detected. Since the most robust methodologies read through as many bases as possible, it is desirable to utilize dyes that do not limit the readlength or the accuracy of the measurements. The water-soluble, cyanine dyes of the invention are of use in such measurements and in some embodiments increase the accuracy of the measurements by at least 2%, at least 5%, at least 7% or at least 10% in a single molecule DNA sequencing protocol when compared with dyes that are not functionalized as are the dyes of the invention.

In an exemplary embodiment, the dyes of the invention include a rigid linker arm with a peptide backbone. The peptide provides a versatile linker arm, the structure and position of which is readily alterable, thereby allowing the conjugation of the label through a variety of positions on the cyanine nucleus to a carrier molecule. Exemplary species to which the amino acid or peptide linked fluorophores are bound include nucleic acids and polyvalent moieties (e.g., a scaffold). Choice of the amino acid or peptide constituent of the linker influences the properties of the conjugate. For example, selection of an amino acid or peptide linker was found to allow the strength and time course of the interaction between the fluorescent nucleic acid analogue to be varied. In exemplary embodiments, the amino acid or peptide moiety enhances the interaction between the compound of the invention and a protein such as a DNA polymerase, lowering the $K_{off}$ of the sequencing reaction.

The versatility of the labels set forth herein provides a marked advantage over currently utilized cyanine labels, probes assembled using those labels and methods relying upon such labels and probes. Moreover, the present invention provides a class of chemically versatile labels in which the fluorophore can be engineered to have a desired light excitation and emission profile.

In various embodiments, the present invention provides a class of conjugates that include fluorophores bound to an amino acid or peptide. In exemplary embodiments, the amino acid or peptide serves as a linker and is itself bound to another species.

In an exemplary embodiment, the present invention provides a fluorescent dye having the formula:

wherein $R^1$ is a fluorescent dye moiety. AA is an amino acid. The index n is selected from the integers 1, 2, 3, 4, 5, 6, 7, 8, 9, 10, 11 and 12, and when n is two or greater, each n amino acid is independently selected. X is a member selected from a polyvalent moiety, and a moiety including the structure:

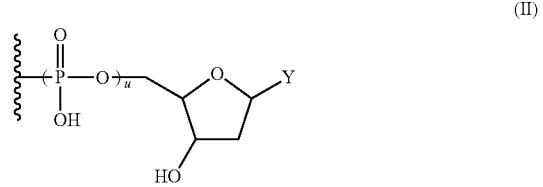

wherein Y is a nucleobase; and u is selected from the integers 1, 2, 3, 4, 5, 6, 7 and 8. The index y is selected from the integers 1, 2, 3, 4, 5, 6, 7 and 8, such that when y is 2 or greater, X is a polyvalent moiety. $L^1$ and $L^2$ are independently selected from bonds, adaptors and substituted or unsubstituted alkyl and substituted or unsubstituted heteroalkyl moieties. The index a is 0 or 1, and b is an integer selected from 0, 1, 2, 3, 4, 5, 6, 7 and 8.

In various embodiments, the invention provides compounds in which the fluorescent dye moiety has the formula:

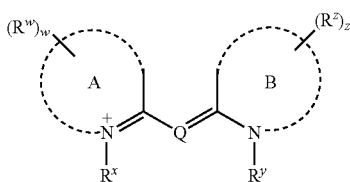

A and B independently selected monocyclic, bicyclic or polycyclic aryl or heteroaryl moieties. When A and/or B is a bicyclic polycyclic moiety, two or more of the rings are optionally fused. Exemplary polycyclic moieties include indole and benzoindole. Q is a substituted or unsubstituted methine moiety (e.g., —(CH=C(R))$_c$—CH=), in which c is an integer selected from 1, 2, 3, 4, or 5 and R is an "alkyl group substituent" as defined herein. When two or more R groups are present, they are optionally joined to form a ring. Each $R^w$, $R^x$, $R^y$ and $R^z$ is independently selected from those substituents set forth in the Definitions section herein as "alkyl group substituents" and "aryl group substituents." The indices w and z are independently selected from the integers from 0 to 6. In an exemplary embodiment, at least one of $R^w$, $R^x$, $R^y$ and $R^z$ is C(O)NR°(CH$_2$)$_h$G in which G is a member selected from SO$_3$H and CO$_2$H, R° is H or substituted or unsubstituted alkyl or heteroalkyl and the index h is an integer from 1 to 20. In exemplary embodiments, at least 1, 2, 3, 4, 5, or 6 of $R^x$, $R^y$, $R^w$ and $R^z$ are alkylsulfonic acid or heteroalkylsulfonic acid and at least one of these moieties is alkylcarboxylic acid or heteroalkylcarboxylic acid. In exemplary embodiments, at least one of $R^w$, $R^x$, $R^y$ and $R^z$ includes a water-soluble polymer (e.g., poly(ethylene glycol)) component.

In various embodiments, at least one of $R^w$, $R^x$, $R^y$ and $R^z$ is functionalized with an additional dye moiety bonded to the cyanine dye core shown above. In an exemplary embodiment, the additional dye moiety is bonded to the dye core through a linker, a polyvalent scaffold, or a linker-polyvalent scaffold conjugate.

In various embodiments, the invention provides a composition, comprising an enzyme, and a substrate for the enzyme, the substrate comprising a component reacted upon by the enzyme, a fluorescent label component and an amino acid or peptide linker component conjugating these two components. The linker component interacts with the enzyme to increase the affinity of the flurophore-linker-enzyme reactive component with the enzyme, reducing the $K_m$ of the reaction between the enzyme and the enzyme-reactive component relative to that of an analogous reaction in which the conjugate does not include the linker component. Exemplary interaction modalities by which the linker increases the affinity of the conjugate for the enzyme include, without limitation, electrostatic, hydrophobic and steric interactions. In various embodiments, the $K_m$ is reduced at least 10%, at least 20%, at least 30%, at least 40% or at least 50% relative to the $K_m$ of the reaction with an analogous conjugate without the linker component.

In a further aspect, the invention provides a method of monitoring an enzyme reaction. The method generally comprises providing a reaction mixture comprising the enzyme and at least a first reactant composition. An exemplary reactant composition comprises a compound having a component that reacts with the enzyme, a fluorescent label component, and an adaptor or linker-adaptor component joining the reactant component to the label component. The reaction mixture is then illuminated to excite the fluorescent label component, and a fluorescent signal from the reaction mixture characteristic of the enzyme reaction is detected.

The invention also provides methods of monitoring nucleic acid synthesis reactions. The methods comprise contacting a polymerase/template/primer complex with a fluorescently labeled nucleotide or nucleotide analog having a nucleotide or nucleotide analog component, a fluorescent label component, and an adaptor or linker-adaptor component joining die nucleotide or nucleotide analog component to the label component. A characteristic signal from the fluorescent dye is then detected that is indicative of incorporation of the nucleotide or nucleotide analog into a primer extension reaction.

In various embodiments, the present invention provides methods of using the compounds described herein for performing nucleic acid analyses, and particularly nucleic acid sequence analyses. In various embodiments, the compounds of the invention are used in single molecule nucleic acid sequencing. Exemplary methods of the invention comprise using a template nucleic acid complexed with a polymerase enzyme in a template dependent polymerization reaction to produce a nascent nucleic acid strand, contacting the polymerase and template nucleic acid with a compound of the invention, and detecting whether or not the compound or a substructure thereof (e.g., a monophosphate nucleic acid) was incorporated into the nascent strand during the polymerization reaction, and identifying a base in the template strand based upon incorporation of the compound. Preferably, the foregoing process is carried out so as to permit observation of individual nucleotide incorporation reactions, through the use of, for example, an optical confinement, that allows observation of an individual polymerase enzyme, or through the use of a heterogeneous assay system, where fluorophores released from incorporated analogs are detected.

The compounds and compositions of the invention are of use in single molecule or single molecule real time (SMRT) DNA sequencing assays. Of particular note in this context is the ability provided by the invention to design fluorophores with selected absorbance and emission properties including wavelength and intensity. The compounds of the invention provide for very versatile assay design. For example, according to the present invention a series of fluorophores of use in an assay are readily designed to have selected absorbance and emission wavelengths and emission intensities, allowing multiple fluorophores to be utilized and distinguished in an assay. In exemplary embodiments, use of compounds of the invention in a multifluorophore assay, e.g., single molecule DNA sequencing, enhances assay performance by at least about 10%, at least about 20% or at least about 30% over a similar assay using currently available fluorophores.

Other aspects, embodiments and objects of the present invention will be apparent from the detailed description that follows.

BRIEF DESCRIPTION OF THE DRAWINGS

FIG. 4(b) is a tabulation of exemplary dye component precursors according to the generic structure of FIG. 4(a).

FIG. 5(b) is a tabulation of exemplary dye component precursors according to the generic structure of FIG. 5(a).

FIG. 6(b) is a tabulation of exemplary dye component precursors according to the generic structure of FIG. 6(a).

FIG. 7(b) is a tabulation of exemplary dye component precursors according to the generic structure of FIG. 7(a).

FIG. 8(b) is a tabulation of exemplary dye component precursors according to the generic structure of FIG. 8(a).

FIG. 9(b) is a tabulation of exemplary dye component precursors according to the generic structure of FIG. 9(a).

FIG. 10(b) is a tabulation of exemplary dye component precursors according to the generic structure of FIG. 10(a).

FIGS. 11(b) and 11(c) is a tabulation of exemplary dye component precursors according to the generic structure of FIG. 11(a).

DETAILED DESCRIPTION OF THE INVENTION

Abbreviations

Figure 1A:
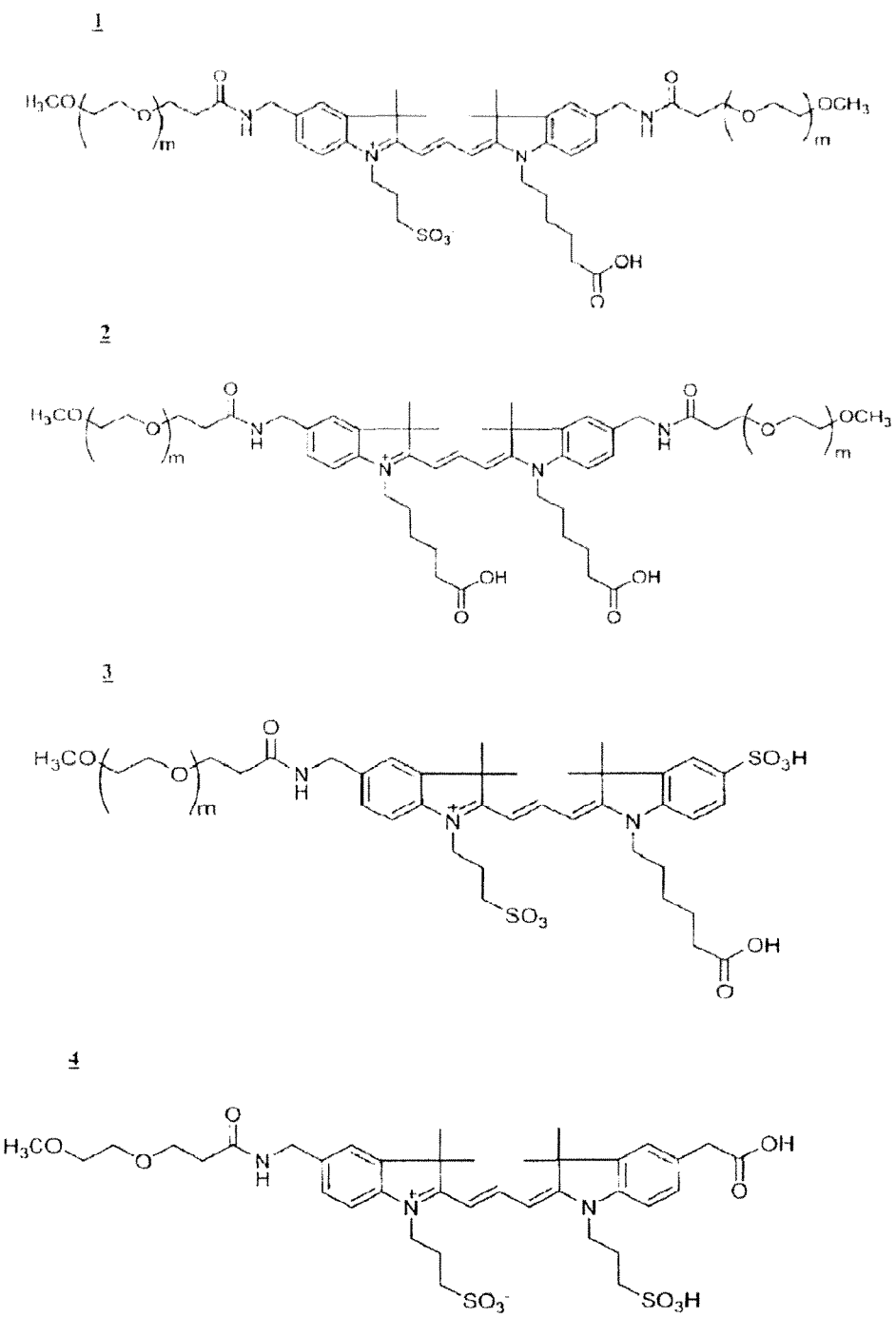
FIG. 1(a), FIG. 1(b) and FIG. 1(c) show structures of exemplary precursors of the dye components of the conjugates of the invention. Once incorporated into a conjugate of the invention, the conjugated dyes can be further conjugated to one or more additional species, e.g., a polyvalent scaffold (e.g., into a FRET pair), conjugated to a nucleic acid or to a linker.
Figure 1B:
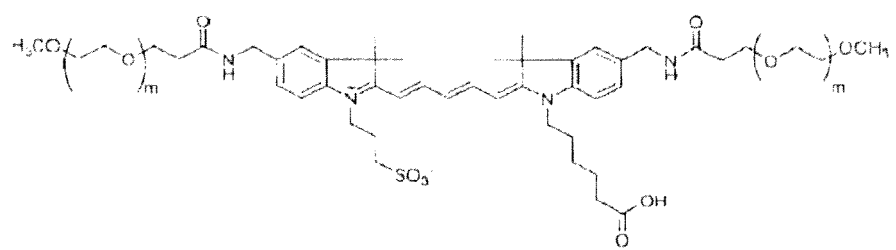
Figure 1B:
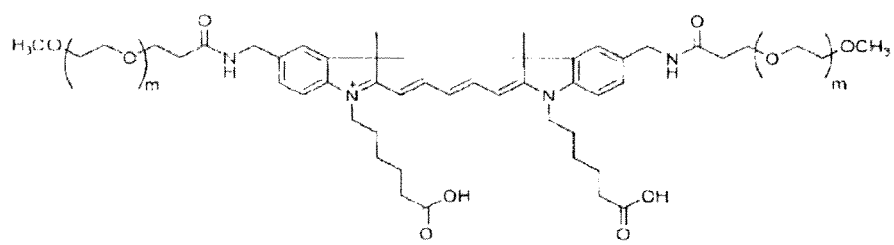
Figure 1B:
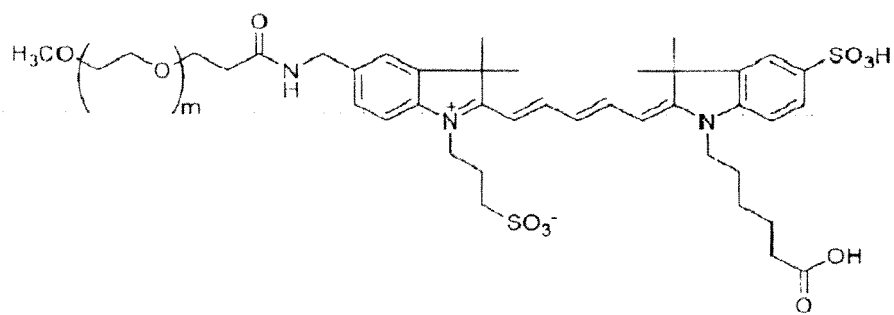
Figure 1C:
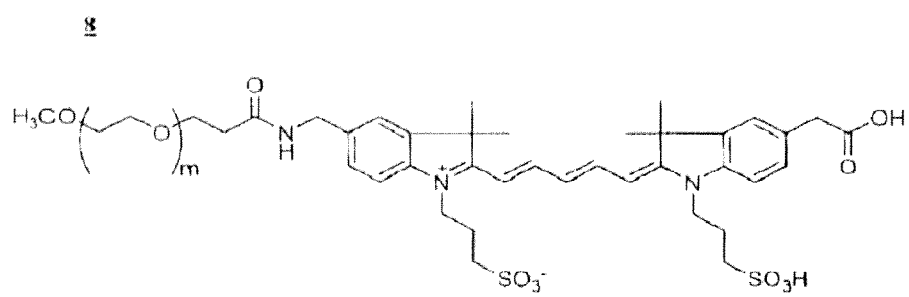
Figure 2A:
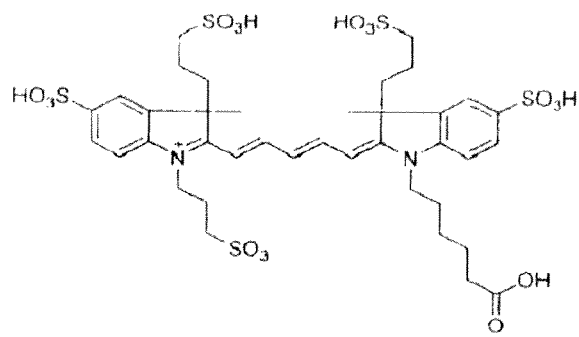
FIG. 2(a), FIG. 2(b) and FIG. 2(c) show structures of exemplary precursors of the dye components of the conjugates of the invention. Once incorporated into a conjugate of the invention, the conjugated dyes can be further conjugated to one or more additional species, e.g., a polyvalent scaffold (e.g., into a FRET pair), conjugated to a nucleic acid or to a linker.
Figure 2A:
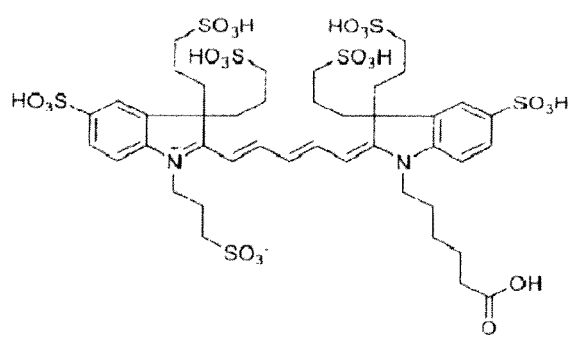
Figure 2A:
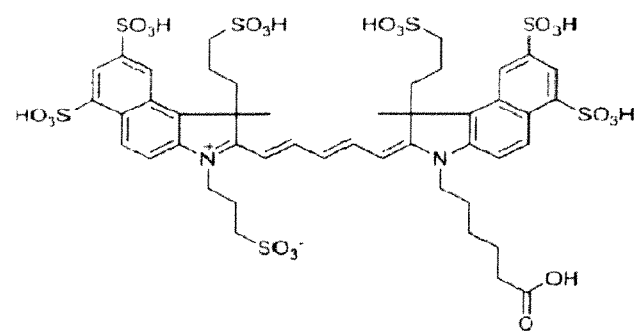
Figure 2B:
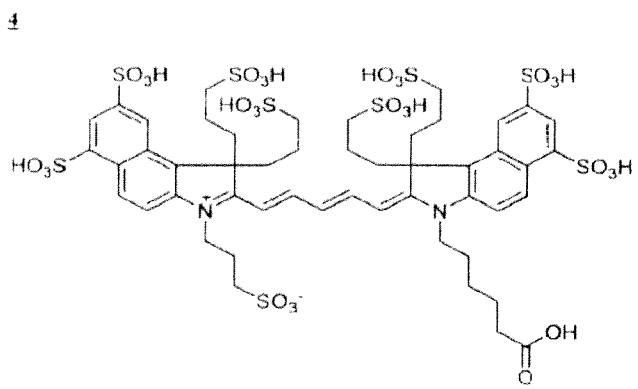
Figure 2B:
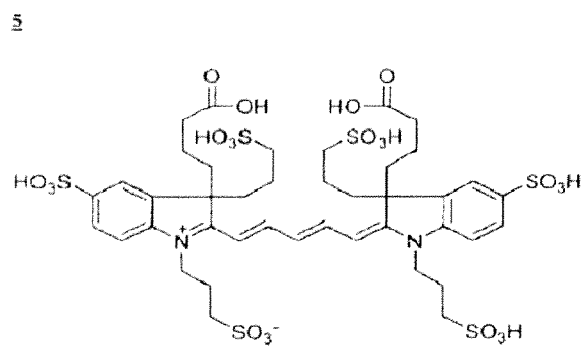
Figure 2B:
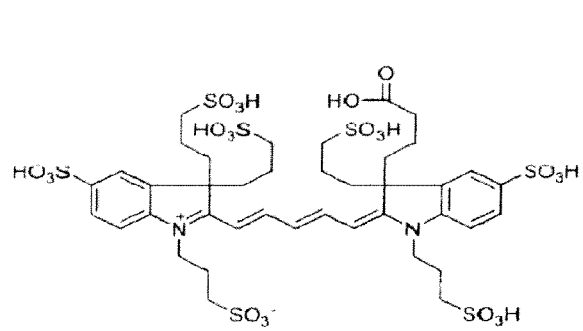
Figure 2C:
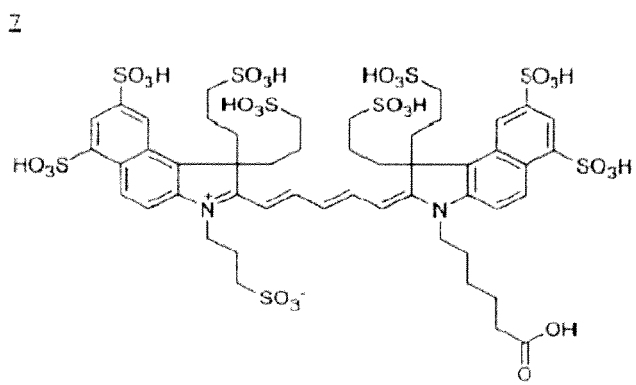
Figure 2C:
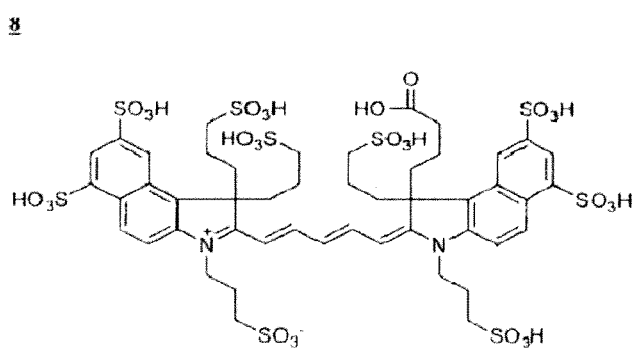
Figure 2C:
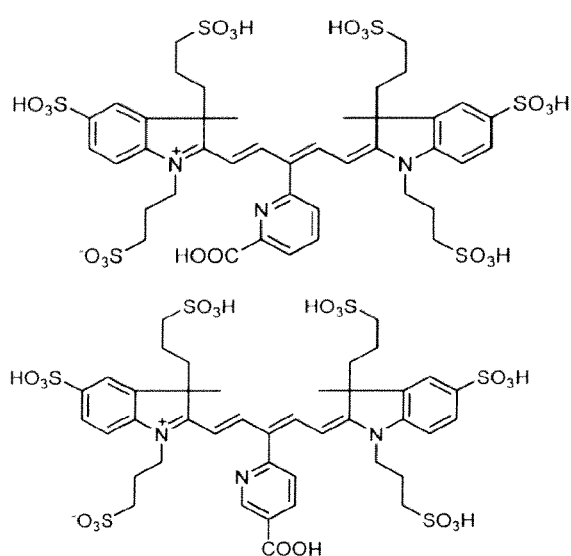
Figure 3A:
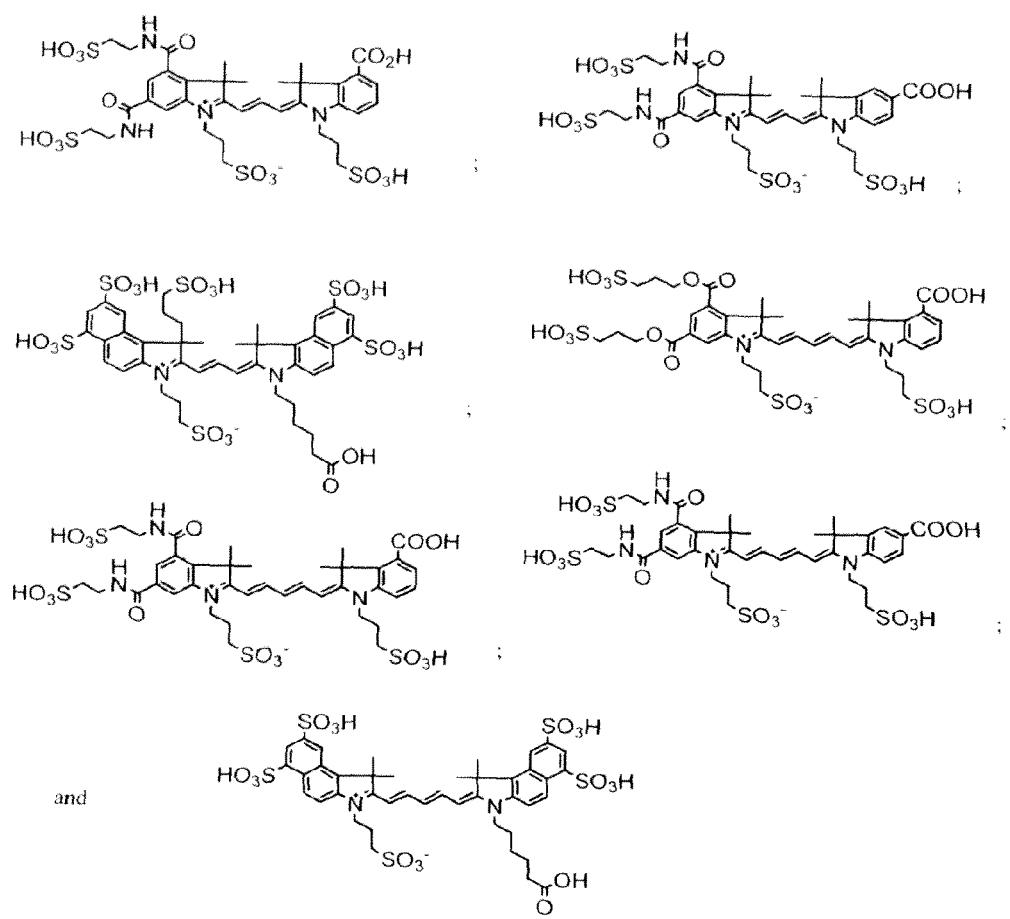
FIG. 3(a) and FIG. 3(b) show structures of exemplary precursors of the dye components of the conjugates of the invention. Once incorporated into a conjugate of the invention, the conjugated dyes can be further conjugated to one or more additional species, e.g., a polyvalent scaffold (e.g., into a FRET pair), conjugated to a nucleic acid or to a linker.
Figure 3B:
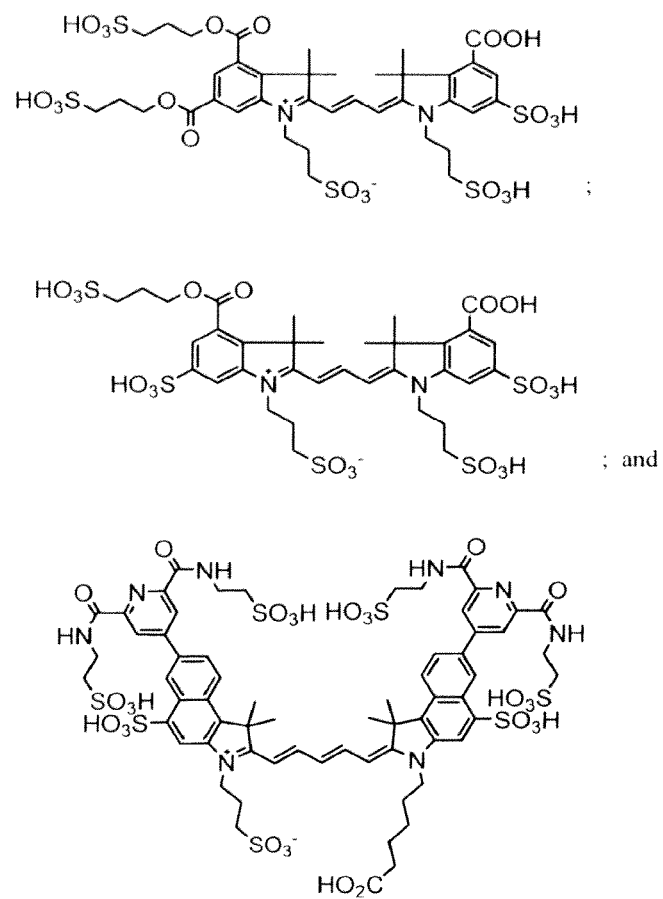
Figure 4A:
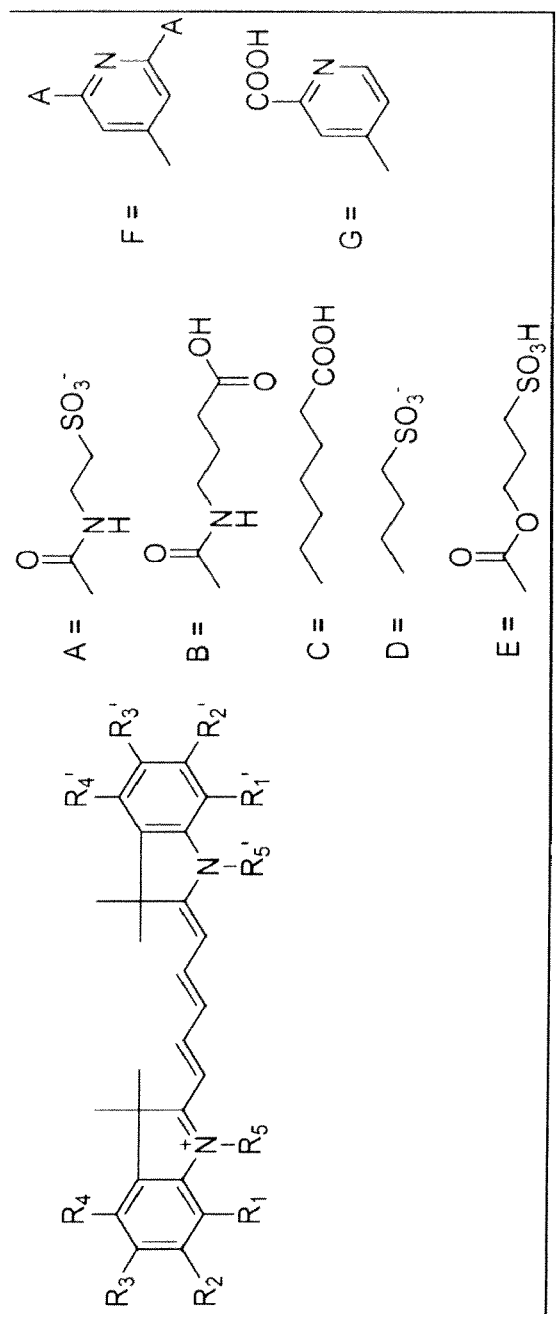
FIG. 4(a) is a generic structure of exemplary precursors of the dye components of the conjugates of the invention and of substituents on these precursors. Once incorporated into a conjugate of the invention, the conjugated dyes can be further conjugated to one or more additional species, e.g., a polyvalent scaffold (e.g., into a FRET pair), conjugated to a nucleic acid or to a linker.
Figure 5A:
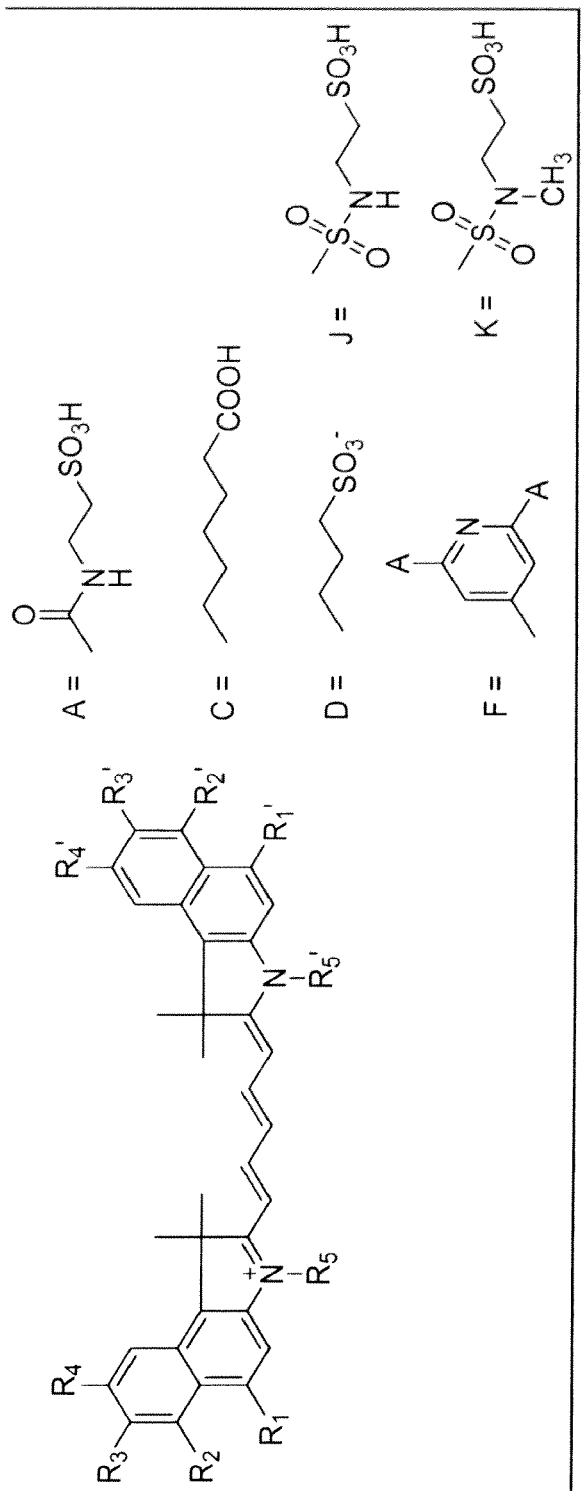
FIG. 5(a) is a generic structure of exemplary precursors of the dye components of the conjugates of the invention and of substituents on these precursors. Once incorporated into a conjugate of the invention, the conjugated dyes can be further conjugated to one or more additional species, e.g., a polyvalent scaffold (e.g., into a FRET pair), conjugated to a nucleic acid or to a linker.
Figure 6A:
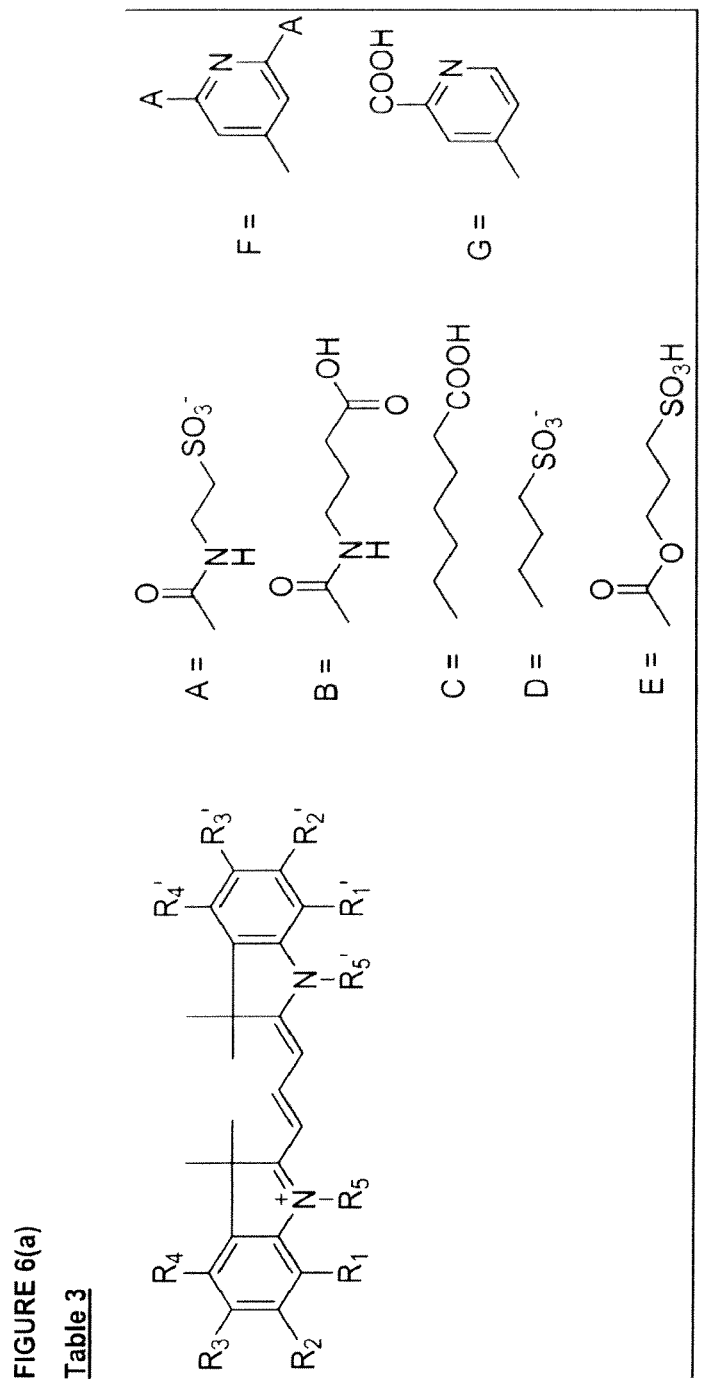
FIG. 6(a) is a generic structure of exemplary precursors of the dye components of the conjugates of the invention and of substituents on these precursors. Once incorporated into a conjugate of the invention, the conjugated dyes can be further conjugated to one or more additional species, e.g., a polyvalent scaffold (e.g., into a FRET pair), conjugated to a nucleic acid or to a linker.
Figure 7A:
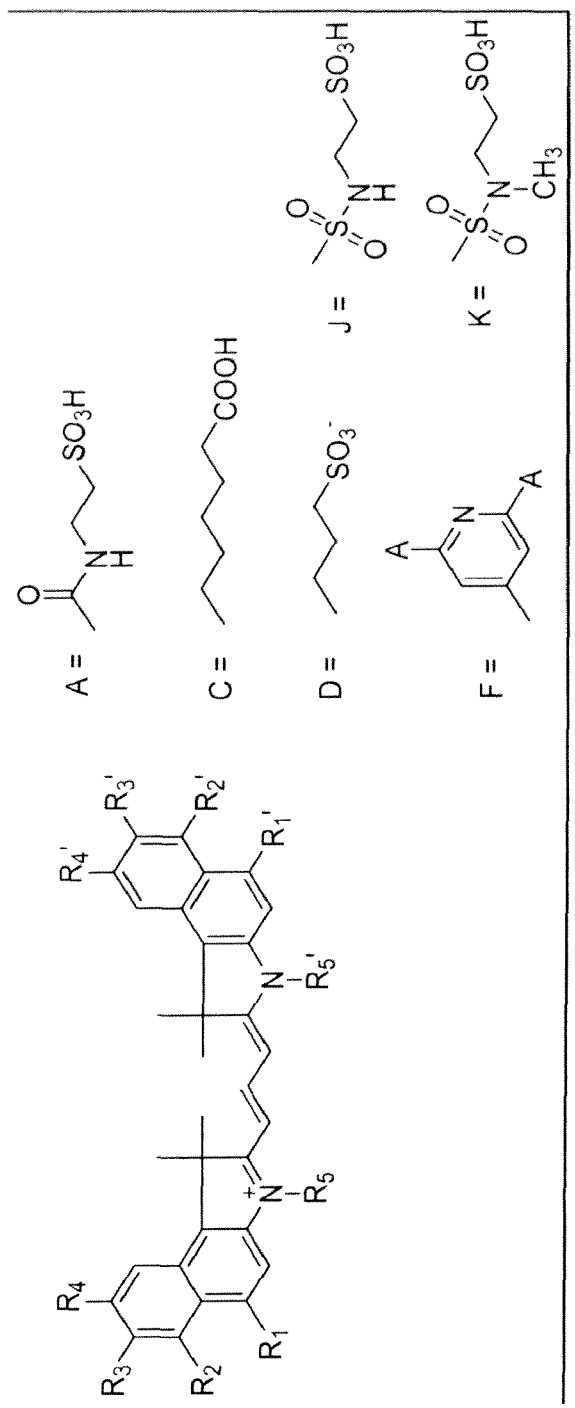
FIG. 7(a) is a generic structure of exemplary precursors of the dye components of the conjugates of the invention and of substituents on these precursors. Once incorporated into a conjugate of the invention, the conjugated dyes can be further conjugated to one or more additional species, e.g., a polyvalent scaffold (e.g., into a FRET pair), conjugated to a nucleic acid or to a linker.
Figure 8A:
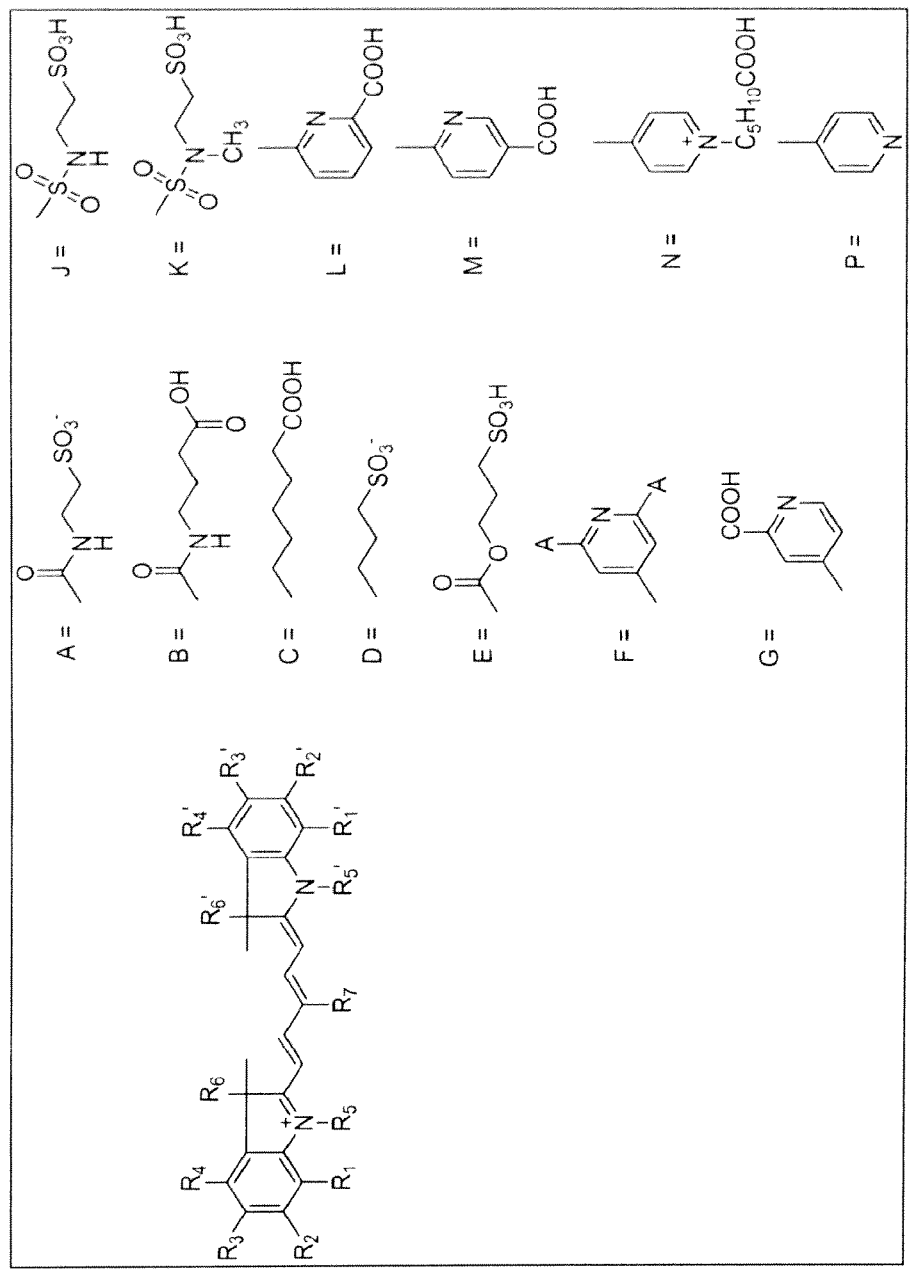
FIG. 8(a) is a generic structure of exemplary precursors of the dye components of the conjugates of the invention and of substituents on these precursors. Once incorporated into a conjugate of the invention, the conjugated dyes can be further conjugated to one or more additional species, e.g., a polyvalent scaffold (e.g., into a FRET pair), conjugated to a nucleic acid or to a linker.
Figure 9A:
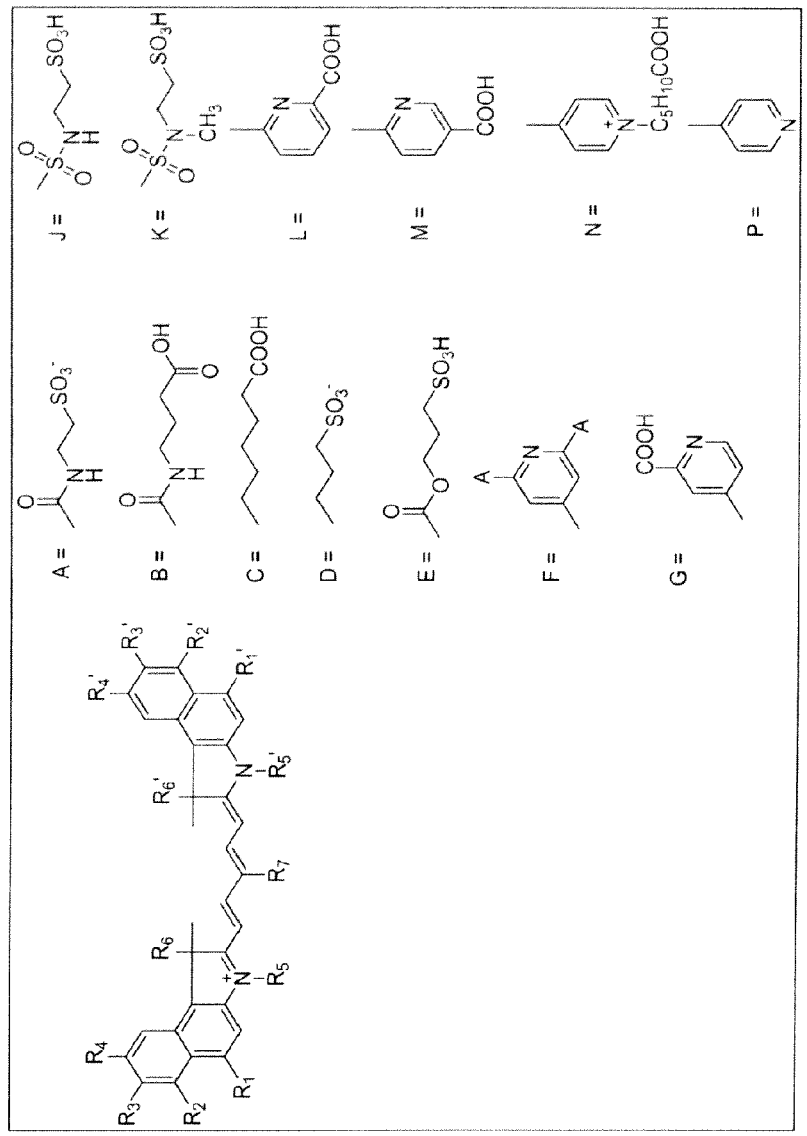
FIG. 9(a) is a generic structure of exemplary precursors of the dye components of the conjugates of the invention and of substituents on these precursors. Once incorporated into a conjugate of the invention, the conjugated dyes can be further conjugated to one or more additional species, e.g., a polyvalent scaffold (e.g., into a FRET pair), conjugated to a nucleic acid or to a linker.
Figure 10A:
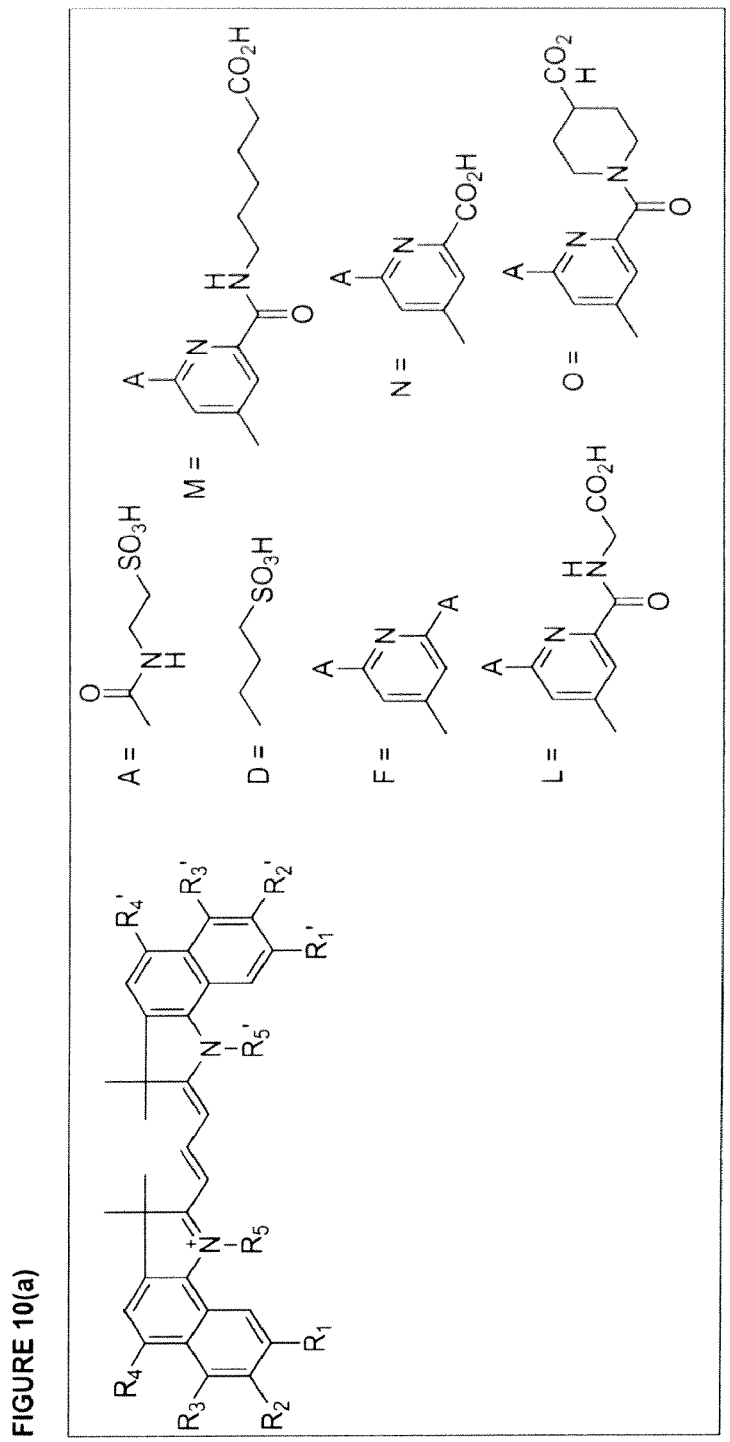
FIG. 10(a) is a generic structure of exemplary precursors of the dye components of the conjugates of the invention and of substituents on these precursors. Once incorporated into a conjugate of the invention, the conjugated dyes can be further conjugated to one or more additional species, e.g., a polyvalent scaffold (e.g., into a FRET pair), conjugated to a nucleic acid or to a linker.
Figure 11A:
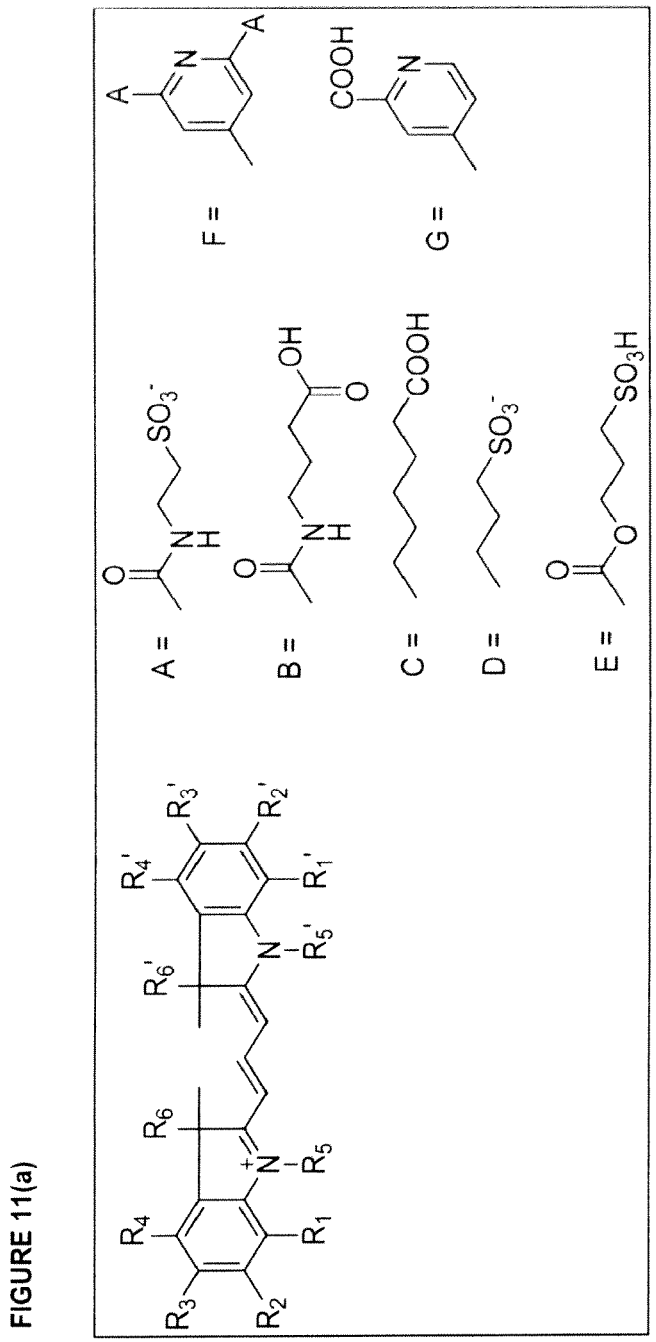
FIG. 11(a) is a generic structure of exemplary precursors of the dye components of the conjugates of the invention and of substituents on these precursors. Once incorporated into a conjugate of the invention, the conjugated dyes can be further conjugated to one or more additional species, e.g., a polyvalent scaffold (e.g., into a FRET pair), conjugated to a nucleic acid or to a linker.
Figure 12A:
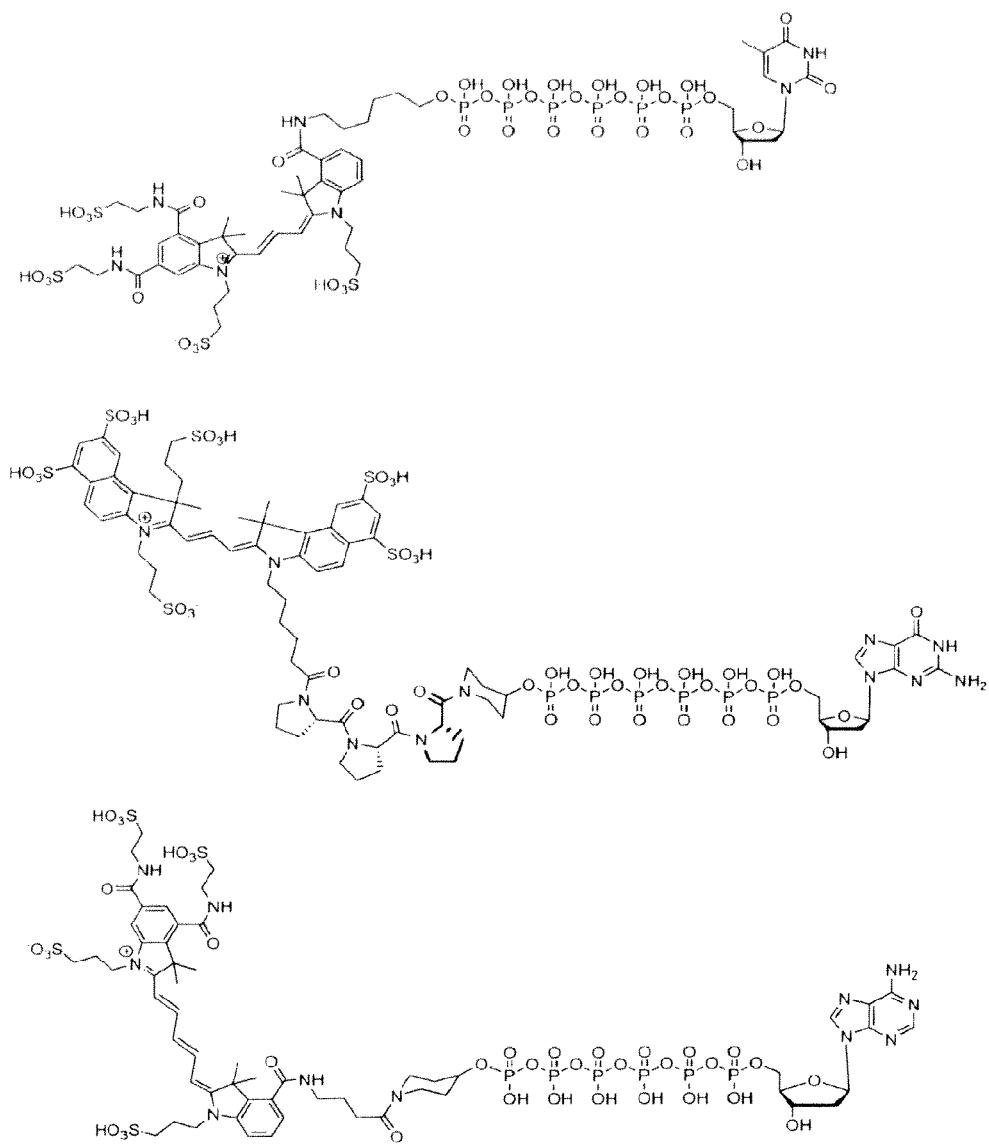
FIGS. 12(a) and 12(b) display structures of exemplary nucleic acid (polyphosphate) conjugates of the invention.
Figure 12B:
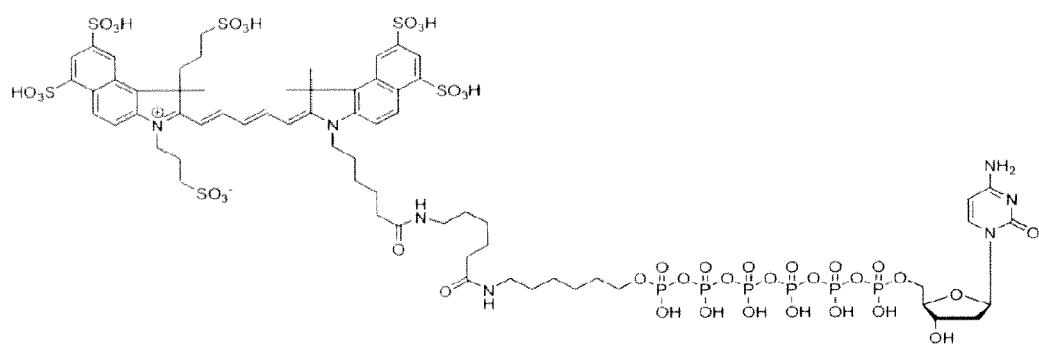
Figure 13A:
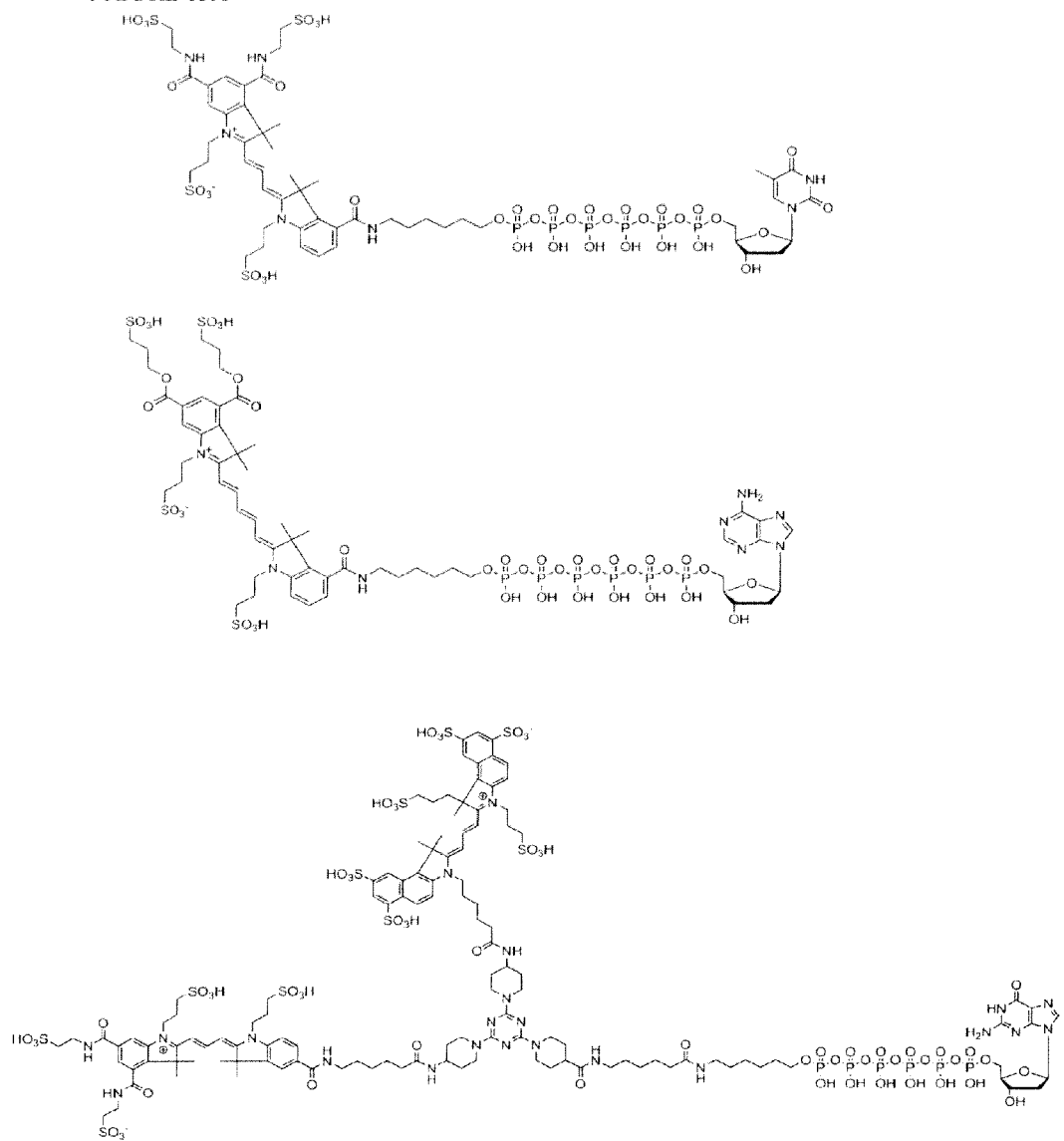
FIGS. 13(a) and 13(b) display structures of exemplary monovalent and polyvalent dye nucleic acid (polyphosphate) conjugates of the invention.
Figure 13B:
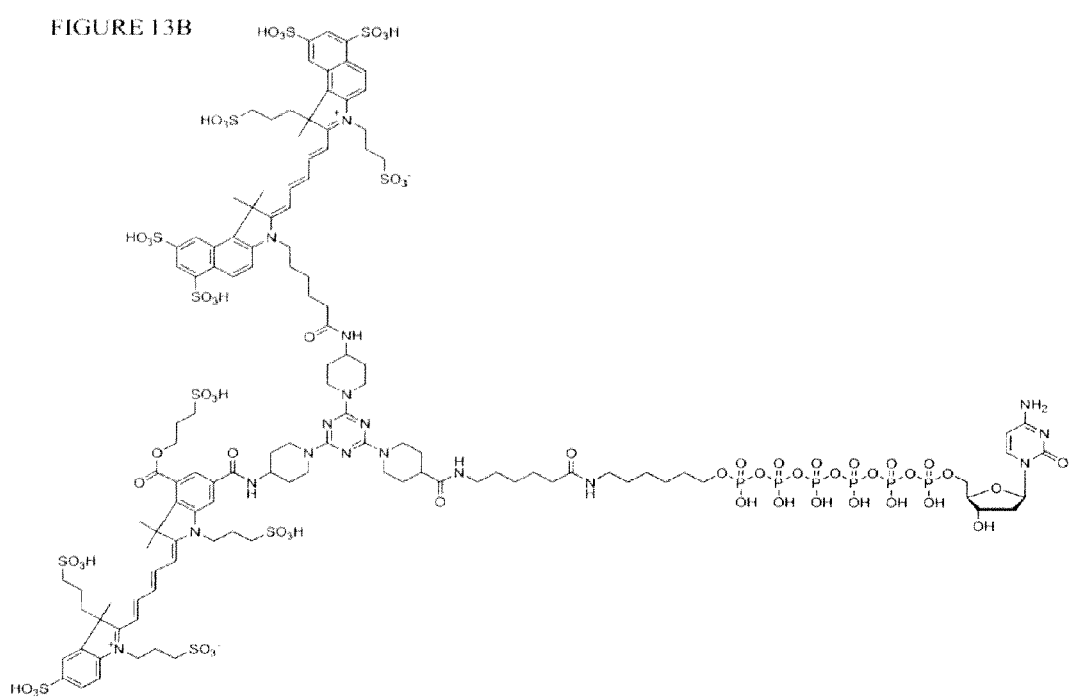

"FET", as used herein, refers to "Fluorescence Energy Transfer."

"FRET", as used herein, refers to "Fluorescence Resonance Energy Transfer." These terms are used herein to refer to both radiative and non-radiative energy transfer processes. For example, processes in which a photon is emitted and those involving long-range electron transfer are included within these terms. Throughout this specification, both of these phenomena are subsumed under the general term "donor-acceptor energy transfer."

Any of the dyes set forth herein can be a component of an FET or FRET pair as either the donor or acceptor. Conjugating a compound of the invention and a donor or acceptor fluorophore through reactive functional groups on the conjugation partners and an appropriate linker, adaptor, carrier molecule or a combination thereof is well within the abilities of those of skill in the art.

The symbol "R", as used herein, refers to moiety which is a member selected from the moieties defined in the following section, e.g., substituted or unsubstituted alkyl, substituted or unsubstituted heteroalkyl, substituted or unsubstituted aryl, substituted or unsubstituted heteroaryl, etc. as well as those groups set forth as substituents of these moieties.

As used herein, the abbreviations for the genetically encoded L-enantiomeric amino acids used in the linker constructs in the compounds of the invention are conventional and are as follows:

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |

-continued

| Amino Acid | One-Letter Symbol | Common Abbreviation |
|---|---|---|
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Definitions

Where chemical moieties are specified by their conventional chemical formulae, written from left to right, they optionally equally encompass the moiety which would result from writing the structure from right to left, e.g., —CH$_2$O— is intended to also recite —OCH$_2$—; —NHS(O)$_2$— is also intended to optionally represent. —S(O)$_2$HN—, etc. Moreover, where compounds can be represented as free acids or free bases or salts thereof, the representation of a particular form, e.g., carboxylic or sulfonic acid, also discloses the other form, e.g., the deprotonated salt form, e.g., the carboxylate or sulfonate salt. Appropriate counterions for salts are well-known in the art, and the choice of a particular counterion for a salt of the invention is well within the abilities of those of skill in the art. Similarly, where the salt is disclosed, this structure also discloses the compound in a free acid or free base form. Methods of making salts and free acids and free bases are well-known in the art.

"Amino Acid," as used herein refers to the genus encompassing hydrophilic amino acids, acidic amino acids, basic amino acids, polar amino acids, hydrophobic amino acids, aromatic amino acids, non-polar amino acids and aliphatic amino acids, including the genus and the species therein. The peptide linkers of the invention are formed from such amino acids. Amino acids also encompass amino-carboxylic acid species other than α-amino acids, e.g., aminobutyric acid (aba), aminohexanoic acid (aha), aminomethylbenzoic acid (amb) etc.

"Hydrophilic Amino Acid" refers to an amino acid exhibiting a hydrophobicity of less than zero according to the normalized consensus hydrophobicity scale of Eisenberg et al., 1984, J. Mol. Biol. 179: 125-142. Genetically encoded hydrophilic amino acids include Thr (T), Ser (S), His (H), Glu (E), Asn (N), Gln (Q), Asp (D), Lys (K) and Arg I.

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

"Basic Amino Acid" refers to a hydrophilic amino acid having a side chain pK value of greater than 7. Basic amino acids typically have positively charged side chains at physiological pH due to association with hydronium ion. Genetically encoded basic amino acids include His (H), Arg I and Lys (K).

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q), Ser (S) and Thr (T).

"Hydrophobic Amino Acid" refers to an amino acid exhibiting a hydrophobicity of greater than zero according to the normalized consensus hydrophobicity scale of Eisenberg, 1984, J. Mol. Biol. 179:125-142. Exemplary hydrophobic amino acids include Ile (I), Phe (F), Val (V), Leu (L), Trp (W), Met (M), Ala (A), Gly (G), Tyr (Y), Pro (P), and proline analogues.

"Aromatic Amino Acid" refers to a hydrophobic amino acid with a side chain having at least one aromatic or heteroaromatic ring. The aromatic or heteroaromatic ring may contain one or more substituents such as —OH, —SH, —CN, —F, —Cl, —Br, —I, —NO$_2$, —NO, —NH$_2$, —NHR, —NRR, —C (O)R, —C(O)OH, —C(O)OR, —C(O)NH$_2$, —C(O)NHR, —C(O)NRR and the like where each R is independently (C$_1$-C$_6$) alkyl, substituted (C$_1$-C$_6$) alkyl, (C$_1$-C$_6$) alkenyl, substituted (C$_1$-C$_6$) alkenyl, (C$_1$-C$_6$) alkynyl, substituted (C$_1$-C$_6$) alkynyl, (C$_1$-C$_{21}$)) aryl, substituted (C$_5$-C$_{20}$) aryl, (C$_6$-C$_{26}$) alkaryl, substituted (C$_6$-C$_{26}$) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe (F), Tyr (Y) and Trp (W).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G) and Ala (A).

"Aliphatic Amino Acid" refers to a hydrophobic amino acid having an aliphatic hydrocarbon side chain. Genetically encoded aliphatic amino acids include Ala (A), Val (V), Leu (L) and Ile (I).

Peptide linkers in the compounds of the invention are formed from amino acids linked by one or more peptide bond. The linkers are formed from oligomers of the same amino acid or different amino acids.

An "Adaptor" is a moiety that is at least bivalent. Exemplary adaptors are bound to a nucleic acid and a fluorescent dye, either directly or through a linker. The adaptor can also be bound to a second fluorescent dye, to a polyvalent scaffold or to a second nucleic acid. When the adaptor is bound to a second dye, either directly or through a polyvalent scaffold, the resulting conjugate is optionally a FRET pair. The adaptor is preferably bound to the phosphorus atom of a phosphate, phosphate ester or polyphosphate moiety of a nucleic acid. In exemplary embodiments, the adaptor is bound through an amide moiety to the dye or to the linker of the linker-dye cassette. The amide moiety is formed between an amine on the adaptor and a carboxyl group on the dye or the linker precursor.

"Cyanine," as used herein, refers to aryl and heteroaryl polymethine dyes such as those based upon the cyanine, merocyanine, styryl and oxonol ring.

As used herein, "nucleic acid" means any natural or non-natural nucleoside, or nucleotide and oligomers and polymers thereof, e.g., DNA, RNA, single-stranded, double-stranded, triple-stranded or more highly aggregated hybridization motifs, and any chemical modifications thereof. Modifications include, but are not limited to, conjugation into a compound of the invention. Further modifications include those providing the nucleic acid with a group that incorporates additional charge, polarizability, hydrogen bonding, electrostatic interaction, fluxionality or functionality to the nucleic acid. Exemplary modifications include the attachment to the nucleic acid, at any position, of one or more hydrophobic or hydrophilic moieties, minor groove binders, intercalating agents, quenchers, chelating agents, metal chelates, solid supports, and other groups that are usefully attached to nucleic acids. Exemplary nucleic acids of the invention include one or more dye moiety of the invention bound thereto.

Exemplary modified nucleic acids include, but are not limited to, peptide nucleic acids (PNAs), those with phosphodiester group modifications (e.g., replacement of O$^-$ with OR, NR, or SR), 2'-, 3'- and 5'-position sugar modifications, modifications to the nucleobase moiety, e.g., 5-position pyrimidine modifications, 8-position purine modifications, modifications at exocyclic amines, substitution of 4-thiouridine, substitution of 5-bromo or 5-iodo-uracil; backbone modifications, i.e., substitution of $P(O)O_3$ with another moiety, methylations, unusual base-pairing combinations such as the isobases, isocytidine and isoguanidine and the like. Nucleic acids can also include non-natural bases, e.g., nitroindole. Non-natural nucleobases include bases that are modified with a compound of the invention or a linker-compound of the invention construct, a minor groove binder, an intercalating agent, a hybridization enhancer, a chelating agent, a metal chelate, a quencher, a fluorophore, a fluorogenic compound, etc. Modifications within the scope of "nucleic acid" also include 3' and 5' modifications with one or more of the species described above.

The nucleic acid can comprise DNA, RNA or chimeric mixtures or derivatives or modified versions thereof. Both the probe and target nucleic acid can be present as a single strand, duplex, triplex, etc. Moreover, as discussed above, the nucleic acid can be modified at the nucleobase moiety, sugar moiety, or phosphate backbone with other groups such as radioactive labels, minor groove binders, intercalating agents, donor and/or acceptor moieties and the like.

In addition to the naturally occurring "nucleobases," adenine, cytosine, guanine and thymine, nucleic acid components of the compounds of the invention optionally include modified bases. These components can also include modified sugars. For example, the nucleic acid can comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N$^6$-isopentenyladenine, 1-methylguanine, 1-methylinosine, 2,2-dimethylguanine, 2-methyladenine, 2-methylguanine, 3-methylcytosine, 5-methylcytosine, N$^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, nitroindole, and 2,6-diaminopurine. The dye of the invention or another probe component can be attached to the modified base.

In another embodiment, the nucleic acid comprises at least one modified sugar moiety selected from the group including, but not limited to, arabinose, 2-fluoroarabinose, xylulose, and hexose. The dye or another probe component can be attached to the modified sugar moiety.

In yet another embodiment, the nucleic acid comprises at least one modified phosphate backbone selected from the group including, but not limited to, a peptide nucleic acid hybrid, a phosphorothioate, a phosphorodithioate, a phosphoramidothioate, a phosphoramidate, a phosphordiamidate, a methylphosphonate, an alkyl phosphotriester, and a formacetal or analog thereof. The dye or another probe component can be attached to the modified phosphate backbone.

"Nucleic acid" also includes a component of a conjugte with one or more modified phosphate bridges (e.g., $P(O)O_3$) by conjugating a linker-dye conjugate of the invention to the nucleic acid, e.g., replacing or derivatizing an oxygen of the bridge) with a compound of the invention or a species that includes a compound of the invention attached to an adaptor. For example, "nucleic acid" also refers to species in which, rather than the $P(O)(O^-)O_2$ moiety of a naturally occurring nucleic acid, includes the moiety ROP(O)(O—)O, in which R is a dye-linker conjugate of the invention, an adaptor, a linker-adaptor cassette or a fluorescent dye-linker-adaptor cassette. An exemplary linker is an amino acid or peptide linker of the invention. In various embodiments, one oxygen of this structure is bound to the phosphorus atom of a $P(O)(O^-)O_2$, such that the nucleic acid includes two or more phosphate moieties bound to each other.

Further exemplary nucleic acids of the invention include a nucleotide having a polyphosphate moiety, e.g., pyrophosphate or a higher homologue, such as the 3-mer, 4-mer, 5-mer, 6-mer, 7-mer, 8-mer and the like. Exemplary nucleic acids include such a polyphosphate moiety bonded to the 5'-oxygen of a nucleoside. In addition to the attached polyphosphate moiety can include a modified phosphate bridge, such as those exemplified herein. In an exemplary embodiment, the modified phosphate bridge is modified with an adaptor, a linker dye conjugate, a linker-adaptor cassette or a fluorescent dye-linker-adaptor cassette. In an exemplary embodiment, the linker is an amino acid or peptide linker such as those set forth herein. Examples of some nucleic acids finding use in the present invention are set forth in Published U.S. Patent Application Nos. 2003/0124576 and 2007/0072196 as well as U.S. Pat. Nos. 7,223,541 and 7,052,839, the full disclosures of which are incorporated herein by reference for all purposes.

Furthermore, "nucleic acid" includes those species in which one or more internucleotide bridge does not include phosphorus: the bridge being optionally modified with a compound of the invention or a linker-dye construct of the invention. An exemplary bridge includes a substituted or unsubstituted alkyl or substituted or unsubstituted heteroalkyl moiety in which a carbon atom is the locus for the interconnection of two nucleoside sugar residues (or linker moieties attached thereto) and a linker-dye construct of the invention. The discussion above is not limited to moieties that include a carbon atom as the point of attachment; the locus can also be another appropriate linking atom, such as nitrogen or another atom.

Phosphodiester linked nucleic acids of the invention can be synthesized by standard methods known in the art, e.g. by use of an automated DNA synthesizer using commercially available amidite chemistries (Ozaki et al., *Nucleic Acids Research*, 20: 5205-5214 (1992); Agrawal et al., *Nucleic Acids Research*, 18: 5419-5423 (1990); Beaucage et al., *Tetrahedron*, 48: 2223-2311 (1992); Molko et al., U.S. Pat. No. 4,980,460; Koster et al., U.S. Pat. No. 4,725,677; Caruthers et al., U.S. Pat. Nos. 4,415,732; 4,458,066; and 4,973,679). Nucleic acids bearing modified phosphodiester linking groups can be synthesized by methods known in the art. For example, phosphorothioate nucleic acids may be synthesized by the method of Stein et al. (*Nucl. Acids Res.*

16:3209 (1988)), methylphosphonate nucleic acids can be prepared by use of controlled pore glass polymer supports (Sarin et al., *Proc. Natl. Acad. Sci. U.S.A.* 85:7448-7451 (1988)). Other methods of synthesizing both phosphodiester- and modified phosphodiester-linked nucleic acids will be apparent to those of skill in the art.

As used herein, "quenching group" refers to any fluorescence-modifying group of the invention that can attenuate, at least partly, the energy (e.g., light) emitted by a fluorescent dye. This attenuation is referred to herein as "quenching". Hence, irradiation of the fluorescent dye in the presence of the quenching group leads to an emission signal from the fluorescent dye that is less intense than expected, or even completely absent. Quenching typically occurs through energy transfer between the fluorescent dye and the quenching group.

"Carrier molecule," as used herein refers to any molecule to which a compound of the invention, or a conjugate incorporating a compound of the invention, is attached. Representative carrier molecules include a nucleic acid, protein (e.g., enzyme, antibody), glycoprotein, peptide, saccharide (e.g., mono-, oligo-, and poly-saccharides), hormone, receptor, antigen, substrate, metabolite, transition state analog, cofactor, inhibitor, drug, dye, nutrient, growth factor, etc., without limitation. "Carrier molecule" also refers to species that might not be considered to fall within the classical definition of "a molecule," e.g., solid support (e.g., synthesis support, chromatographic support, membrane), virus and microorganism. An exemplary carrier molecule of use in the present invention is a polyphosphate nucleic acid. Exemplary conjugates between a fluorescent dye and a polyphosphate nucleic acid are conjugated by covalent binding of the dye to the linker and hence to the nucleic acid, or covalent binding of the dye to a linker and the linker to the adaptor—the adaptor is conjugated to the nucleic acid. Alternatively, the dye is bound to a linker, which is bound to an adaptor, which is bound to the nucleic acid. In an exemplary embodiment, the adaptor is bound to the polyphosphate moiety through a phosphodiester bond. In an exemplary embodiment, the adaptor (or linker) is attached to the dye through a bond formed with an activated derivative of a carboxyl moiety on the dye. In various embodiments, the bond is an amide bond.

"Activated derivatives of carboxyl moieties," and equivalent species, refers to moiety on a precursor component of a conjugate of the invention (e.g., dye, adaptor, linker, polyvalent moiety) having an oxygen-containing, or other, leaving group, e.g., an active ester, acyl halide, acyl imidazolide, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include mono-, di- and multivalent radicals, having the number of carbon atoms designated (i.e., $C_1$-$C_{10}$ means one to ten carbons). Examples of saturated alkyl radicals include, but are not limited to, groups such as methyl, methylene, ethyl, ethylene, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, includes "alkylene" and, optionally, those derivatives of alkyl defined in more detail below, such as "heteroalkyl."

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, P and S, and wherein the nitrogen and sulfur atoms may optionally be oxidized and the nitrogen heteroatom may optionally be quaternized. The heteroatom(s) O, N, S, P and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Also included are di- and multivalent species such as "cycloalkylene." Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, species such as trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Also included are di- and multi-valent linker species, such as "arylene." Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxyl)propyl, and the like).

Each of the above terms (e.g., "alkyl," "heteroalkyl," "aryl" and "heteroaryl") include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', SO$_3$R', —NR'—C(O)NR"R''', —NR"C(O)$_2$R', —NR—C(NR'R"R''')=NR''', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. Accordingly, from the above discussion of substituents, one of skill in the art will understand that the terms "substituted alkyl" and "heteroalkyl" are meant to include groups that have carbon atoms bound to groups other than hydrogen atoms, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

The substituents set forth in the paragraph above are referred to herein as "alkyl group substituents."

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R' are preferably independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R''' and R'''' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

The substituents set forth in the two paragraphs above are referred to herein as "aryl group substituents."

"Analyte", "target", "substance to be assayed", and "target species," as utilized herein refer to the species of interest in an assay mixture. The terms refer to a substance, which is detected qualitatively or quantitatively using a material, process or device of the present invention. Examples of such substances include cells and portions thereof, enzymes, antibodies, antibody fragments and other biomolecules, e.g., antigens, polypeptides, glycoproteins, polysaccharides, complex glycolipids, nucleic acids, effector molecules, receptor molecules, enzymes, inhibitors and the like and drugs, pesticides, herbicides, agents of war and other bioactive agents.

More illustratively, such substances include, but are not limited to, tumor markers such as α-fetoprotein, carcinoembryonic antigen (CEA), CA 125, CA 19-9 and the like; various proteins, glycoproteins and complex glycolipids such as β$_2$-microglobulin (β$_2$ m), ferritin and the like; various hormones such as estradiol (E$_2$), estriol (E$_3$), human chorionic gonadotropin (hCG), luteinizing hormone (LH), human placental lactogen (hPL) and the like; various virus-related antigens and virus-related antibody molecules such as HBs antigen, anti-HBs antibody, HBc antigen, anti-HBc antibody, anti-HCV antibody, anti-HIV antibody and the like; various allergens and their corresponding IgE antibody molecules; narcotic drugs and medical drugs and metabolic products thereof; and nucleic acids having virus- and tumor-related polynucleotide sequences.

The term, "assay mixture," refers to a mixture that includes the analyte and other components. The other components are, for example, diluents, buffers, detergents, and contaminating species, debris and the like that are found mixed with the target. Illustrative examples include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, extractants, solvents and the like.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like. Peptides can have mixed sequences of be composed of a single amino acid, e.g., poly(lysine). An exemplary polysaccharide is poly(sialic acid). An exemplary poly(ether) is poly(ethylene glycol), e.g., m-PEG. Poly (ethylene imine) is an exemplary polyamine, and poly (acrylic) acid is a representative poly(carboxylic acid).

The polymer backbone of the water-soluble polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly(ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly (ethylene glycol) can be represented in general form as R(-PEG-OH).sub.m in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as polypropylene glycol ("PPG"), copolymers of ethylene glycol and propylene glycol and the like, poly(oxyethylated polyol), poly(olefinic alcohol), poly(vinylpyrrolidone), poly (hydroxypropylmethacrylamide), poly(α-hydroxy acid), poly(vinyl alcohol), polyphosphazene, polyoxazoline, poly (N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of from about 100 Da to about 100,000 Da, often from about 6,000 Da to about 80,000 Da.

The term PEG or poly(ethylene glycol) is intended to be inclusive and not exclusive. The term PEG includes poly (ethylene glycol) in any of its forms, including alkoxy PEG, difunctional PEG, multiarmed PEG, forked PEG, branched PEG, pendent PEG (i.e., PEG or related polymers having one or more functional groups pendent to the polymer backbone), or PEG with degradable linkages therein.

The PEG backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as $R(-PEG-OH)_m$ in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

An "Adaptor" is a moiety that is at least bivalent and which is bound to a linker bound to a dye or it is bound directly to the dye. The adaptor also forms a bond with a second dye, polyvalent scaffold or to a nucleic acid. When the adaptor is bound to another dye, either directly or through a polyvalent scaffold, the resulting conjugate is optionally a FRET pair. When the adaptor is bound to a nucleic acid, it is preferably bound to the phosphorus atom of a phosphate, phosphate ester or polyphosphate moiety. In exemplary embodiments, the adaptor is bound through an amide moiety to the dye. The amide moiety is formed between an amine on the adaptor and a carboxyl group on the dye.

"Readlength" is the number of bases the DNA polymerase enzyme at the bottom of the ZMW goes through during sequencing. A longer readlength is desirable. Readlength depends, inter alia, on how fast the enzyme can incorporate fluorescent nucleotides of different colors (monitored this by observing pulse widths and interpulse distances). Readlength also depends on how long the enzyme can incorporate analog without being photodamaged (damaged via undesired interactions with fluorescent nucleotides excited by light).

"Accuracy" is how precise a nucleotide with a base of a particular type can be identified as the polymerase enzyme goes through incorporation of fluorescent nucleotides. The base is identified by a pulse of a selected wavelength upon incorporation of the nucleotide incorporating that base. Robust applications include precise base calling. Accuracy can be diminished by one or more of extra pulses, missing pulses and miscalled pulses.

"Extra pulses"—when a pulse is called and there is no nucleotide incorporation event. Extra pulses may be caused by branching (when enzyme samples the fluorescent analog but does not incorporate), sticks (non-specific interactions of fluorescent nucleotides with enzyme outside of incorporating site and surface of ZMW), photophysical blinking (photophysically unstable behavior of fluorescent nucleotides during incorporation resulting in splitting of fluorescent signal).

"Missing pulses"—when a pulse is not called when there is in fact a nucletided incorporation event. Missing pulses may be caused by insufficient brightness of fluorescent nucleotides, low purity of fluorescent nucleotides, or polymerase going too fast to detect all pulses.

"Miscalled pulses"—when pulse of different kind is called instead of correct one. Miscalls may be caused by insufficient spectral separation between fluorescent nucleotides of different colors, photophysical instability of our fluorescent nucleotides, low intensity or high background of fluorescent nucleotide signal.

Introduction

Residing in the field of fluorescent labels, the present invention provides benefits of particular note. Fluorescent labels have the advantage of requiring few precautions in handling, and being amenable to high-throughput visualization techniques (optical analysis including digitization of the image for analysis in an integrated system comprising a computer). Exemplary labels exhibit one or more of the following characteristics: high sensitivity, high stability, low background, low environmental sensitivity and high specificity in labeling.

Amongst the advantages provided by the present invention are included advances in the field of monitoring enzymatic reactions. In exemplary embodiments, the linker component of compounds of the invention increases the affinity of a conjugate of the invention, which is a substrate for an enzyme, for this enzyme, reducing the $K_m$ of the reaction. In various embodiments, the Km of the reaction is reduced by at least 10%, at least 20%, at least 30%, at least 40% or at least 50% relative to the $K_m$ of the reaction with an analogous conjugate without the amino acid or peptide linker component.

The compounds, probes and methods discussed in the following sections are generally representative of the compositions of the invention and the methods in which such compositions can be used. The following discussion is intended as illustrative of selected aspects and embodiments of the present invention and it should not be interpreted as limiting the scope of the present invention.

The Embodiments
Compositions

In an exemplary embodiment, the present invention provides a fluorescent dye having the formula:

$$\{R^1\text{-}(L^1)_a\text{-}(AA)_n\}_y\text{-}(L^2)_b\text{-}X \quad (I)$$

wherein $R^1$ is a fluorescent dye moiety. AA is an amino acid. The index n is selected from the integers 1, 2, 3, 4, 5, 6, 7, 8, 9, 10, 11 and 12, and when n is two or greater, each n amino acid is independently selected and the $(AA)_n$ component is a peptide. X is a member selected from a polyvalent moiety, and a moiety including the structure:

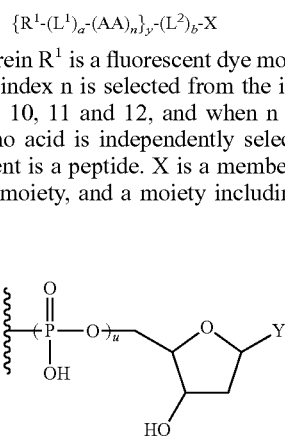

(II)

wherein Y is a nucleobase; and u is selected from the integers 1, 2, 3, 4, 5, 6, 7 and 8. The index y is selected from the integers 1, 2, 3, 4, 5, 6, 7 and 8, such that when y is 2 or greater, X is a polyvalent moiety. $L^1$ and $L^2$ are independently selected from bonds, adaptors and substituted or unsubstituted alkyl and substituted or unsubstituted heteroalkyl moieties. The index a is 0 or 1, and b is an integer selected from 0, 1, 2, 3, 4, 5, 6, 7 and 8.

In exemplary embodiments, the compound of the invention has the formula:

$$R^1\text{-}(L^1)_a\text{-}(AA)_n\text{-}(L^2)_b\text{-}X \quad (III)$$

in which the radicals and indices are as discussed herein.

In various embodiments, $L^1$ and/or $L^2$ is, or includes an adaptor component. Exemplary adaptors of use in the compounds of the invention include those selected from an alkyl amine or a nitrogen-containing heterocylic moiety, e.g., piperidine. Exemplary species include an aminoalkyl (e.g. $C_1$-$C_{10}$ aminoalkyl, e.g., $C_6$ aminoalkyl) linker, —NH$(CH_2)_g$ C(O)NH$(CH_2)_h$—, in which g and h are independently selected from the integers 0, 1, 2, 3, 4, 5, 6, 7, 8, 9, 10 or higher. Such adaptors include, without limitation:

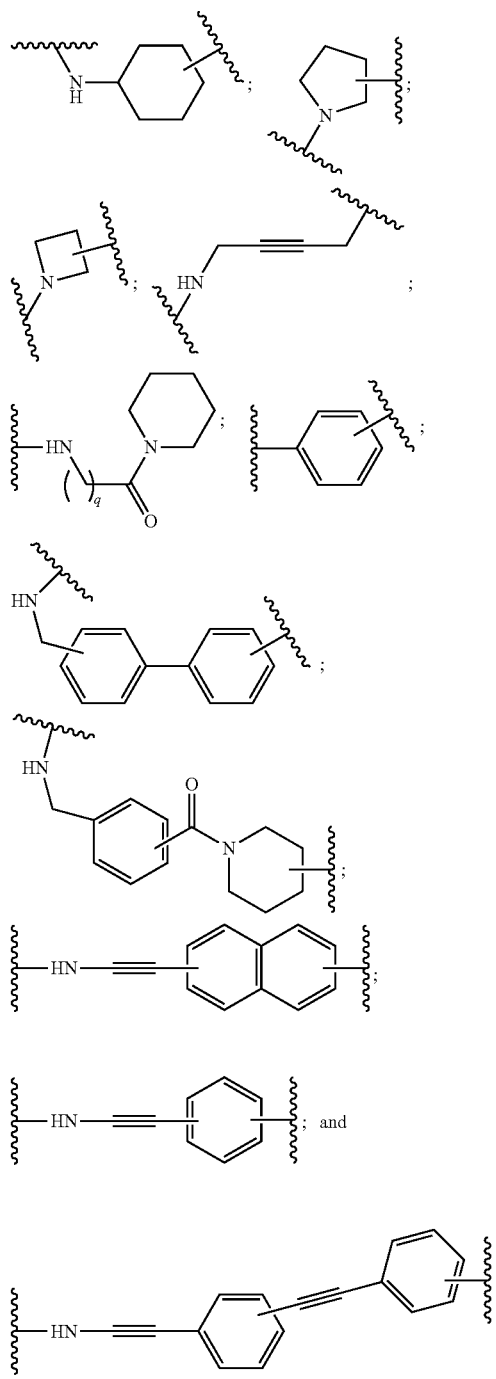

in which q is the integer 1, 2, 3, 4, 5, 6, 7, 8, 9 or 10. In various embodiments, the nitrogen of the amine moiety is bound to a fluorescent dye, a linker or a linker bound to a fluorescent dye. The other open valence is bound to the group X shown in Formula I.

In various embodiments, the adaptor has a formula selected from:
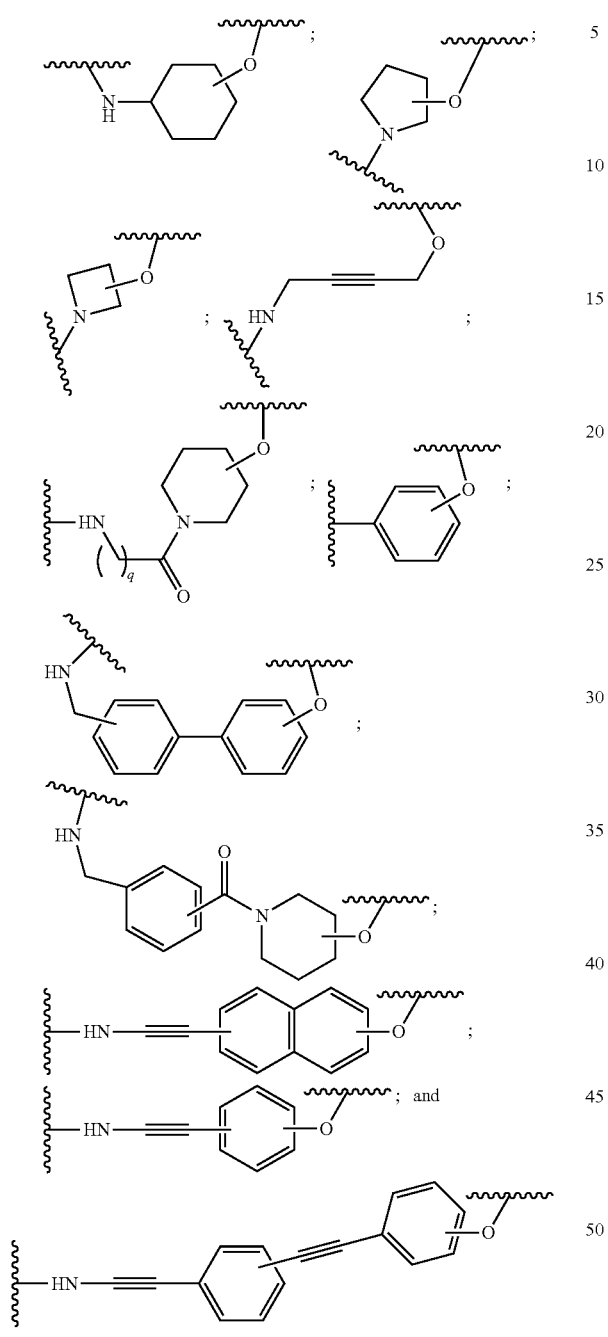
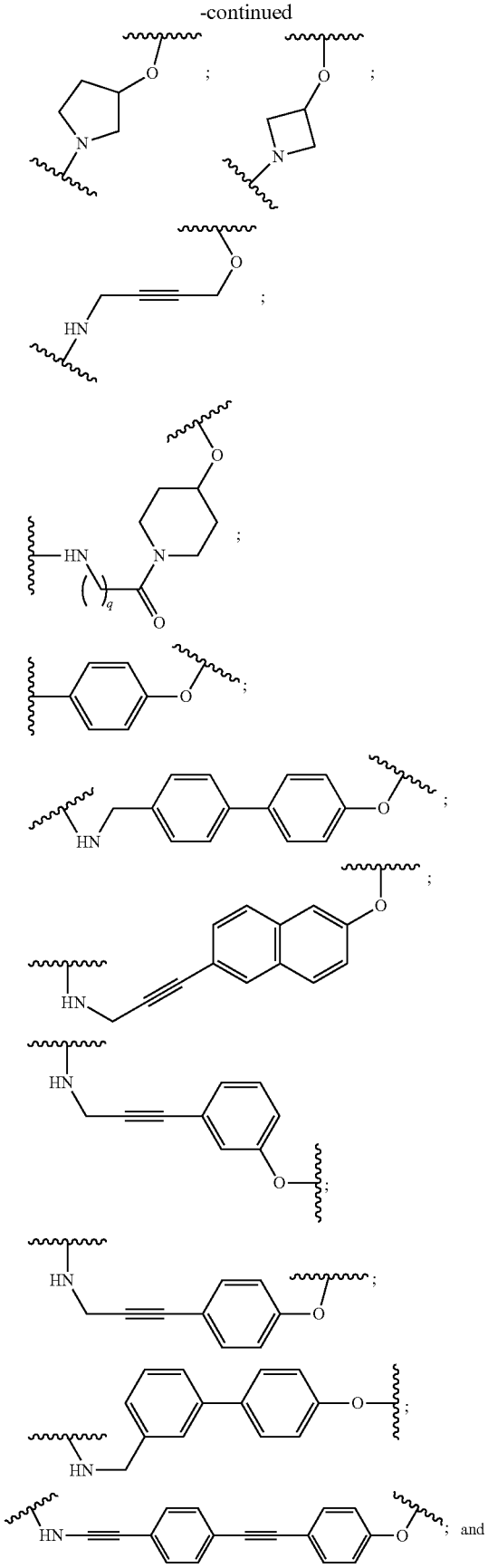
in which q is as described above. In various embodiments, the nitrogen of the amine moiety is bound to a fluorescent dye, a linker or a linker bound to a fluorescent dye. The oxygen atom is bound to the group X shown in Formula I.
In exemplary embodiments, the adaptor has a formula selected from:

-continued

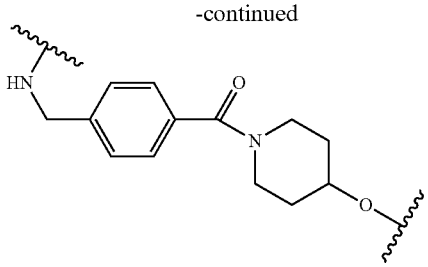

in which q is as described above. In various embodiments, the nitrogen of the amine moiety is bound to a fluorescent dye, a linker or a linker bound to a fluorescent dye. The oxygen atom is bound to the group X shown in Formula I. In each of the adaptor structures shown above, the nitrogen of the amine moiety can also be a component of the linker (e.g., derived from the amine moiety of an amino acid). In those embodiments in which an oxygen atom is shown, this oxygen atom can be bound to a phosphorus atom of a nucleic acid such as shown in Formula II. In various embodiments, an amine moiety of the linker is functionalized with a $C_1$-$C_{10}$ alkyl moiety substituted with a hydroxyl group. In various embodiments an amine moiety of the linker is functionalized with an adaptor shown above containing a hydroxyl group. In such embodiments, the hydroxyl group becomes the locus for attaching the linker and the phosphorus atom of the nucleic acid, forming a P—O bond.

In various embodiments, the invention provides nucleic acid analogues according to the formula:

A and B independently selected monocyclic, bicyclic or polycyclic aryl or heteroaryl moieties. When A and/or B is a bicyclic polycyclic moiety, two or more of the rings are optionally fused. Exemplary polycyclic moieties include indole and benzoindole. Q is a substituted or unsubstituted methine moiety (e.g., —(CH═C(R))$_c$—CH═), in which c is an integer selected from 1, 2, 3, 4, or 5 and R is an "alkyl group substituent" as defined herein. When two or more R groups are present, they are optionally joined to form a ring. Each $R^w$, $R^x$, $R^y$ and $R^z$ is independently selected from those substituents set forth in the Definitions section herein as "alkyl group substituents" and "aryl group substituents." The indices w and z are independently selected from the integers from 0 to 6. In an exemplary embodiment, at least one of $R^w$, $R^x$, $R^y$ and $R^z$ is C(O)NR°(CH$_2$)$_h$G in which G is a member selected from SO$_3$H and CO$_2$H, R° is H or substituted or unsubstituted alkyl or heteroalkyl and the index h is an integer from 1 to 20. In exemplary embodiments, at least 1, 2, 3, 4, 5, or 6 of $R^x$, $R^y$, $R^w$ and $R^z$ are alkylsulfonic acid or heteroalkylsulfonic acid and at least one of these moieties is alkylcarboxylic acid or heteroalkylcarboxylic acid. In exemplary embodiments, at least one of $R^w$, $R^x$, $R^y$ and $R^z$ includes a water-soluble polymer (e.g., poly(ethylene glycol)) component. At least one of $R^x$, $R^y$, $R^w$ and $R^z$ is $(L^1)_a$-$(AA)_n$-$(L^2)$-X as this species is defined herein.

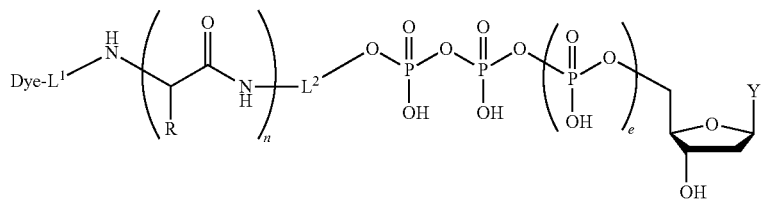

In which $L^1$, $L^2$, R, Y and e are as described above, and e is an integer selected from 1, 2, 3, 4, 5 or greater. In an exemplary embodiment, $L^1$ and or $L^2$ is or includes an adaptor. R is an amino acid side chain or a substituted amino acid side chain. In an exemplary embodiment, the linker includes at least one, at least two, at least three or more sulfocysteine moieties.

In an exemplary embodiment, the dyes conjugated into compounds of the invention are fluorescent cyanines Exemplary cyanine dyes in the compounds of the invention have the formula:

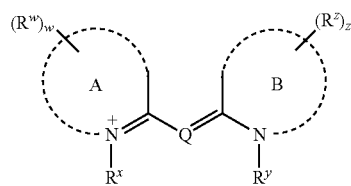

Exemplary cyanine dyes of use in forming the compounds of the invention are set forth in commonly owned U.S. Provisional Patent Application Nos. 61/377,048, titled "Cyanine Dyes", 61/377,038, titled "Assymetric Cyanine Dyes", 61/377,022, titled, "Scaffold-Based Dyes", and 61/377,004, titled, "Molecular Adaptors for Dye Conjugates". The disclosure of each of these applications is incorporated herein by reference in its entirety for all purposes.

Synthesis

Exemplary modes of synthesizing the compounds of the invention are set forth in the schemes below.

Scheme 1. Synthesis of a Phospholinked Analogs with Amino Acid Linker.

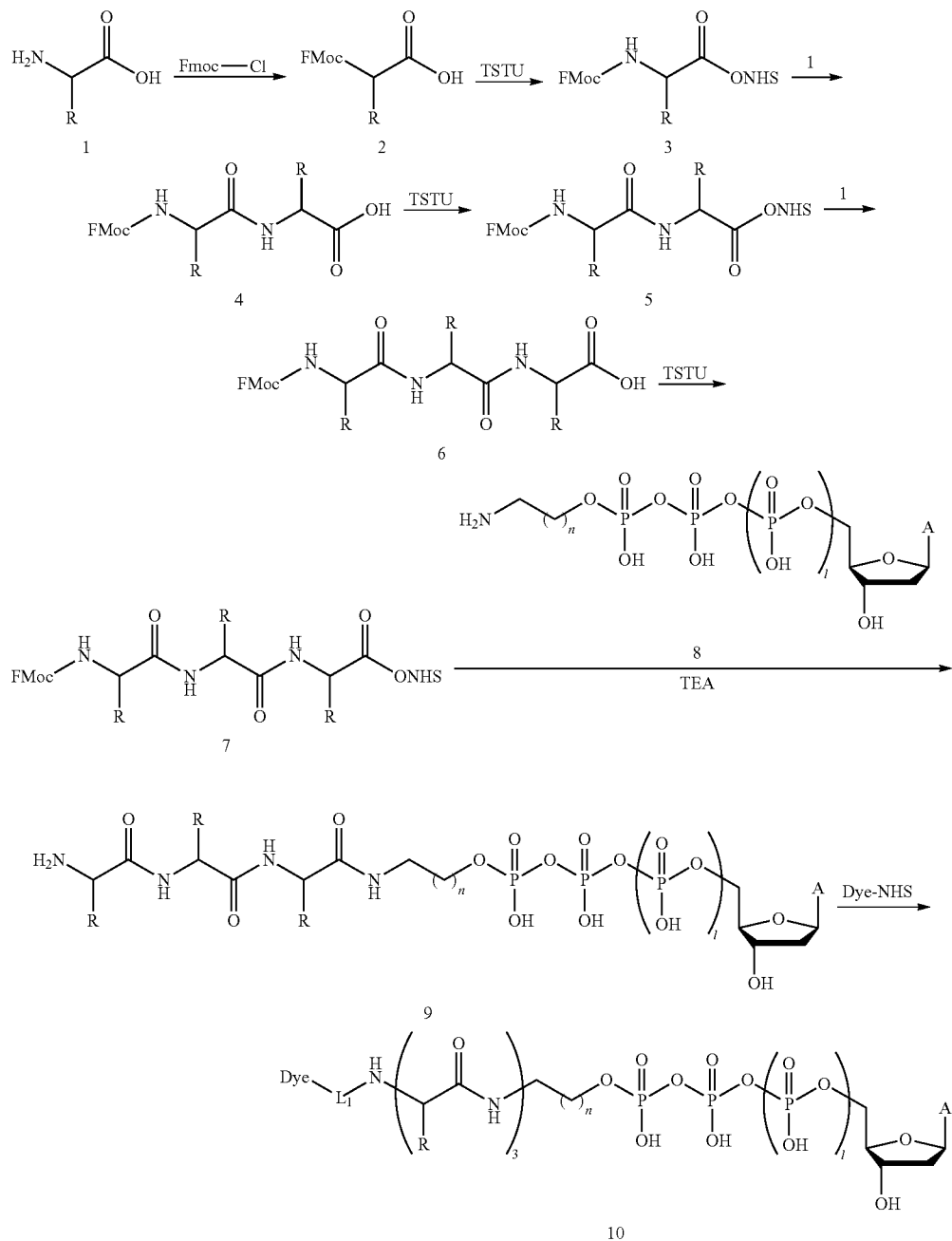

In Scheme 1, R is H or a substituted or unsubstituted amino acid side-chain. An exemplary substituted amino acid side chain is substituted with a phosphate moiety (Scheme 4). The index n is selected from the integers 0, 1, 2, 3, 4, 5, 6, 7, 8, 9, 10, 11, 12 and higher. The index 1 represents an integer selected from 0, 1, 2, 3, 4, 5, 6 and higher.

In an exemplary embodiment, illustrated by Scheme 1, amino acid 1 is N-protected and converted to N-hyrdoxy-succinimide ester 3. A second amino acid, either the same as or different from the first amino acid is coupled to the N-protected first amino acid, forming dipeptide 4. In a similar process, the dipeptide is coupled to a third amino acid, which is the same as either the first or second amino acid or different from both of these amino acids, forming tripeptide 7. This process continues until a peptide of the desired length and sequence is formed. There is no practical limitation on the sequence or length of peptides of use in the conjugates of the invention. Exemplary peptides include at least 2, 3, 4, 5, 6, 7, 8, 9, or 10 amino acids.

The peptide linker is coupled to L-NA, linker-nucleic acid (e.g., polyphosphate) cassette 9 to form fluorescent nucleic acid analogue 10. Exemplary linkers, L, of use in the conjugates of the invention include substituted or unsubstituted alkyl and substituted or unsubstituted heteroalkyl moieties.

Scheme 2. Synthesis of the Phospholinked Analogs with Lysine Linker.
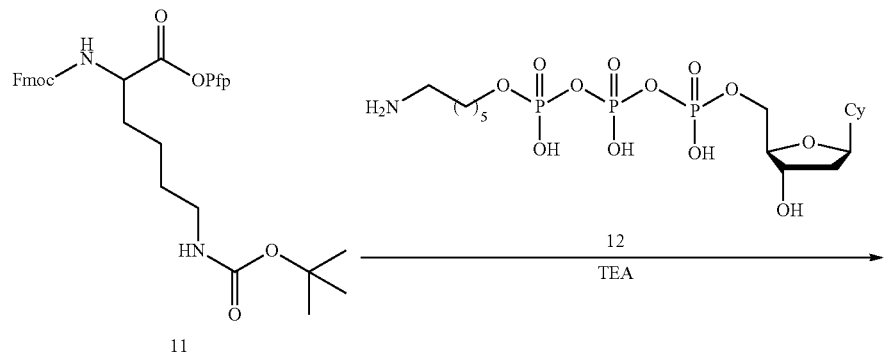
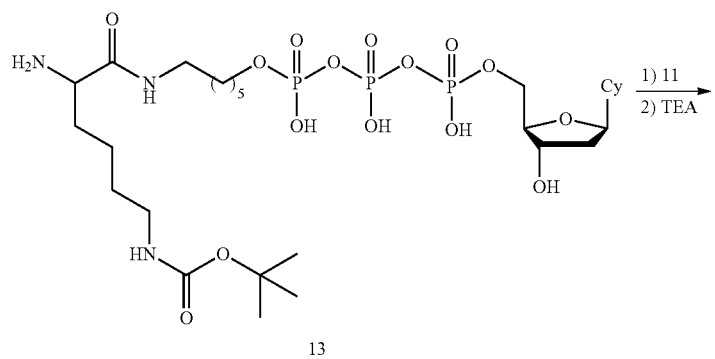
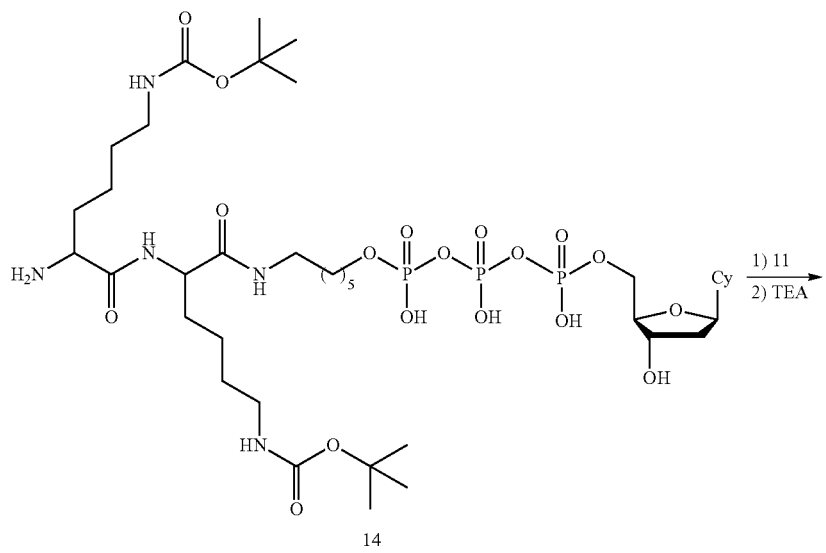

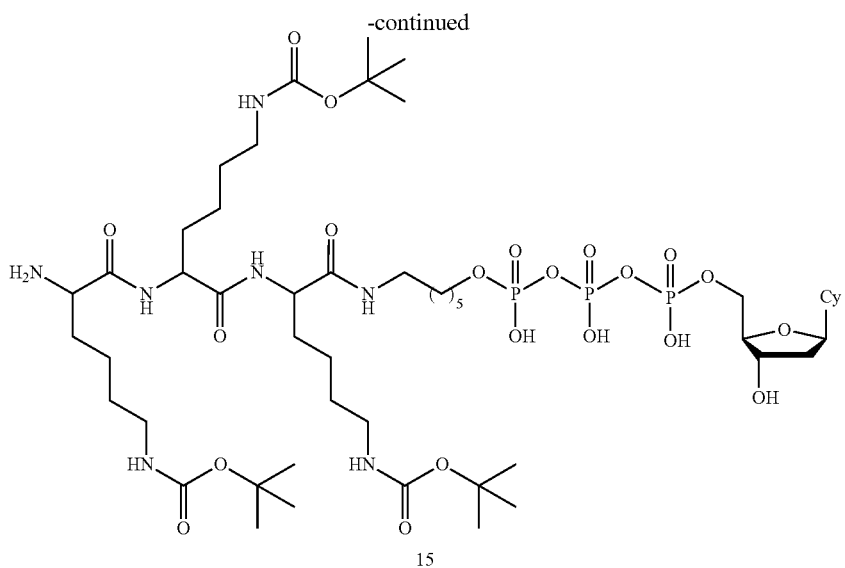
15
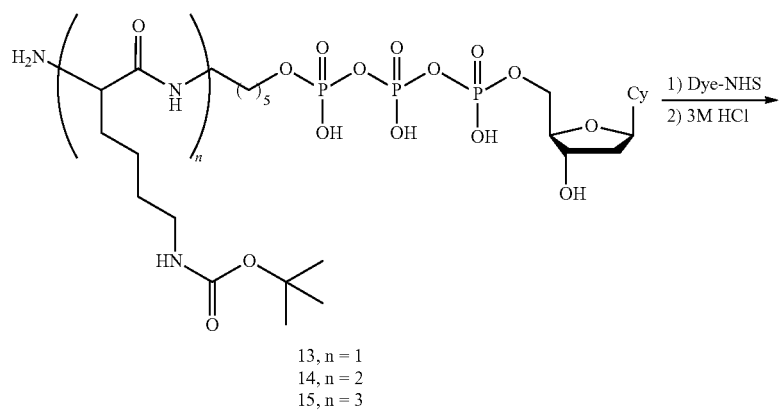
13, n = 1
14, n = 2
15, n = 3
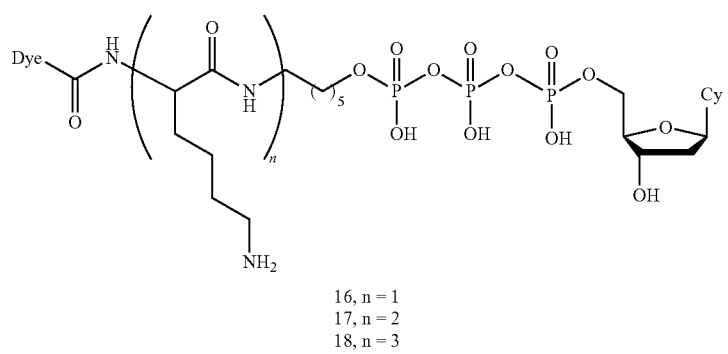
16, n = 1
17, n = 2
18, n = 3
In Scheme 2, protected, activated lysine derivative 11 is reacted with nucleic acid linker cassette 12 to form conjugate 13. A second protected, activated lysine derivative is reacted with 13, forming dipeptide 14, which is reacted with 11, forming tri-lysyl peptide 15. The amino acid and peptide are conjugated to a dye to form 16, 17 and 18.

Scheme 3. Synthesis of the Phospholinked Analogs with Glutamic Acid Linker.
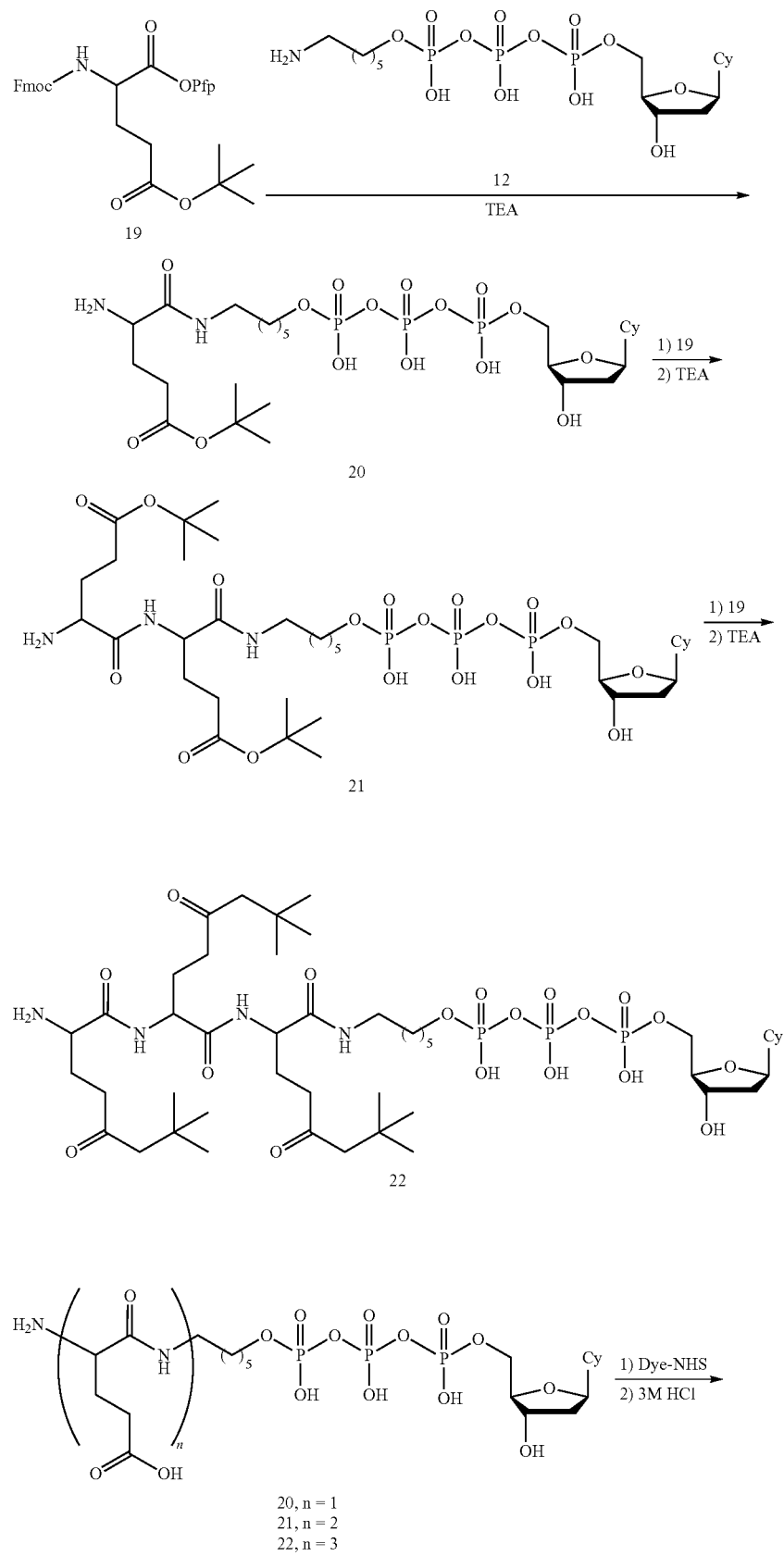

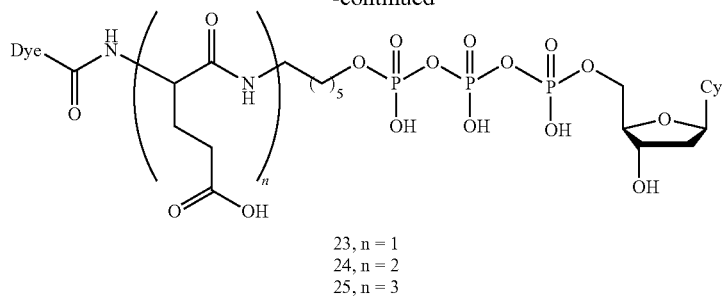
23, n = 1
24, n = 2
25, n = 3
In Scheme 3, protected, activated glutamic acid derivative 19 is reacted with linker nucleic acid cassette 12 to form 20. Compound 20 is reacted with 19 to form dipeptide 21, which is reacted with 19 to form tripeptide 22. The amino acid or peptide is reacted with a dye to form 23, 24 or 25.
Scheme 4. Synthesis of the Phospholinked Analogs with Non-Conjugated Phosphate Linker.
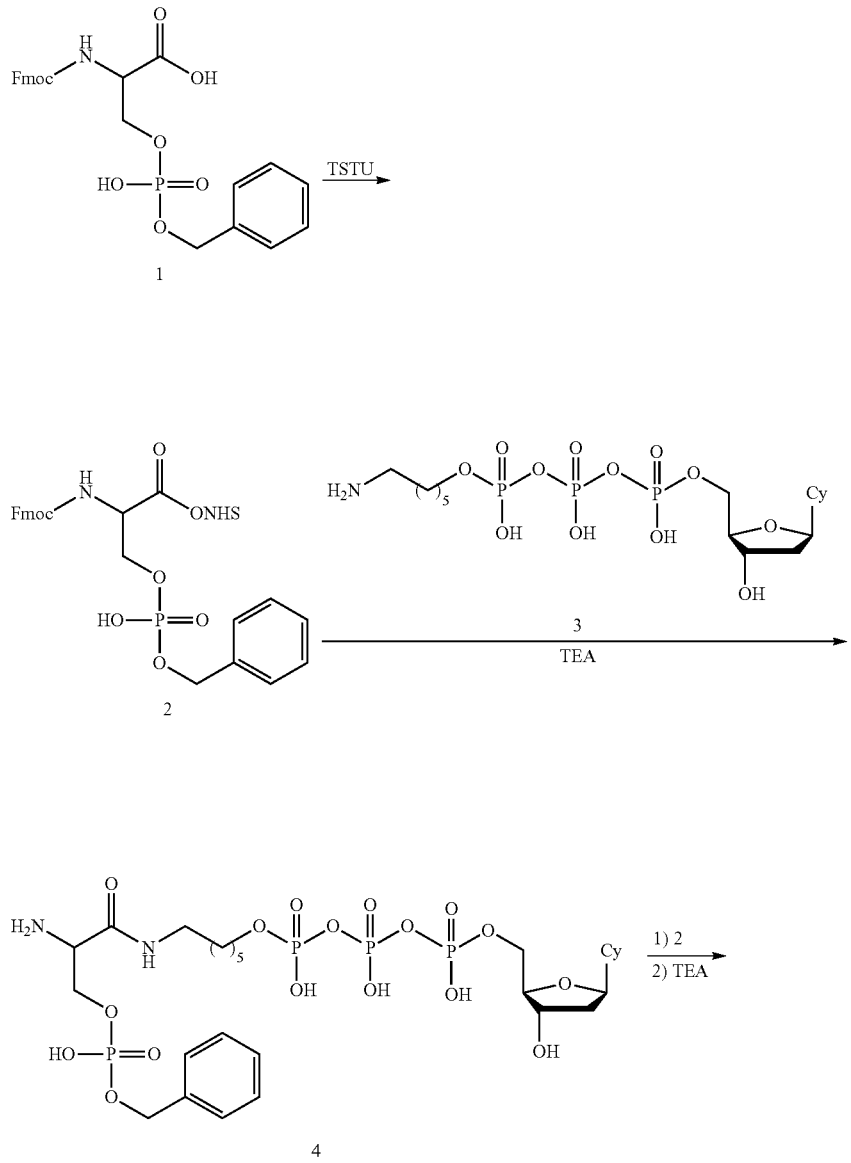

-continued

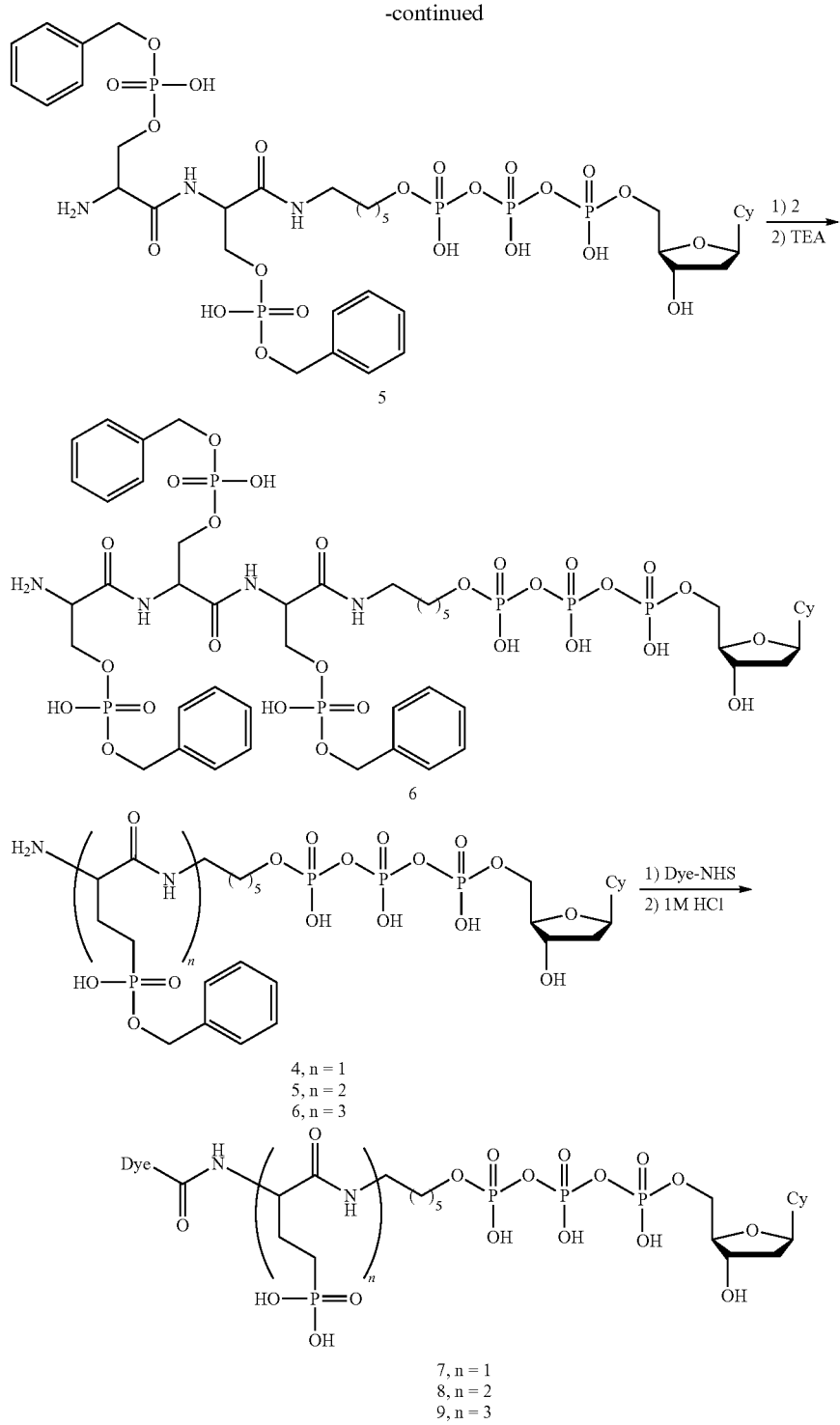

In Scheme 4, protected phosphoserine derivative 1 is converted to corresponding NHS ester 2 and coupled to nucleic acid linker cassette 3, forming conjugate 4. The amino acid is converted to dipeptide 5 by the action of 2. The dipeptide is converted to tripeptide 6 by addition of 2. The amino acid or peptide is deprotected and coupled to a dye, forming 7, 8 or 9.

As is apparent from the Schemes above, in various embodiments, the dye is bonded to the linker through an amide moiety formed by reaction of an amine moiety on a linker and an activated carboxylic acid group on the dye moiety. In an exemplary embodiment, the carboxylic acid group is a substituent on a cyanine dye.

Reactive Functional Groups

The compounds of the invention are assembled from covalent bonding reactions between precursors bearing a reactive functional group, which is a locus for formation of a covalent bond between the precursors. The precursors of compounds of the invention bear a reactive functional group, which can be located at any position on the compound.

Exemplary species include a reactive functional group attached directly to a cyanine nucleus (e.g., aryl ring or methine bridge) or to a linker attached to a component (e.g., aryl ring or methine bridge) of the dye molecule. Other molecules include a reactive functional group attached to a polyvalent moiety. An exemplary reactive functional group is attached to an alkyl or heteroalkyl moiety on the compound. When the reactive group is attached a substituted or unsubstituted alkyl or substituted or unsubstituted heteroalkyl linker moiety, the reactive group is preferably located at a terminal position of the alkyl or heteroalkyl chain. Reactive groups and classes of reactions useful in practicing the present invention are generally those that are well known in the art of bioconjugate chemistry. Currently favored classes of reactions available with reactive dye-based compounds of the invention are those proceeding under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:
(a) carboxyl groups and derivatives thereof including, but not limited to activated esters, e.g., N-hydroxysuccinimide esters, N-hydroxyphthalimide, N-hydroxybenztriazole esters, acid halides, acyl imidazoles, thioesters, p-nitrophenyl esters, alkyl, alkenyl, alkynyl and aromatic esters, activating groups used in peptide synthesis and acid halides;
(b) hydroxyl groups, which can be converted to esters, sulfonates, phosphoramidates, ethers, aldehydes, etc.
(c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups, which are capable of participating in Diels-Alder reactions such as, for example, maleimido groups;
(e) aldehyde or ketone groups, allowing derivatization via formation of carbonyl derivatives, e.g., imines, hydrazones, semicarbazones or oximes, or via such mechanisms as Grignard addition or alkyllithium addition;
(f) sulfonyl halide groups for reaction with amines, for example, to form sulfonamides;
(g) thiol groups, which can be converted to disulfides or reacted with acyl halides, for example;
(h) amine or sulfhydryl groups, which can be, for example, acylated, alkylated or oxidized;
(i) alkenes, which can undergo, for example, cycloadditions, acylation, Michael addition, etc;
(j) epoxides, which can react with, for example, amines and hydroxyl compounds; and
(k) phosphoramidites and other standard functional groups useful in nucleic acid synthesis.

The reactive functional groups can be chosen such that they do not participate in, or interfere with, the reactions necessary to assemble or utilize the reactive dye analogue. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In addition to those embodiments in which a compound of the invention is attached directly to a carrier molecule, the fluorophores can also be attached by indirect means. In this embodiment, a ligand molecule (e.g., biotin) is generally covalently bound to the probe species. The ligand then binds to another molecules (e.g., streptavidin) molecule, which is either inherently detectable or covalently bound to a signal system, such as a fluorescent compound, or an enzyme that produces a fluorescent compound by conversion of a non-fluorescent compound. Useful enzymes of interest as labels include, for example, hydrolases, particularly phosphatases, esterases and glycosidases, hydrolases, peptidases or oxidases, and peroxidases.

Polyphosphate Analogues

In an exemplary embodiment, the present invention is generally directed to compositions that comprise compounds analogous to nucleotides, and which, in various aspects are readily processible by nucleic acid processing enzymes, such as polymerases. In addition to the unexpectedly advantageous features imparted to the compounds by incorporation of dyes of novel structure, the compounds of the invention generally benefit from one or more advantages of greater stability to undesired enzymatic or other cleavage or non-specific degradation, as well as incorporation efficiencies that are better than or at least comparable to triphosphate, tetraphosphate or pentaphosphate analogs.

In various embodiments, the invention provides polyphosphate analogs of the dyes of the invention. In various embodiments, the polyphosphate analogs are polyphosphate analogue of a nucleic acid. An exemplary compound according to this motif has the general structure:

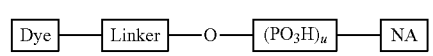

in which NA is the nucleic acid. The index u is an integer selected from 1, 2, 3, 4, 5, 6, 7, 8, 9 or 10.

In an exemplary embodiment, the polyphosphate analogue of the invention has the general structure:

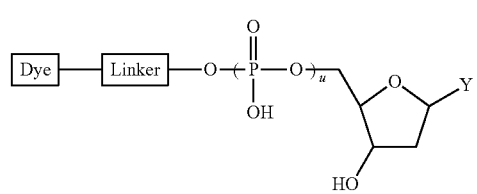

in which Y is a naturally occurring or non-natural nucleobase, and the linker includes an amino acid or peptide.

In various embodiments, the polyphosphate analogue of the invention has the general structure:

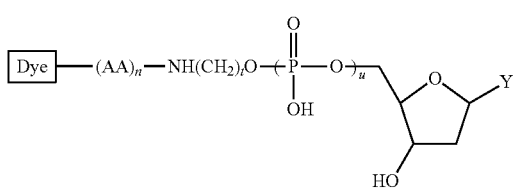

in which t is an integer selected from 1-40, more particularly, 1, 2, 3, 4, 5, 6, 7, 8, 9, 10, 11, 12, 13, 14, 15, 16, 17, 18, 19, 20 or higher. The index n is an integer selected from 1 to 20, for example 1, 2, 3, 4, 5, 6, 7, 8, 9 or 10.

In an exemplary embodiment, the polyphosphate analogue of the invention has the general structure:

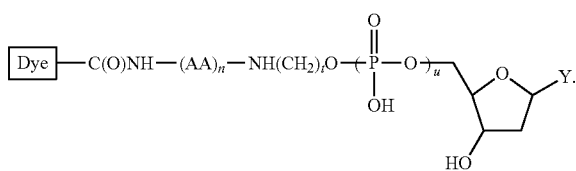

As will be apparent to those of skill in the art, the component labeled dye can be a cyanine.

In an exemplary embodiment, the dye component comprises multiple dyes bound to a common polyvalent scaffold or amplifier. Examples of such scaffold-based dyes are described in commonly owned U.S. Provisional Patent Application No. 61/377,022, the disclosure of which is incorporated in its entirety herein by reference for all purposes. The scaffold-based dyes of the invention can include FET or FRET pairs. In an exemplary embodiment, the scaffold-based dye composition includes a Cy3 and a Cy5 type of dye (e.g., of the current invention) attached to a common polyvalent scaffold or amplifier.

In various embodiments, the polyvalent moiety is a residue of a parent compound bound to one or more conjugated moiety, e.g., fluorescent dye moiety, one or more peptide linker-fluorescent dye moiety cassette, one or more nucleic acid and/or one or more linker-nucleic acid cassette. An exemplary nucleic acid of use in these embodiments is a polyphosphate moiety. Exemplary fluorescent dyes are cyanine dyes as disclosed herein and in documents incorporated herein by reference.

Exemplary parent compounds for polyvalent moieties include, for example, X is a residue derived from a member selected from triazine, perylene, piperidine, phenylalanine, diaminopropanoic acid, aspartic acid, lysine, glutamic acid, serine, aminoadipic acid, 3,5-dihydroxybenzoic acid, 2-amino-4-hydroxy-butyric acid, 4-(1-amino-1-carboxy-ethyl)-benzoic acid, piperazine-2-carboxylic acid, 4-[4,6-bis-(piperidin-4-ylamino)-[1,3,5]triazin-2-ylamino]-cyclohexanecarboxylic acid and 3-amino-3-[4-(3-amino-prop-1-ynyl)-phenyl]-propionic acid.

Those of skill in the art appreciate that, in various embodiments, the parent compound is converted to the polyvalent moiety by reaction of a reactive functional group on the parent compound with a reactive functional group on a conjugated moiety, thereby forming a covalent bond between the two reaction partners.

Probes

The invention provides probes having a dye of the invention conjugated to a carrier molecule, for example, a target species (e.g., receptor, enzyme, etc.) a ligand for a target species (e.g., nucleic acid, peptide, etc.), a small molecule (e.g., drug, pesticide, etc.), a solid support and the like. The probes can be used for in vitro and in vivo applications. Exemplary probes are those in which the dye is conjugated to the carrier molecule through an adaptor or through a linker-adaptor cassette.

Small Molecule Probes

The dyes of the invention can be used as components of small molecule probes. In a preferred design, a small molecule probe includes a dye of the invention and a second species that alters the luminescent properties of the dyes, e.g., a quencher of fluorescence. In an exemplary embodiment, an agent, such as an enzyme cleaves the dye of the invention, the quencher or both from the small molecule generating fluorescence in the system under investigation (see, for example, Zlokarnik et al., Science 279: 84-88 (1998)).

Nucleic Acid Capture Probes

In one embodiment, an immobilized nucleic acid comprising a dye of the invention is used as a capture probe. The nucleic acid probe can be used in solution phase or it can be attached to a solid support. The immobilized probes can be attached directly to the solid support or through a linker arm between the support and the dye or between the support and a nucleic acid residue. Preferably, the probe is attached to the solid support by a linker (i.e., spacer arm, supra). The linker serves to distance the probe from the solid support. The linker is most preferably from about 5 to about 30 atoms in length, more preferably from about 10 to about 50 atoms in length. Exemplary attachment points include the 3'- or 5'-terminal nucleotide of the probe as well as other accessible sites discussed herein.

Chemical synthesis of nucleic acid probes containing a dye of the invention is optionally automated and is performed by coupling nucleosides through phosphorus-containing covalent linkages. The most commonly used oligonucleotide synthesis method involves reacting a nucleoside with a protected cyanoethyl phosphoramidite monomer in the presence of a weak acid. The coupling step is followed by oxidation of the resulting phosphite linkage. Finally, the cyanoethyl protecting group is removed and the nucleic acid is cleaved from the solid support on which it was synthesized. The labels of the present invention can be incorporated during oligonucleotide synthesis using a mono- or bis-phosphoramidite derivative of the fluorescent compound of the invention. Alternatively, the label can be introduced by combining a compound of the invention that includes a reactive functional group with the nucleic acid under appropriate conditions to couple the compound to the nucleic acid. In yet another embodiment, the fluorescent compound is attached to a solid support through a linker arm, such as a substituted or unsubstituted alkyl, substituted or unsubstituted heteroalkyl or a nucleic acid residue. Synthesis proceeds with the fluorescent moiety already in place on the growing nucleic acid chain.

Enzymatic methods of synthesis involve the use of fluorescent-labeled nucleic acids in conjunction with a nucleic acid template, a primer and an enzyme. Efficient enzymatic incorporation of a fluorescent-labeled nucleic acid is facilitated by selection of reaction partners that do not adversely affect the enzymes ability to couple the partners.

In those embodiments of the invention in which the dye-based fluorescent compound of the invention is attached to a nucleic acid, the carrier molecule is produced by either synthetic (solid phase, liquid phase or a combination) or enzymatically or by a combination of these processes.

Another synthetic strategy for the preparation of oligonucleotides is the H-phosphonate method (B. Froehler and M. Matteucci, *Tetrahedron Lett.*, vol 27, p 469-472, 1986). This method utilizes activated nucleoside H-phosphonate monomers rather than phosphoramidites to create the phosphate internucleotide linkage. In contrast to the phosphoramidite method, the resulting phosphonate linkage does not require oxidation every cycle but instead only a single oxidation step at the end of chain assembly. The H-phosphonate method may also be used to conjugate reporters and dyes to synthetic oligonucleotide chains (N. Sinha and R. Cook, *Nucleic Acids Research*, Vol 16, p. 2659, 1988).

In an exemplary embodiment, the synthesis and purification of the nucleic acid conjugates of compounds of the invention results in a highly pure conjugate, which, if it is a mixture, less than about 30% of the nucleic acid is unlabeled with a dye of the invention, preferably less than about 20% are unlabeled, more preferably less than about 10%, still more preferably less than about 5%, more preferably less than about 1%, more preferably less than about 0.5%, or more preferably less than about 0.1% and even more preferably less than 0.01% of the nucleic acid is unlabeled with a dye of the invention. In certain embodiments, the nucleic acid (e.g., nucleotides and/or nucleotide analogs) is incorporatable by a polymerase enzyme in a template-dependent polymerization reaction.

Dual Labeled Probes

The present invention also provides dual labeled probes that include both a dye of the invention and another label. Exemplary dual labeled probes include nucleic acid probes that include a nucleic acid with a dye of the invention attached thereto. Exemplary probes include both a dye of the invention and a quencher. The probes are of use in a variety of assay formats. For example, when a nucleic acid singly labeled with a dye of the invention is the probe, the interaction between the first and second nucleic acids can be detected by observing the interaction between the dye of the invention and the nucleic acid. Alternatively, the interaction is the quenching by a quencher attached to the second nucleic acid of the fluorescence from a dye of the invention.

The dyes of the invention are useful in conjunction with nucleic-acid probes in a variety of nucleic acid amplification/quantification strategies including, for example, 5'-nuclease assay, Strand Displacement Amplification (SDA), Nucleic Acid Sequence-Based Amplification (NASBA), Rolling Circle Amplification (RCA), as well as for direct detection of targets in solution phase or solid phase (e.g., array) assays. Furthermore, the dye of the invention-derivatized nucleic acids can be used in probes of substantially any format, including, for example, format selected from molecular beacons, Scorpion Probes™, Sunrise Probes™, conformationally assisted probes, light up probes, Invader Detection probes, and TaqMan™ probes. See, for example, Cardullo, R., et al., *Proc. Natl. Acad. Sci. USA*, 85:8790-8794 (1988); Dexter, D. L., *J. Chem. Physics*, 21:836-850 (1953); Hochstrasser, R. A., et al., *Biophysical Chemistry*, 45:133-141 (1992); Selvin, P., *Methods in Enzymology*, 246:300-334 (1995); Steinberg, I., *Ann. Rev. Biochem.*, 40:83-114 (1971); Stryer, L., *Ann. Rev. Biochem.*, 47:819-846 (1978); Wang, G., et al., *Tetrahedron Letters*, 31:6493-6496 (1990); Wang, Y., et al., *Anal. Chem.*, 67:1197-1203 (1995); Debouck, C., et al., in supplement to *nature genetics*, 21:48-50 (1999); Rehman, F. N., et al., *Nucleic Acids Research*, 27:649-655 (1999); Cooper, J. P., et al., *Biochemistry*, 29:9261-9268 (1990); Gibson, E. M., et al., *Genome Methods*, 6:995-1001 (1996); Hochstrasser, R. A., et al., *Biophysical Chemistry*, 45:133-141 (1992); Holland, P. M., et al., *Proc Natl. Acad. Sci USA*, 88:7276-7289 (1991); Lee, L. G., et al., *Nucleic Acids Rsch.*, 21:3761-3766 (1993); Livak, K. J., et al., *PCR Methods and Applications*, Cold Spring Harbor Press (1995); Vamosi, G., et al., *Biophysical Journal*, 71:972-994 (1996); Wittwer, C. T., et al., *Biotechniques*, 22:176-181 (1997); Wittwer, C. T., et al., *Biotechniques*, 22:130-38 (1997); Giesendorf, B. A. J., et al., *Clinical Chemistry*, 44:482-486 (1998); Kostrikis, L. G., et al., *Science*, 279:1228-1229 (1998); Matsuo, T., *Biochemica et Biophysica Acta*, 1379:178-184 (1998); Piatek, A. S., et al., *Nature Biotechnology*, 16:359-363 (1998); Schofield, P., et al., *Appl. Environ. Microbiology*, 63:1143-1147 (1997); Tyagi S., et al., *Nature Biotechnology*, 16:49-53 (1998); Tyagi, S., et al., *Nature Biotechnology*, 14:303-308 (1996); Nazarenko, I. A., et al., *Nucleic Acids Research*, 25:2516-2521 (1997); Uehara, H., et al., *Biotechniques*, 26:552-558 (1999); D. Whitcombe, et al., *Nature Biotechnology*, 17:804-807 (1999); Lyamichev, V., et al., *Nature Biotechnology*, 17:292 (1999); Daubendiek, et al., *Nature Biotechnology*, 15:273-277 (1997); Lizardi, P. M., et al., *Nature Genetics*, 19:225-232 (1998); Walker, G., et al., *Nucleic Acids Res.*, 20:1691-1696 (1992); Walker, G. T., et al., *Clinical Chemistry*, 42:9-13 (1996); and Compton, J., Nature, 350:91-92 (1991).

In view of the well-developed body of literature concerning the conjugation of small molecules to nucleic acids, many other methods of attaching donor/acceptor pairs to nucleic acids will be apparent to those of skill in the art.

More specifically, there are many linking moieties and methodologies for attaching groups to the 5'- or 3'-termini of nucleic acids, as exemplified by the following references: Eckstein, editor, Nucleic acids and Analogues: A Practical Approach (IRL Press, Oxford, 1991); Zuckerman et al., *Nucleic Acids Research*, 15: 5305-5321 (1987) (3'-thiol group on nucleic acid); Sharma et al., *Nucleic Acids Research*, 19: 3019 (1991) (3'-sulfhydryl); Giusti et al., *PCR Methods and Applications*, 2: 223-227 (1993) and Fung et al., U.S. Pat. No. 4,757,141 (5'-phosphoamino group via Aminolink TM II available from P.E. Biosystems, CA.) Stabinsky, U.S. Pat. No. 4,739,044 (3-aminoalkylphosphoryl group); Agrawal et al., *Tetrahedron Letters*, 31: 1543-1546 (1990) (attachment via phosphoramidate linkages); Sproat et al., *Nucleic Acids Research*, 15: 4837 (1987) (5-mercapto group); Nelson et al., *Nucleic Acids Research*, 17: 7187-7194 (1989) (3'-amino group), and the like.

Exemplary fluorophores that can be combined in a probe or scaffold-based dye with a dye of the invention include those set forth in Table 1.

TABLE 1

Exemplary Donors or Acceptors for Compounds of the Invention 4-acetamido-4'-isothiocyanatostilbene-2,2'disulfonic acid
acridine and derivatives:
   acridine
   acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:
coumarin
   7-amino-4-methylcoumarin (AMC, Coumarin 120)
   7-amino-4-trifluoromethylcouluarin (Coumaran 151)
cyanine dyes
cyanosine
4',6-diaminidino-2-phenylindole (DAPI)

TABLE 1-continued

Exemplary Donors or Acceptors for Compounds of the Invention

5',5''-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:
    eosin
    eosin isothiocyanate
erythrosin and derivatives:
    erythrosin B
    erythrosin isothiocyanate
ethidium
fluorescein and derivatives:
    5-carboxyfluorescein (FAM)
    5-(4,6-dichlorotriazin-2-yl)aminofluorescein (DTAF)
    2',7'-dimethoxy-4'5'-dichloro-6-carboxyfluorescein (JOE)
    fluorescein
    fluorescein isothiocyanate
    QFITC (XRITC)
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde
pyrene and derivatives:
    pyrene butyrate
    succinimidyl 1-pyrene butyrate
quantum dots
Reactive Red 4 (Cibacron ™ Brilliant Red 3B-A)
rhodamine and derivatives:
    6-carboxy-X-rhodamine (ROX)
    6-carboxyrhodamine (R6G)
    lissamine rhodamine B sulfonyl chloride rhodamine (Rhod)
    rhodamine B
    rhodamine 123
    rhodamine X isothiocyanate
    sulforhodamine B
    sulforhodamine 101
sulfonyl chloride derivative of sulforhodamine 101 (Texas Red)
N,N,N',N'-tetramethyl-6-carboxyrhodamine (TAMRA)
tetramethyl rhodamine
    tetramethyl rhodamine isothiocyanate (TRITC)
riboflavin
rosolic acid
terbium chelate derivatives
Black Hole Quenchers ™

There is a great deal of practical guidance available in the literature for functionalizing fluorophores and selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via common reactive groups that can be added to a nucleic acid, as exemplified by the following references: Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a nucleic acid, peptide or other polymer.

As will be apparent to those of skill in the art the methods set forth above are equally applicable to the coupling to a nucleic acid of groups other than the fluorescent compounds of the invention, e.g., quenchers, intercalating agents, hybridization enhancing moieties, minor groove binders, alkylating agents, cleaving agents, etc.

When the nucleic acids are synthesized utilizing an automated nucleic acid synthesizer, the donor and acceptor moieties are preferably introduced during automated synthesis. Alternatively, one or more of these moieties can be introduced either before or after the automated synthesis procedure has commenced. For example, donor and/or acceptor groups can be introduced at the 3'-terminus using a solid support modified with the desired group(s). Additionally, donor and/or acceptor groups can be introduced at the 5'-terminus by, for example a derivative of the group that includes a phosphoramidite. In another exemplary embodiment, one or more of the donor and/or acceptor groups is introduced after the automated synthesis is complete.

In the dual labeled probes, the quencher moiety is preferably separated from the dye of the invention by at least about 10 nucleotides, and more preferably by at least about 15 nucleotides. The quencher moiety is preferably attached to either the 3'- or 5'-terminal nucleotides of the probe. The dye of the invention moiety is also preferably attached to either the 3'- or 5'-terminal nucleotides of the probe. More preferably, the donor and acceptor moieties are attached to the 3'- and 5'- or 5'- and 3'-terminal nucleotides of the probe, respectively, although internal placement is also useful.

Once the desired nucleic acid is synthesized, it is preferably cleaved from the solid support on which it was synthesized and treated, by methods known in the art, to remove any protecting groups present (e.g., 60° C., 5 h, concentrated ammonia). In those embodiments in which a base-sensitive group is attached to the nucleic acids (e.g., TAMRA), the deprotection will preferably use milder conditions (e.g., butylamine: water 1:3, 8 hours, 70° C.). Deprotection under these conditions is facilitated by the use of quick deprotect amidites (e.g., dC-acetyl, dG-dmf).

Peptide Probes

Peptides, proteins and peptide nucleic acids that are labeled with a quencher and a dye of the invention can be used in both in vivo and in vitro enzymatic assays.

Peptide constructs useful in practicing the invention include those with the following features: i) a quencher; ii) a dye of the invention; and iii) a cleavage or assembly recognition site for the enzyme. Moreover, the peptide construct is preferably exists in at least one conformation that allows donor-acceptor energy transfer between the dye of the invention and the quencher when the fluorophore is excited.

In the dual labeled probes of the invention, the donor and acceptor moieties are connected through an intervening linker moiety. The linker moiety, preferably, includes a peptide moiety, but can be or can include another organic molecular moiety, as well. In a preferred embodiment, the linker moiety includes a cleavage recognition site specific for an enzyme or other cleavage agent of interest. A cleavage site in the linker moiety is useful because when a tandem construct is mixed with the cleavage agent, the linker is a substrate for cleavage by the cleavage agent. Rupture of the linker moiety results in separation of the dye and the quencher. The separation is measurable as a change in donor-acceptor energy transfer. Alternatively, peptide assembly can be detected by an increase in donor-acceptor energy transfer between a peptide fragment bearing a fluorescent dye and a peptide fragment bearing a donor moiety.

When the cleavage agent of interest is a protease, the linker generally includes a peptide containing a cleavage recognition sequence for the protease. A cleavage recognition sequence for a protease is a specific amino acid sequence recognized by the protease during proteolytic cleavage. Many protease cleavage sites are known in the art, and these and other cleavage sites can be included in the linker moiety. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); Bouvier et al. *Meth. Enzymol.* 248: 614 (1995), Hardy et al., in AMYLOID PROTEIN PRECURSOR IN DEVELOPMENT, AGING, AND ALZHEIMER'S DISEASE, ed. Masters et al. pp. 190-198 (1994).

Solid Support Immobilized Dye Analogues

The amino acid or peptide linked dyes of the invention can be immobilized on substantially any polymer, biomolecule, or solid or semi-solid material having any useful configuration. Moreover, any conjugate comprising one or more dye of the invention can be similarly immobilized. When the support is a solid or semi-solid, examples of preferred types of supports for immobilization of the nucleic acid probe include, but are not limited to, controlled pore glass, glass plates, polystyrene, avidin coated polystyrene beads, cellulose, nylon, acrylamide gel and activated dextran. These solid supports are preferred because of their chemical stability, ease of functionalization and well-defined surface area. Solid supports such as, controlled pore glass (CPG, 500 Å, 1000 Å) and non-swelling high cross-linked polystyrene (1000 Å) are particularly preferred.

According to the present invention, the surface of a solid support is functionalized with a dye of the invention or a species to which a dye of the invention is conjugated. For clarity of illustration, the following discussion focuses on attaching a reactive dye of the invention to a solid support. The following discussion is also broadly relevant to attaching to a solid support a species that includes within its structure a dye of the invention.

The dyes of the invention are preferably attached to a solid support by forming a bond between a reactive group on the dye of the invention (e.g., on an amino acid or peptide linker) and a reactive group on the surface of the solid support, thereby derivatizing the solid support with one or more dye of the invention. Alternatively, the reactive group on the dye of the invention is coupled with a reactive group on a linker arm attached to the solid support. The bond between the solid support and the dye of the invention is preferably a covalent bond, although ionic, dative and other such bonds are useful as well. Reactive groups which can be used in practicing the present invention are discussed in detail above and include, for example, amines, hydroxyl groups, carboxylic acids, carboxylic acid derivatives, alkenes, sulfhydryls, siloxanes, etc.

A large number of solid supports appropriate for practicing the present invention are available commercially and include, for example, peptide synthesis resins, both with and without attached amino acids and/or peptides (e.g., alkoxybenzyl alcohol resin, aminomethyl resin, aminopolystyrene resin, benzhydrylamine resin, etc. (Bachem)), functionalized controlled pore glass (BioSearch Technologies, Inc.), ion exchange media (Aldrich), functionalized membranes (e.g., —COOH membranes; Asahi Chemical Co., Asahi Glass Co., and Tokuyama Soda Co.), and the like.

Microarrays

The present invention also provides microarrays including immobilized dye of the invention and compounds (e.g., peptides, nucleic acids, bioactive agents, etc.) functionalized with a dye of the invention. Moreover, the invention provides methods of interrogating microarrays using probes that are functionalized with a dye of the invention. The immobilized species and the probes are selected from substantially any type of molecule, including, but not limited to, small molecules, peptides, enzymes nucleic acids and the like.

Nucleic acid microarrays consisting of a multitude of immobilized nucleic acids are revolutionary tools for the generation of genomic information, see, Debouck et al., in supplement to *Nature Genetics,* 21:48-50 (1999). The discussion that follows focuses on the use of a dye of the invention in conjunction with nucleic acid microarrays. This focus is intended to be illustrative and does not limit the scope of materials with which this aspect of the present invention can be practiced. See, Lehrach, et al., HYBRIDIZATION FINGERPRINTING IN GENOME MAPPING AND SEQUENCING, GENOME ANALYSIS, Vol. 1, Davies et al, Eds., Cold Springs Harbor Press, pp. 39-81 (1990), Pirrung et al. (U.S. Pat. No. 5,143,854, issued 1992), and also by Fodor et al., (*Science,* 251: 767-773 (1991), Southern et al. (*Genomics,* 13: 1008-1017 (1992), Khrapko, et al., *DNA Sequence,* 1: 375-388 (1991), Kleinfield et al., *J. Neurosci.* 8:4098-120 (1998)), Kumar et al., *Langmuir* 10:1498-511 (1994), Xia, Y., *J. Am. Chem. Soc.* 117:3274-75 (1995), Hickman et al., *J. Vac. Sci. Technol.* 12:607-16 (1994), Mrkish et al. *Ann. Rev. Biophys. Biomol. Struct.* 25:55-78 (1996).

Probes of Enzymatic Reactions

In various embodiments, the invention provides a composition which is a substrate for an enzyme, the substrate comprising a component reacted upon by the enzyme, a fluorescent label component and an amino acid or peptide linker component conjugating these two components. The linker component interacts with the enzyme to increase the affinity of the fluorophore-linker-enzyme reactive component with the enzyme, reducing the $K_m$ of the reaction between the enzyme and the enzyme-reactive component relative to that of an analogous reaction in which the conjugate does not include the linker component. Exemplary interaction modalities by which the linker increases the affinity of the conjugate for the enzyme include, without limitation, electrostatic, hydrophobic and steric interactions. In various embodiments, the $K_m$ is reduced at least 10%, at least 20%, at least 30%, at least 40% or at least 50% relative to the $K_m$ of the reaction with an analogous conjugate without the linker component.

Probes that do not have the amino acid or peptide linker of the compounds of the present invention are referred to as "otherwise identical" to the probes having the amino acid or peptide linker. Such probes are represented by the formula:

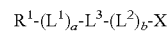

in which each of the radicals and indices is as discussed herein, and $L^3$ is a non-amino acid, non-peptide linker. An exemplary linker for $L^3$ is a substituted or unsubstituted alkyl or substituted or unsubstituted heteroalkyl linker. In various embodiments, $L^3$ is from 1 to 12 atoms long, e.g., from 2 to 10 atoms, or from 4 to 8 atoms long. In various embodiments, $L^3$ is a bond ("zero order linker") linking two components of the conjugate.

In various embodiments, the linker serves to enhance the interaction between a conjugate of the invention and a protein, such as a DNA polymerase. The linker can enhance the interaction between the conjugate and the protein through electrostatic, hydrophobic, or steric interactions. In an exemplary embodiment in which the conjugate is utilized in a single molecule nucleic acid sequencing technique, the linker enhances the interaction between the conjugate and the DNA polymerase, thereby lowering the $K_m$ of the sequencing reaction and influencing the 2-slow step to achieve optimized residence time of the conjugate on the polymerase and enzyme kinetics. In examples of this embodiment, the linker is an amino acid or peptide. In various embodiments, the conjugate has the formula:

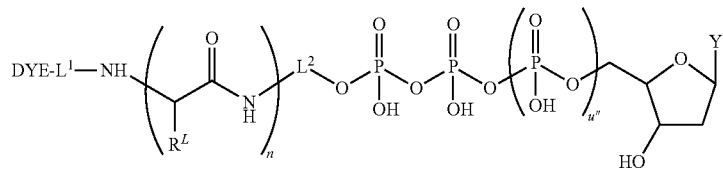

in which $L^1$ and $L^2$ are independently selected from bonds and adaptors, e.g., substituted or unsubstituted alkyl or substituted or unsubstituted heteroalkyl. The index u" is an integer selected from 1, 2, 3, 4, 5, 6, 7, 8, 9, 10, 11, 12 or higher. $R^L$ is H or is an amino acid side-chain (e.g., $NH_2$, SH, COOH) or a derivatized side chain (e.g., $CH_2OP(O)(OR)_2$, wherein each R is independently selected from H, substituted or unsubstituted alkyl, substituted or unsubstituted heteroalkyl, substituted or unsubstituted aryl, substituted or unsubstituted heteroaryl, and substituted or unsubstituted heterocycloalkyl. The index n is an integer selected from 0, 1, 2, 3, 4, 5, 6 or higher. Each of the n amino acid residues is independently selected from naturally occurring or unnatural amino acids. An exemplary amino acid/peptide linker is one in which n is an integer selected from 1, 2, 3, 4, 5 or higher. In various embodiments, the amino acid/peptide is lysine or a peptide containing lysine, glutamic acid or a peptide containing glutamic acid, serine or a peptide containing serine. In various embodiments, the peptide linker is composed only of lysine, only of glutamic acid, only of serine or only of O-phosphoserine (or an ester thereof).

In various embodiments, the linker in the conjugate of the invention includes one, two, three or more anionic amino acids in the linker. An exemplary linker includes only anionic amino acids. In various embodiments, the linker in the conjugate of the invention includes one, two, three or more hydrophobic amino acids. An exemplary linker includes only hydrophobic amino acids. In various embodiments, the linker in the conjugates of the invention includes one, two, three or more cationic amino acids in the linker. An exemplary linker includes only cationic amino acids. The various permutations of combinations of anionic, hydrophobic and cationic amino acids in a linker of 1, 2, 3, 4, 5, or 6 amino acid residues is encompassed in this disclosure.

In an exemplary embodiment, the linker in the compounds of the invention includes at least one amino acid besides lysine. In various embodiments, the linker is not poly- or oligo-lysine. In various embodiments, the linker is not Lys, $Lys_4$, $Lys_5$ or $Lys_6$. In a further exemplary embodiment, the linker is not poly- or oligo-proline. In various embodiments, the linker is not Pro, $Pro_2$, $Pro_3$, $Pro_4$, $Pro_5$ or $Pro_6$.

Additional peptide linkers of use in the present invention are set forth in commonly owned U.S. Patent Application Publication No. 20090233302, the disclosure of which is incorporated in its entirety herein by reference for all purposes.

The Methods

In addition to the compounds of the invention, there are also provided an array of methods utilizing the compounds. The following discussion is intended to be illustrative of the type and scope of methods with which the compounds of the invention can be practiced and should not be interpreted as being either exhaustive or limiting.

Monitoring Enzymatic Reactions

Peptides, proteins and peptide nucleic acids that are labeled with a quencher and a dye of the invention can be used in both in vivo and in vitro enzymatic assays.

Thus, in another aspect, the present invention provides a method for determining whether a sample contains an enzyme. The method comprises: (a) contacting the sample with a peptide construct that includes a dye of the invention; (b) exciting the fluorophore; and (c) determining a fluorescence property of the sample, wherein the presence of the enzyme in the sample results in a change in the fluorescence property.

Peptide constructs useful in practicing the invention include those with the following features: i) a quencher; ii) a dye of the invention; and iii) a cleavage or assembly recognition site for the enzyme. Moreover, the peptide construct preferably exists in at least one conformation that allows donor-acceptor energy transfer between the dye of the invention and the quencher when the fluorophore is excited.

The assay is useful for determining the amount of enzyme in a sample. For example, by determining the degree of donor-acceptor energy transfer at a first and second time after contact between the enzyme and the tandem construct, and determining the difference in the degree of donor-acceptor energy transfer. The difference in the degree of donor-acceptor energy transfer reflects the amount of enzyme in the sample.

The assay methods also can also be used to determine whether a compound alters the activity of an enzyme, i.e., screening assays. Thus, in a further aspect, the invention provides methods of determining the amount of activity of an enzyme in a sample from an organism. The method includes: (a) contacting a sample comprising the enzyme and the compound with a peptide construct that includes a dye of the invention; (b) exciting the fluorophore; and (c) determining a fluorescence property of the sample, wherein the activity of the enzyme in the sample results in a change in the fluorescence property. Peptide constructs useful in this aspect of the invention are substantially similar to those described immediately above.

In a preferred embodiment, the amount of enzyme activity in the sample is determined as a function of the degree of donor-acceptor energy transfer in the sample and the amount of activity in the sample is compared with a standard activity for the same amount of the enzyme. A difference between the amount of enzyme activity in the sample and the standard activity indicates that the compound alters the activity of the enzyme.

Representative enzymes with which the present invention can be practiced include, for example, nucleotide polymerases (e.g., DNA polymerase), trypsin, enterokinase, HIV-1 protease, prohormone convertase, interleukin-1b-converting enzyme, adenovirus endopeptidase, cytomegalovirus assemblin, leishmanolysin, β-secretase for amyloid precursor protein, thrombin, renin, angiotensin-converting enzyme, cathepsin-D and a kininogenase, and proteases in general.

An exemplary assay for proteases are based on donor-acceptor energy transfer from a donor fluorophore to a quencher placed at opposite ends of a short peptide chain containing the potential cleavage site (see, Knight C. G., *Methods in Enzymol.* 248:18-34 (1995)). Proteolysis separates the fluorophore and quencher, resulting in increased intensity in the emission of the donor fluorophore. Existing protease assays use short peptide substrates incorporating unnatural chromophoric amino acids, assembled by solid phase peptide synthesis.

In a further aspect, the invention provides a method of monitoring an enzyme reaction. The method generally comprises providing a reaction mixture comprising die enzyme and at least a first reactant composition, the reactant composition comprising a compound having a reactant component, which is a substrate for the enzyme, a fluorescent label component, and a linker component joining the reactant component to the label component. In various embodiments, the linker component increases the affinity of the conjugate for the enzyme. In various embodiments, the increased affinity reduces the $K_m$ of the reaction, e.g., by 10%, at least 20%, at least 30%, at least 40% or at least 50% relative to the $K_m$ of the reaction with an analogous conjugate without the linker component. The reaction mixture is illuminated to excite the fluorescent label component, and a fluorescent signal from the reaction mixture characteristic of the enzyme reaction is detected.

In an exemplary embodiment, the enzymatic reaction is the reaction of a polymerase with a nucleic acid.

Nucleic Acid Sequencing

In various embodiments, the present invention provides a method for nucleic acid sequencing using one or more compounds of the invention. An exemplary sequencing method is single molecule nucleic acid sequencing.

Significant interest in the sequencing of single DNA molecules dates to 1989 when Keller and colleagues began experimenting with "sequencing by degradation." In their experiments, isolated fully-labeled DNA molecules are degraded by an exonuclease, and individual labeled bases are detected as they are sequentially cleaved from the DNA (Jett, J. H. et al., *J. Biomol. Struct. Dynamics,* 7, 301-309 (1989); Stephan, J. et al., *J. Biotechnol.*, 86, 255-267 (2001); Werner, J. H. et al., *J. Biotechnol.*, 102, 1-14 (2003)). This approach was ultimately compromised by poor DNA solubility caused by the densely-packed dye labels. More recently, alternative single-molecule approaches have been investigated, including "sequencing by synthesis," where bases are detected one at a time as they are sequentially incorporated into DNA by a polymerase (Braslaysky, I. et al., *Proc. Natl. Acad. Sci. USA,* 100, 3960-3964 (2003); Levene, M. J. et al., *Science,* 299, 682-686 (2003); Metzker, M. L., *Genome Res.,* 15, 1767-1776 (2005)); and nanopore sequencing where electrical signals are detected while single DNA molecules pass through protein or solid-state nanopores (Akeson, M. et al., *Biophys. J.,* 77, 3227-3233 (1999); Lagerqvist, J. et al., *Nano Lett.,* 6, 779-782 (2006); Rhee, K. J. et al, Annals of emergency medicine, 13, 916-923 (1984)). So far, only sequencing by synthesis has been successful. In the method of Quake and colleagues (Braslaysky, I. et al., *Proc. Natl. Acad. Sci. USA,* 100, 3960-3964 (2003)), base-labeled nucleotide triphosphates (dNTPs) are incorporated into DNA immobilized on a microscope coverglass. Each type of dNTP is applied separately in a fluidics cycle, and incorporated bases are imaged on the surface after washing away the excess of free nucleotides. While the obtained sequence reads are short, high sequencing rates can potentially be achieved by analyzing billions of different, individual molecules in parallel with applications in re-sequencing and gene expression profiling.

To obtain long single-molecule reads, potentially tens of kilobases, sequencing-by-synthesis approaches using phosphate-labeled nucleotides have been developed (Levene, M. J. et al., *Science,* 299, 682-686 (2003)). These nucleotides are labeled with a fluorophore on the terminal phosphate instead of on the base. Labeled nucleotides are detected while bound to polymerase during the catalytic reaction. The label is released with pyrophosphate as the nucleotide is incorporated into DNA. An advantage is that the DNA remains label-free and fully soluble. Individual polymerase enzymes immobilized on a microscope coverglass are monitored in real time to detect the sequence of incorporated nucleotides. In order to achieve long reads, the polymerase, but not the DNA, can be attached to the coverglass. Polymerase attachment facilitates detection because it keeps the active site at a single position on the coverglass surface. In the alternative format, with the polymerase in solution and the DNA attached, the enzyme active site would be a moving target for detection, diffusing up to several microns from the DNA attachment point as the primer strand is extended from long templates.

U.S. Pat. No. 6,255,083, issued to Williams and incorporated herein by reference, discloses a single molecule sequencing method on a solid support. The solid support is optionally housed in a flow chamber having an inlet and outlet to allow for renewal of reactants that flow past the immobilized polymerases. The flow chamber can be made of plastic or glass and should either be open or transparent in the plane viewed by the microscope or optical reader.

Accordingly, it is within the scope of the present invention to utilize the compounds set forth herein in single molecule DNA sequencing.

In accordance with one embodiment of the methods of invention, the compounds described herein are used in analyzing nucleic acid sequences using a template dependent polymerization reaction to monitor the template dependent incorporation of specific analogs into a synthesized nucleic acid strand, and thus determine the sequence of nucleotides present in the template nucleic acid strand. In particular, a polymerase enzyme is complexed with the template strand in the presence of one or more nucleotides and/or one or more nucleotide analogs of the invention. In preferred aspects, only the labeled analogs of the invention are present representing analogous compounds to each of the four natural nucleotides, A, T, G and C. When a particular base in the template strand is encountered by the polymerase during the polymerization reaction, it complexes with an available analog that is complementary to such nucleotide, and incorporates that analog into the nascent and growing nucleic acid strand, cleaving between the α and β phosphorus atoms in the analog, and consequently releasing the labeling group (or a portion thereof). The incorporation event is detected, either by virtue of a longer presence of the analog in the complex, or by virtue of release of the label group into the surrounding medium. Where different labeling groups are used for each of the types of analogs, e.g., A, T, G or C, identification of a label of an incorporated analog allows identification of that analog and consequently, determination of the complementary nucleotide in the template strand being processed at that time. Sequential reaction and monitoring permits a real-time monitoring of the polymerization reaction and determination of the sequence of the template nucleic acid. As noted above, in particularly preferred aspects, the polymerase enzyme/template complex is provided immobilized within an optical confinement that permits observation of an individual complex, e.g., a zero mode waveguide. In addition to their use in sequencing, the analogs of the invention are also equally useful in a variety of other genotyping analyses, e.g., SNP genotyping use single base extension methods, real time monitoring of amplification, e.g., RT-PCR methods, and the like. See, for example, U.S. Pat. Nos. 7,056,661, 7,052,847, 7,033,764, 7,056,676, 6,917,726, 7,013,054, 7,181,122, 7,292,742 and 7,170,050 and 7,302,146, the full disclosures of which are incorporated herein by reference in their entirety for all purposes.

The present invention also provides methods of using the compounds described herein in performing nucleic acid analyses, and particularly nucleic acid sequence analyses. The methods of the invention typically comprise providing a template nucleic acid complexed with a polymerase enzyme in a template dependent polymerization reaction to produce a nascent nucleic acid strand, contacting the polymerase and template nucleic acid with a compound of the invention, and detecting whether or not a synthon derived from the compound (e.g., monophosphate nucleic acid subunit) was incorporated into the nascent strand during the polymerization reaction, and identifying a base in the template strand based upon incorporation of the compound. Preferably, the foregoing process is carried out so as to permit observation of individual nucleotide incorporation reactions, through the use of, for example, an optical confinement, that allows observation of an individual polymerase enzyme, or through the use of a heterogeneous assay system, where label groups released from incorporated analogs are detected.

The invention also provides methods of monitoring nucleic acid synthesis reactions. The methods comprise contacting a polymerase/template/primer complex with a fluorescently labeled nucleotide or nucleotide analog having a nucleotide or nucleotide analog component, a fluorescent label component, and a linker component joining die nucleotide or nucleotide analog component to the label component, wherein the linker component increases the affinity of the conjugate for the enzyme, reducing the $K_m$ of the reaction, e.g., by 10%, at least 20%, at least 30%, at least 40% or at least 50% relative to the $K_m$ of the reaction with an analogous conjugate without the linker component. A characteristic signal from the fluorescent dye is then detected that is indicative of incorporation of the nucleotide or nucleotide analog into a primer extension reaction.

The amino acid or peptide linked fluorophores of the invention are of use in single molecule or single molecule real time (SMRT) DNA sequencing assays. Of particular note in this context is the ability provided by the invention to design fluorophores with selected absorbance and emission properties including wavelength and intensity. The compounds of the invention provide for very versatile assay design. For example, according to the present invention a series of fluorophores of use in an assay are readily designed to have selected absorbance and emission wavelengths and emission intensities, allowing multiple fluorophores to be utilized and distinguished in an assay. In exemplary embodiments, use of compounds of the invention in a multifluorophore assay, e.g., single molecule DNA sequencing, enhances assay performance by at least about 10%, at least about 20% or at least about 30% over a similar assay using currently available fluorophores.

In single-molecule DNA sequencing by synthesis, for example as described Eid, J. et al., Science, 323(5910), 133-138 (2009), the incorporation of specific nucleotides can be determined by observing bright phases and dark phases which correspond, for example, to reaction steps in which a fluorescent label is associated with the polymerase enzyme, and steps in which the fluorescent label is not associated with the enzyme. In some embodiments of the invention, the polymerase reaction system will exhibit two slow (kinetically observable) reaction steps wherein each of the steps is in a bright phase. In some embodiments of the invention, the system will exhibit two kinetically observable reaction steps wherein each of the steps is in a dark phase. In some cases, the system will have four kinetically observable (slow) reaction steps, two slow steps in a bright phase and two slow steps in a dark phase.

In an exemplary embodiment, the conjugates of the invention exhibit an enhanced two-slow step character in single molecule DNA sequencing when compared to analogous cyanine dyes without amino acid linkers between the dye and the nucleic acid. Exemplary two slow step results for a cyanine dye with a lysine linker and a triphosphate nucleic acid are set forth below:

| Conjugate | K1 (S-1) | K2 (S-1) | 2SS characteristics |
|---|---|---|---|
| Tri-phosphate | 9.496 | 0.371 | 25.6 |
| 1Lys-tri-phosphate | 12.96 | 0.96 | 13.5 |
| 2Lys-tri-phosphate | 2.645 | 0.406 | 6.5 |
| 2Glu-tri-phosphate | 7.898 | 1.082 | 7.3 |

Polymerase Chain Reaction

In another aspect, the invention provides a method for detecting amplification by PCR of a target sequence. Methods of monitoring PCR using dual labeled nucleic acid probes are known in the art. See, *Expert Rev. Mol. Diagn.,* 5(2), 209-219 (2005).

The dyes and their conjugates described herein can be used in substantially any nucleic acid probe format. For example, the dyes of the invention can be incorporated into probe motifs, such as Taqman™ probes (Held et al., *Genome Res.* 6: 986-994 (1996), Holland et al., *Proc. Nat. Acad. Sci. USA* 88: 7276-7280 (1991), Lee et al., *Nucleic Acids Res.* 21: 3761-3766 (1993)), molecular beacons (Tyagi et al., *Nature Biotechnology* 14:303-308 (1996), Jayasena et al., U.S. Pat. No. 5,989,823, issued Nov. 23, 1999)) scorpion probes (Whitcomb et al., *Nature Biotechnology* 17: 804-807 (1999)), sunrise probes (Nazarenko et al., *Nucleic Acids Res.* 25: 2516-2521 (1997)), conformationally assisted probes (Cook, R., copending and commonly assigned U.S. patent application Ser. No. 09/591,185), peptide nucleic acid (PNA)-based light up probes (Kubista et al., WO 97/45539, December 1997), double-strand specific DNA dyes (Higuchi et al, *Bio/Technology* 10: 413-417 (1992), Wittwer et al, *BioTechniques* 22: 130-138 (1997)) and the like. These and other probe motifs with which the present dyes can be used are reviewed in NONISOTOPIC DNA PROBE TECHNIQUES, Academic Press, Inc. 1992.

Nucleic Acid Detection

In another embodiment, the invention provides a method of detecting a target nucleic acid in an assay mixture or other sample. The following discussion is generally relevant to the assays described herein. This discussion is intended to illustrate the invention by reference to certain preferred embodiments and should not be interpreted as limiting the scope of probes and assay types in which the compounds of the invention find use. Other assay formats utilizing the compounds of the invention will be apparent to those of skill in the art.

An exemplary method uses a dye of the invention or a conjugate thereof to detect a nucleic acid target sequence. The method includes: (a) contacting the target sequence with a detector nucleic acid that includes a dye of the invention and a quencher; (b) hybridizing the detector nucleic acid to the target sequence, thereby altering the conformation of the detector nucleic acid, causing a change in a fluorescence parameter; and (c) detecting the change in the fluorescence parameter, thereby detecting the nucleic acid target sequence.

In various embodiments, the detector nucleic acid includes a single-stranded target binding sequence. The binding sequence has linked thereto: i) a quencher; and ii) a dye of the invention. Moreover, prior to its hybridization to a complementary sequence, the detector nucleic acid is preferably in a conformation that allows donor-acceptor energy transfer between the quencher and the dye of the invention when the fluorophore is excited. Furthermore, in the methods described in this section, a change in fluorescence is detected as an indication of the presence of the target sequence. The change in fluorescence is preferably detected in real time.

Kits

In another aspect, the present invention provides kits containing one or more dye of the invention or a conjugate thereof. In one embodiment, a kit includes a reactive dye of the invention and directions for attaching this derivative to another molecule. In another embodiment, the kit includes a dye-labeled polyphosphate nucleic acid in which an amino acid or peptide linker is present between the dye and the polyphosphate nucleic acid. The kit further includes one or more component selected from buffers or other compounds or solutions of use in practicing the method, an enzyme (e.g., a DNA polymerase), cofactors necessary for enzyme reactions, and directions for performing the assay.

The following examples are provided by way of illustration only and not by way of limitation. Those of skill in the art will readily recognize a variety of non-critical parameters that could be changed or modified to yield essentially similar results.

EXAMPLES

Example 1

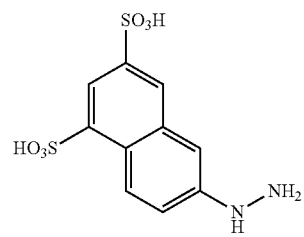

6-Hydrazino-1,3-naphthalenedisulfonate (1)

To a solution of disodium 6-amino-1,3-naphthalenedisulfonate hydrate (10.0 g, 28.8 mmol) in 50% hydrochloric acid (200 mL) at 0° C. was added dropwise a cold solution of sodium nitroxide (2.18 g, 31.7 mmol) in water (20 mL). After completion of addition (~25 min) the solution was stirred for an additional 30 min at 0° C. followed by dropwise addition of a cold solution of $SnCl_2$ (6.0 g, 31.7 mmol) in hydrochloric acid (10 mL) in 40 min. Continue to stir at 0° C. for 1 h and then ambient temperature for 1 h. Concentrated to dryness and triturated with hot iPrOH (400 mL). Filtered to collect the solid, washed with iPrOH (2×30 mL), ethyl acetate (2×30 mL) and dried. Further drying in an oven at 40° C. under high vacuum for 18 h provided 12.4 g of a solid product (quantitative yield).

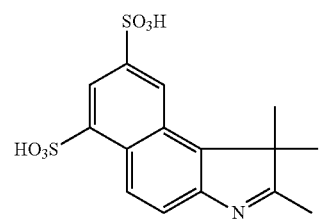

1,1,2-Trimethylbenz[e]indole-6,8-disulfonate (2)

A solution of 6-hydrazino-1,3-naphthalenedisulfonate (10.3 g, 32.5 mmol), isopropylmethylketone (7.6 mL, 71 mmol), potassium acetate (6.82 g, 69 mmol) in acetic acid (50 mL) was heated under reflux in an oil bath for 24 h. After cooling to ambient temperature the solvent was evaporated off under reduced pressure to dryness and triturated with iPrOH (100 mL). The resultant solid was collected, washed with iPrOH (2×30 mL) and dried. Further drying in an oven at 40° C. under high vacuum for 18 h provided the solid product (9.59 g, 80%).

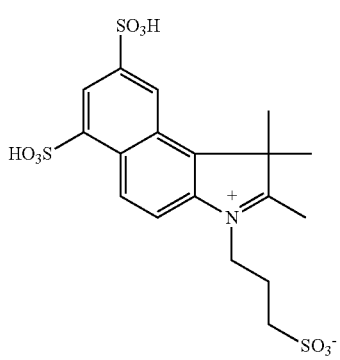

1,1,2-Trimethyl-3-(3-sulfopropyl)benz[e]indolium-6,8-disulfonate (3)

A suspension of 1,1,2-trimethylbenz[e]indole-6,8-disulfonate (2.5 g, 6.8 mmol) and 1,3-propanesultone (2.16 mL, 24.4 mmol) in 1,2-dichlorobenzene (50 mL) was heated in an oil bath at 140° C. for 24 h. After cooling to ambient temperature the solvent was decanted, the solid was washed with ethyl acetate (3×20 mL) and solvent was decanted. The solid was triturated with methanol (50 mL) and then ethyl acetate (50 mL) was added. Filtered to collect the solid, washed with ethyl acetate (2×20 mL), ether (2×20 mL) and dried in an oven at 40° C. under high vacuum for 18 h to afford 1.9 g (50%) of a solid product.

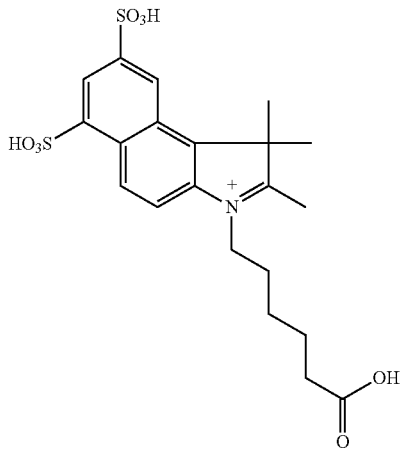

3-Carboxypentyl-1,1,2-Trimethylbenz[e]indolium-6,8-disulfonate (4)

A suspension of 1,1,2-trimethylbenz[e]indol-6,8-disulfonate (4.82 g, 13.0 mmol), bromohexanoic acid (25 g, 130 mmol) in a 250 mL round bottom flask was heated in an oil bath at 125° C. for 40 h. After cooling to ambient temperature ethyl acetate (100 mL) was added the solid was triturated. Filtered to collect the solid, washed with ethyl acetate (3×50 mL), ether (2×20 mL) and dried. Further drying in an oven at 40° C. under high vacuum for 18 h gave 4.41 g (70.0%) of the product.

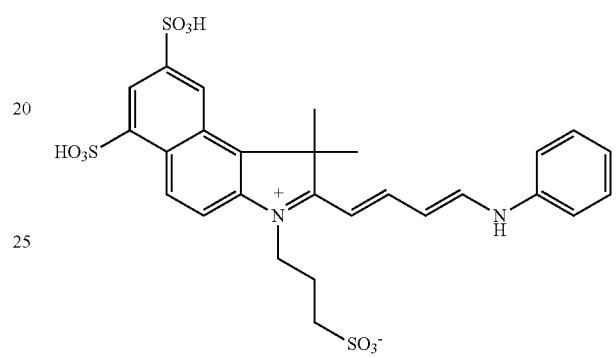

2-[(1E,3E)-4-Anilinobuta-1,3-dienyl]-1,1-Dimethyl-3-(3-sulfopropyl)benz[e]indolium-6,8-disulfonate (5)

A solution of 1,1,2-trimethyl-3-(3-sulfopropyl)benz[e]indolium-6,8-disulfonate (1.03 g, 2.10 mmol) and malonaldehyde dianil hydrochloride (596 mg, 2.30 mmol) in acetic acid (10 mL) was heated to reflux for 18 h. The progress of the reaction was monitored with analytical HPLC for the disappearance of the starting material, and the formation of the product. Solvent was removed under reduced pressure and the residual dark solid was washed with ethyl acetate (3×20 mL). The dried solid was used without further purification in the next reaction for dicarbocyanine dye synthesis.

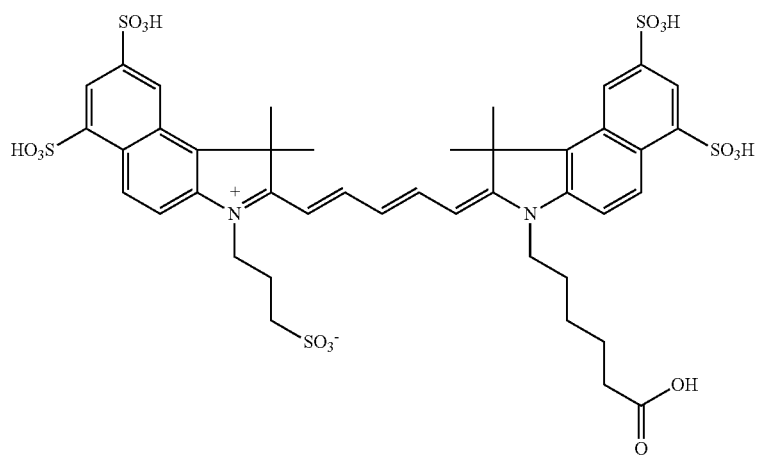

Preparation of 6

To a solution of 2-[(1E,3E)-4-anilinobuta-1,3-dienyl]-1,1-Dimethyl-3-(3-sulfopropyl)benz[e]indolium-6,8-disulfonate (69.9 mg, 0.114 mmol), 3-carboxypentyl-1,1,2-Trimethylbenz[e]indolium-6,8-disulfonate (55.2 mg, 0.114 umol) in N,N-dimethylformamide (1.0 mL) was added acetic anhydride (200 uL) and triethylamine (200 uL) and stirred at ambient temperature for 18 h. Solvent was evaporated off under reduced pressure to give a dark blue residue, which was then purified by reverse-phase HPLC (acetonitrile/0.1 M TEAB gradient) to give the product 6 (λmax 677 nm).

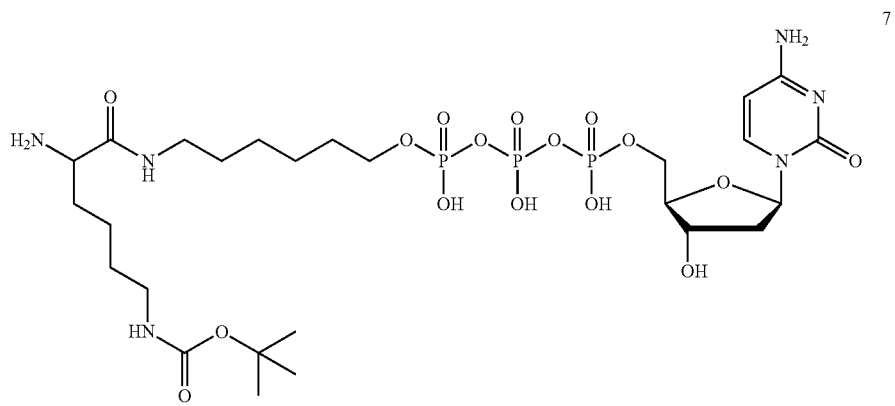 [SMILES: CC(C)(C)OC(=O)NCCCCC(N)C(=O)NCCCCCCOP(=O)(O)OP(=O)(O)OP(=O)(O)OC[C@H]1O[C@@H](n2ccc(N)nc2=O)C[C@H]1O]

Preparation of dCTP-6C-Lys(Boc)-NH$_2$ (7)

To a solution of Fmoc-D-Lys(Boc)-OPfp (4.5 mg, 7.09 umol) in DMF (400 uL) was added a solution of dCTP-6C—NH$_2$ (3 umol) in 0.1 M NaHCO$_3$, pH 8.3 aqueous buffer (200 uL) at ambient temperature for 18 h. To the solution was then added triethylamine (500 uL) and stirred for 5 h. Solvent was evaporated off under reduced pressure to give a solid, which was purified by reverse-phase HPLC (acetonitrile/0.1 M TEAB gradient) to give 2.05 umol of the desired product (68.3% yield).

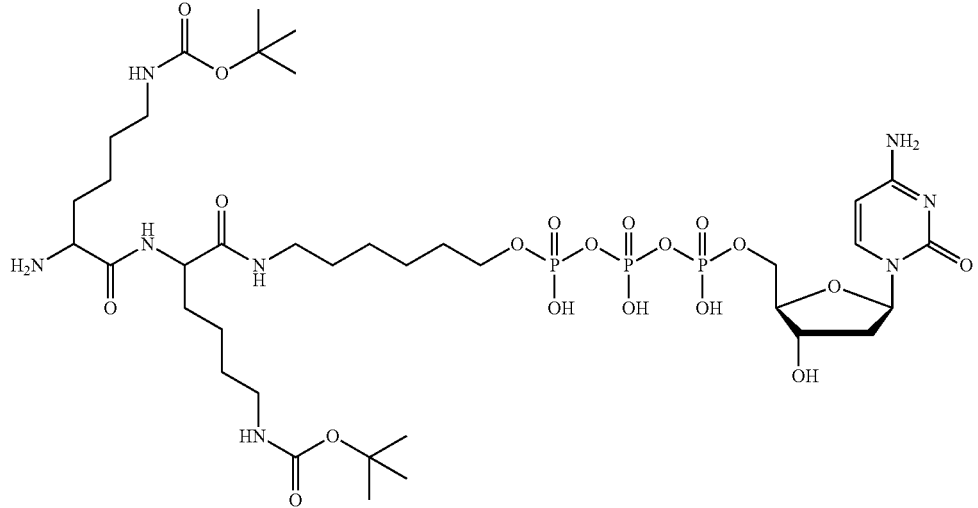

Preparation of dCTP-6C-Lys(Boc)-Lys(Boc)-NH$_2$ (8)

To a solution of Fmoc-D-Lys(Boc)-OPfp (1.65 mg, 2.60 umol) in DMF (200 uL) was added a solution of dCTP-6C-Lys(Boc)-NH$_2$ (1.30 umol) in 0.1 M NaHCO$_3$, pH 8.3 aqueous buffer (100 uL) at ambient temperature for 18 h. To the solution was then added triethylamine (400 uL) and stirred for 5 h. Solvent was evaporated off under reduced pressure to give a solid, which was purified by reverse-phase HPLC (acetonitrile/0.1 M TEAB gradient) to give 0.75 umol of the desired product (58% yield).

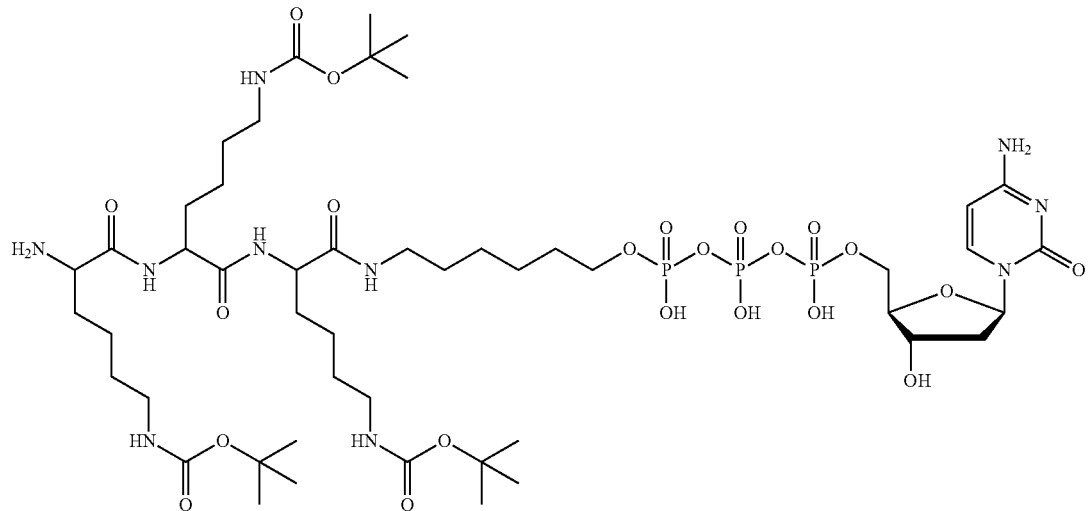

Preparation of dCTP-6C-Lys(Boc)-Lys(Boc)-Lys(Boc)-NH$_2$ (9)

To a solution of Fmoc-D-Lys(Boc)-OPfp (1.80 mg, 2.80 umol) in DMF (200 uL) was added a solution of dCTP-6C-Lys(Boc)-Lys(Boc)-NH$_2$ (0.50 umol) in 0.1 M NaHCO$_3$, pH 8.3 aqueous buffer (100 uL) at ambient temperature for 18 h. To the solution was then added triethylamine (400 uL) and stirred for 5 h. Solvent was evaporated off under reduced pressure to give a solid, which was then purified by reverse-phase HPLC (acetonitrile/0.1 M TEAB gradient) to give the desired product.

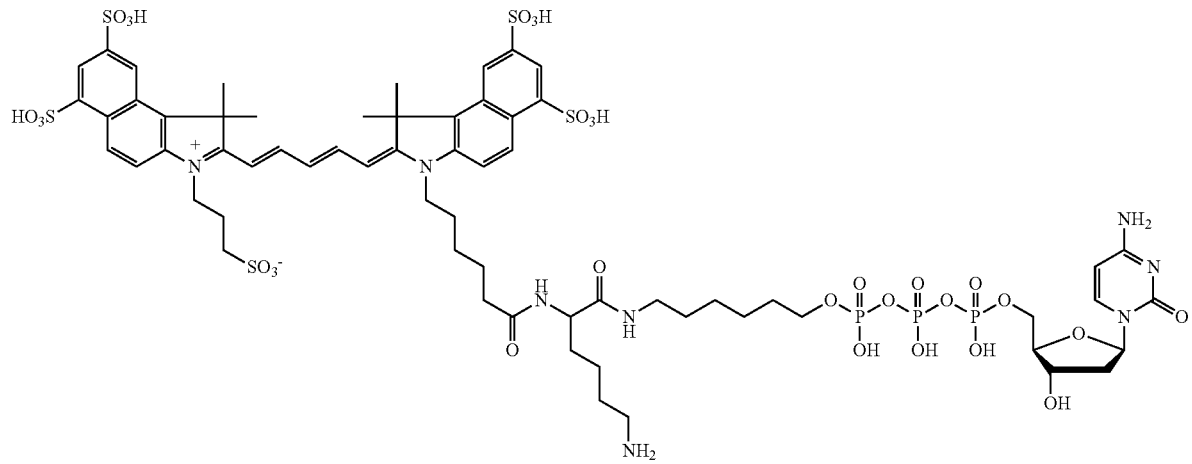

Preparation of 10

To a solution of the activated ester of dicarbocyanine dye (1 umol) in DMF (100 uL) in an Eppendorf tube was added a solution of dCTP-6C-Lys(Boc)-NH$_2$ (0.6 umol) in 0.1 M NaHCO$_3$, pH 8.3 aqueous buffer (100 uL) at 0° C. After brief vortexing the solution was let stood for 18 h in the dark at ambient temperature. The solution was then subjected to reverse-phase HPLC (acetonitrile/0.1 M TEAB gradient) purification to give the adduct, which was then treated with 3 M HCl (600 uL) at ambient temperature for 1 h. The solution was again subjected to reverse-phase HPLC (acetonitrile/0.1 M TEAB gradient) purification to give the product (0.43 umol, 71% yield).

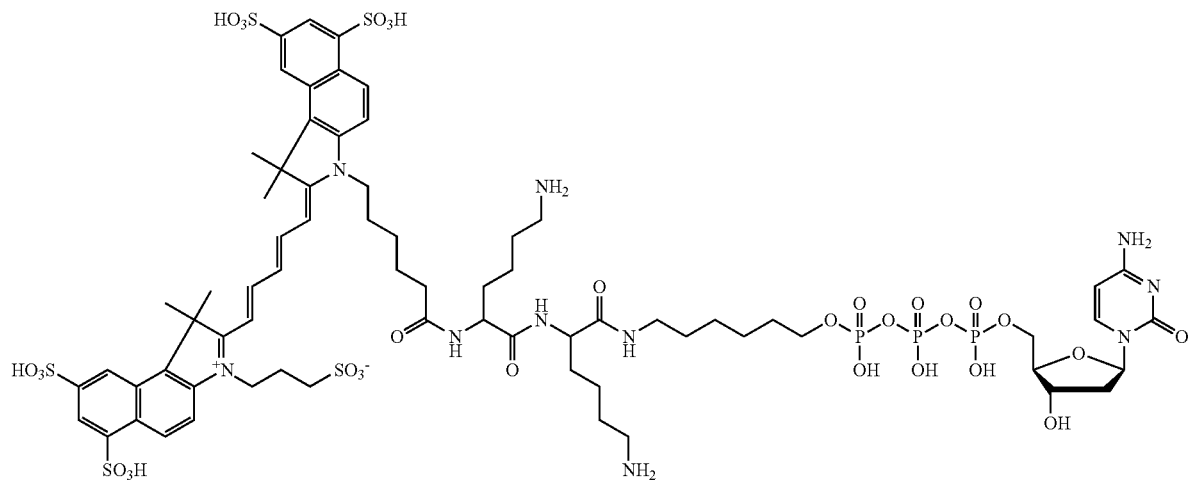

11

Preparation of 11

To a solution of the activated ester of dicarbocyanine dye GS290-103 (1 umol) in DMF (100 uL) in an Eppendorf tube was added a solution of dCTP-6C-Lys(Boc)-Lys(Boc)-NH$_2$ (0.25 umol) in 0.1 M NaHCO$_3$, pH 8.3 aqueous buffer (100 uL) at 0° C. After brief vortexing the solution was let stood for 18 h in the dark at ambient temperature. The solution was then subjected to reverse-phase HPLC (acetonitrile/0.1 M TEAB gradient) purification to give the adduct, which was then treated with 1.5 M HCl (1.2 mL) at ambient temperature for 18 h. The solution was again subjected to reverse-phase HPLC (acetonitrile/0.1 M TEAB gradient) purification to give the product (0.12 umol, 47% yield).

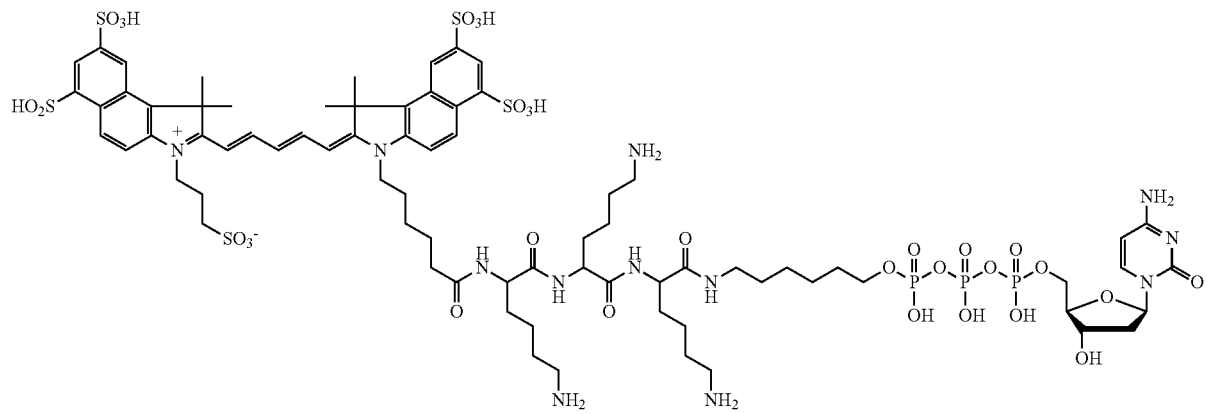

12

Preparation of 12

To a solution of the activated ester of dicarbocyanine dye (1 umol) in DMF (100 uL) in an Eppendorf tube was added a solution of dCTP-6C-Lys(Boc)-Lys(Boc)-Lys(Boc)-NH$_2$ (0.1 umol) in 0.1 M NaHCO$_3$, pH 8.3 aqueous buffer (100 uL) at 0° C. After brief vortexing the solution was let stood for 18 h in the dark at ambient temperature. The solution was then subjected to reverse-phase HPLC (acetonitrile/0.1 M TEAB gradient) purification to give the adduct, which was then treated with 3 M HCl (0.2 mL) at ambient temperature for 18 h. The solution was again subjected to reverse-phase HPLC (acetonitrile/0.1 M TEAB gradient) purification to give the product (0.02 umol, 20% yield).

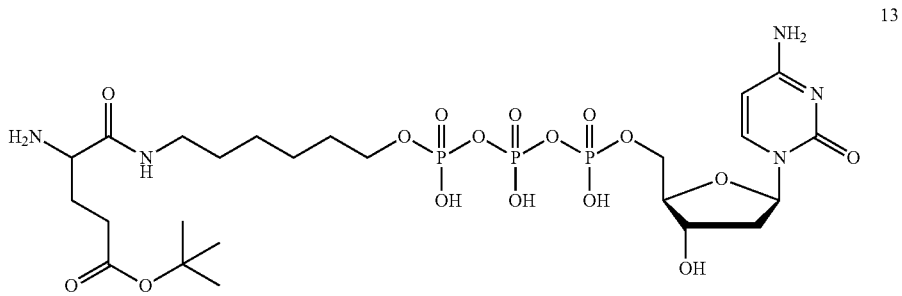 [SMILES: CC(C)(C)OC(=O)CCC(N)C(=O)NCCCCCCOP(=O)(O)OP(=O)(O)OP(=O)(O)OC[C@H]1O[C@@H](n2ccc(N)nc2=O)C[C@H]1O]

13

Preparation of dCTP-6C-Glu(Boc)-NH$_2$ (13)

To a solution of Fmoc-D-Glu(O-tBu)-OPfp (6 umol) in DMF (400 uL) was added a solution of dCTP-6C—NH$_2$ (4 umol) in 0.1 M NaHCO$_3$, pH 8.3 aqueous buffer (200 uL) at ambient temperature for 18 h. To the solution was then added triethylamine (400 uL) and stirred for 18 h. Solvent was evaporated off under reduced pressure to give a solid, which was purified by reverse-phase HPLC (acetonitrile/0.1 M TEAB gradient) to give 2.8 umol of the desired product (70% yield).

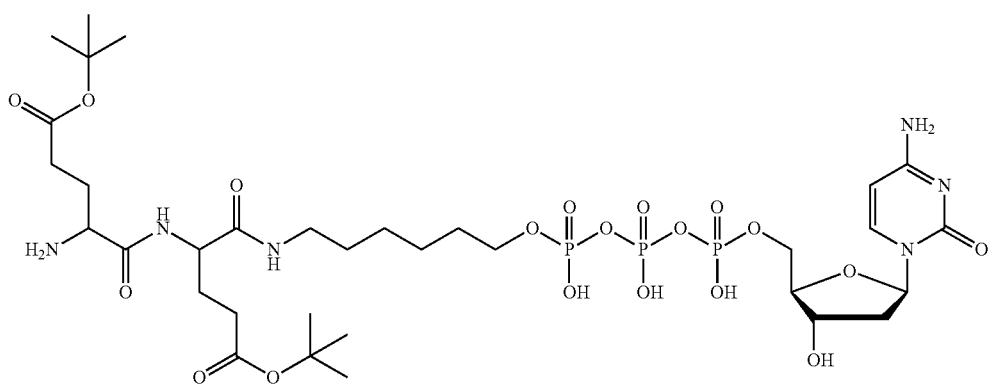

14

Preparation of dCTP-6C-Glu(O-tBu)-Glu(O-tBu)-NH₂ (14)

To a solution of Fmoc-D-Glu(O-tBu)-OPfp (6 umol) in DMF (200 uL) was added a solution of dCTP-6C-Glu(O-tBu)-NH₂ (2.4 umol) in 0.1 M NaHCO₃, pH 8.3 aqueous buffer (100 uL) at ambient temperature for 18 h. To the solution was then added triethylamine (400 uL) and stirred for 4 h. Solvent was evaporated off under reduced pressure to give a solid, which was purified by reverse-phase HPLC (acetonitrile/0.1 M TEAB gradient) to give 1.42 umol of the desired product (58% yield).

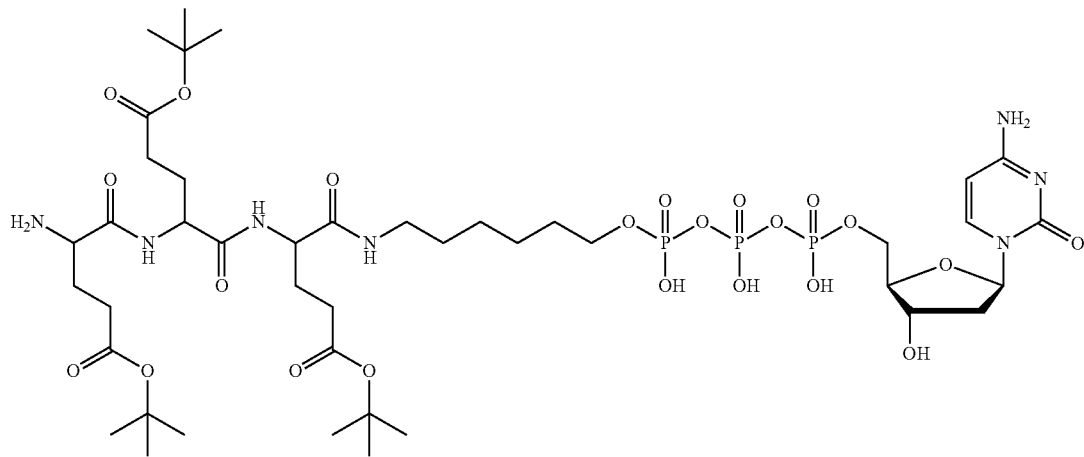

Preparation of dCTP-6C-Glu(O-tBu)-Glu(O-tBu)-Glu(O-tBu)-NH₂ (15)

To a solution of Fmoc-D-Glu(O-tBu)-OPfp (4 umol) in DMF (200 uL) was added a solution of dCTP-6C-Glu(O-tBu)-Glu(O-tBu)-NH₂ (1.0 umol) in 0.1 M NaHCO₃, pH 8.3 aqueous buffer (100 uL) at ambient temperature for 18 h. To the solution was then added triethylamine (400 uL) and stirred for 18 h. Solvent was evaporated off under reduced pressure to give a solid, which was then purified by reverse-phase HPLC (acetonitrile/0.1 M TEAB gradient) to give the desired product.

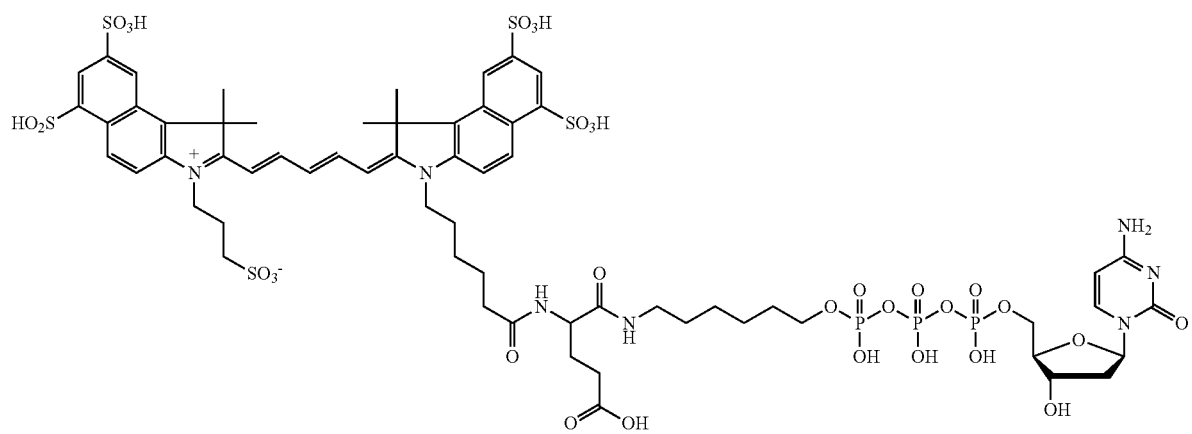

Preparation of 16

To a solution of the activated ester of dicarbocyanine dye (1 umol) in DMF (100 uL) in an Eppendorf tube was added a solution of dCTP-6C-Glu(O-tBu)-NH₂ (1.0 umol) in 0.1 M NaHCO₃, pH 8.3 aqueous buffer (100 uL) at 0° C. After brief vortexing the solution was let stood for 18 h in the dark at ambient temperature. The solution was then subjected to reverse-phase HPLC (acetonitrile/0.1 M TEAB gradient) purification to give the adduct, which was then treated with 3 M HCl (600 uL) at ambient temperature for 18 h. The solution was again subjected to reverse-phase HPLC (acetonitrile/0.1 M TEAB gradient) purification to give the product (0.14 umol, 14% yield).

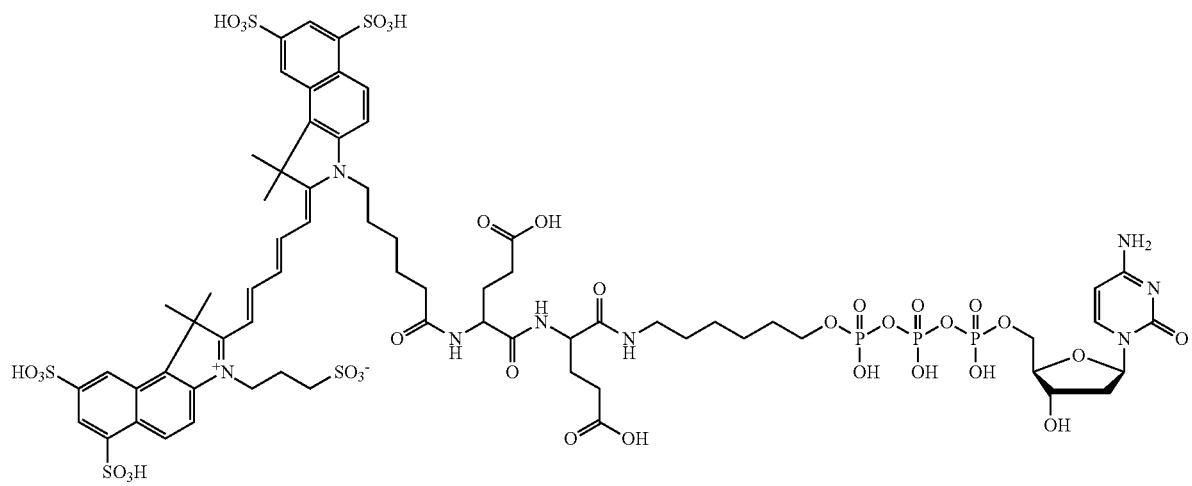

17

Preparation of 17

To a solution of the activated ester of dicarbocyanine dye (1 umol) in DMF (100 uL) in an Eppendorf tube was added a solution of dCTP-6C-Glu(O-tBu)-Glu(O-tBu)-NH₂ (0.5 umol) in 0.1 M NaHCO₃, pH 8.3 aqueous buffer (100 uL) at 0° C. After brief vortexing the solution was let stood for 18 h in the dark at ambient temperature. The solution was then subjected to reverse-phase HPLC (acetonitrile/0.1 M TEAB gradient) purification to give the adduct, which was then treated with 3 M HCl (0.4 mL) at ambient temperature for 18 h. The solution was again subjected to reverse-phase HPLC (acetonitrile/0.1 M TEAB gradient) purification to give the product (0.21 umol, 41% yield).

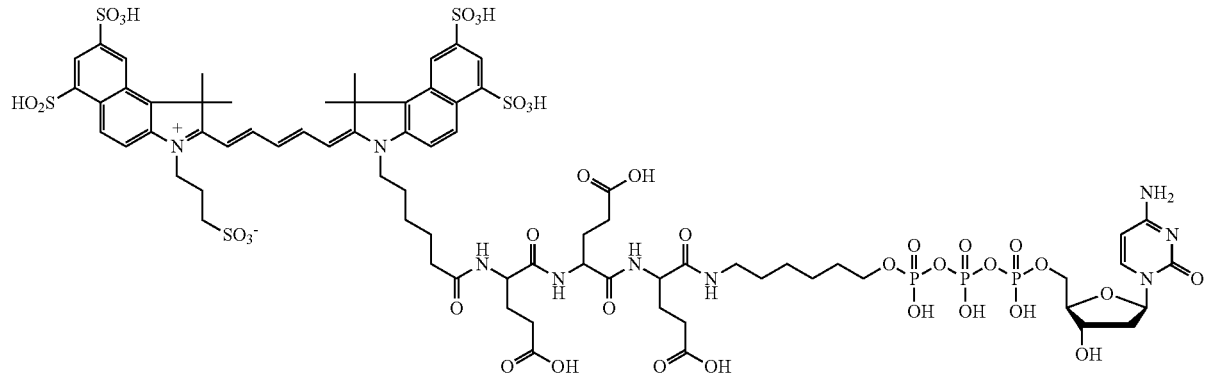

18

Preparation of 18

To a solution of the activated ester of dicarbocyanine dye (1 umol) in DMF (100 uL) in an Eppendorf tube was added a solution of dCTP-6C-Glu(O-tBu)-Glu(O-tBu)-Glu(O-tBu)-NH$_2$ (1 umol) in 0.1 M NaHCO$_3$, pH 8.3 aqueous buffer (100 uL) at 0° C. After brief vortexing the solution was let stood for 18 h in the dark at ambient temperature. The solution was then subjected to reverse-phase HPLC (acetonitrile/0.1 M TEAB gradient) purification to give the adduct, which was then treated with 3 M HCl (0.2 mL) at ambient temperature for 18 h. The solution was again subjected to reverse-phase HPLC (acetonitrile/0.1 M TEAB gradient) purification to give the product (0.18 umol, 18% yield).

The following examples set forth the preparation of sulfocystine linkers.

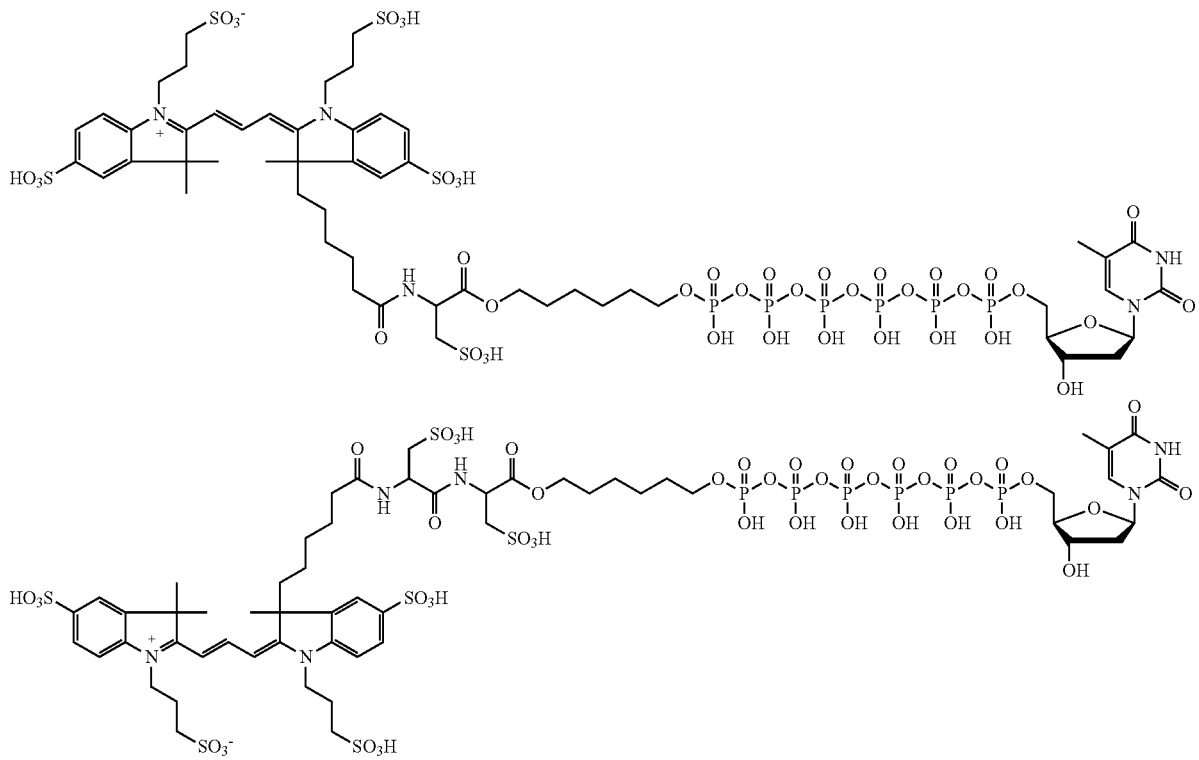

40

Scheme 5. Synthesis of the Phospholinked Analogs with Sulfocysteine Linker.

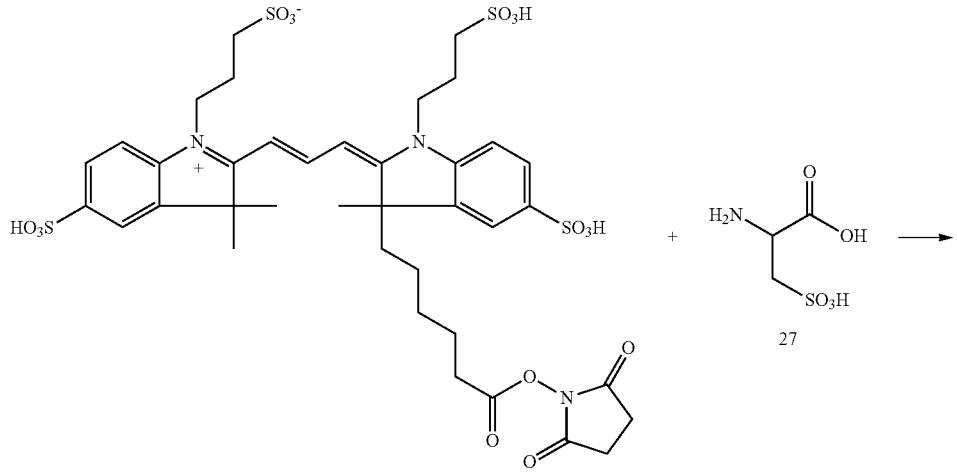

-continued
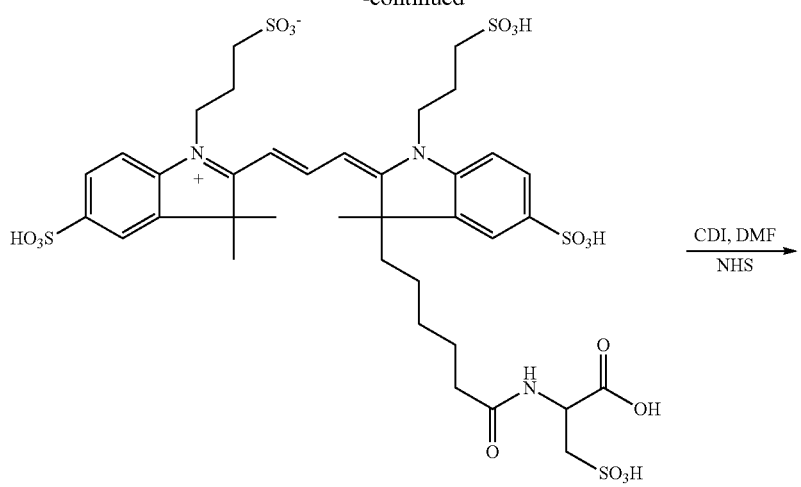
28
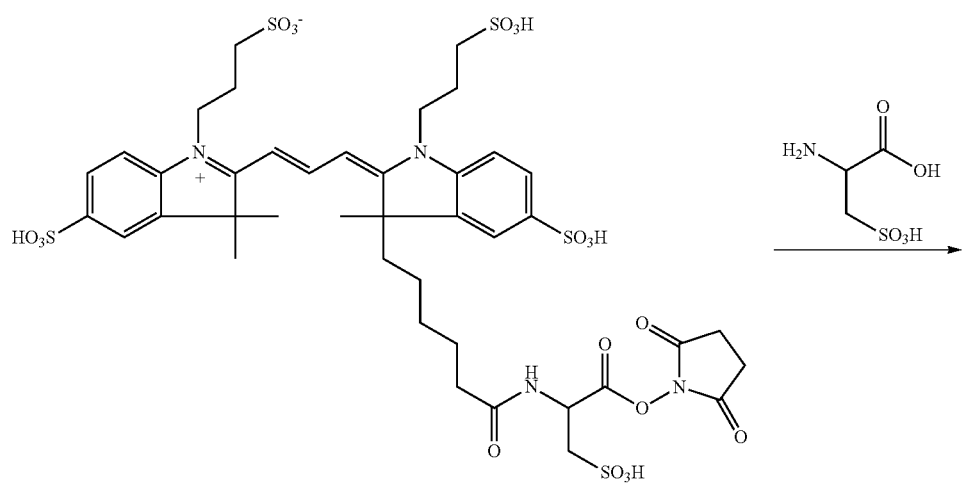
29
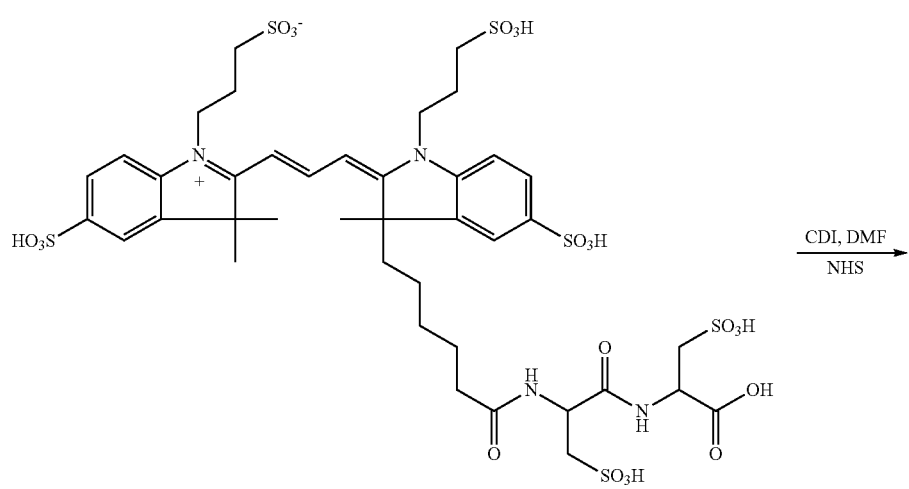
30

-continued
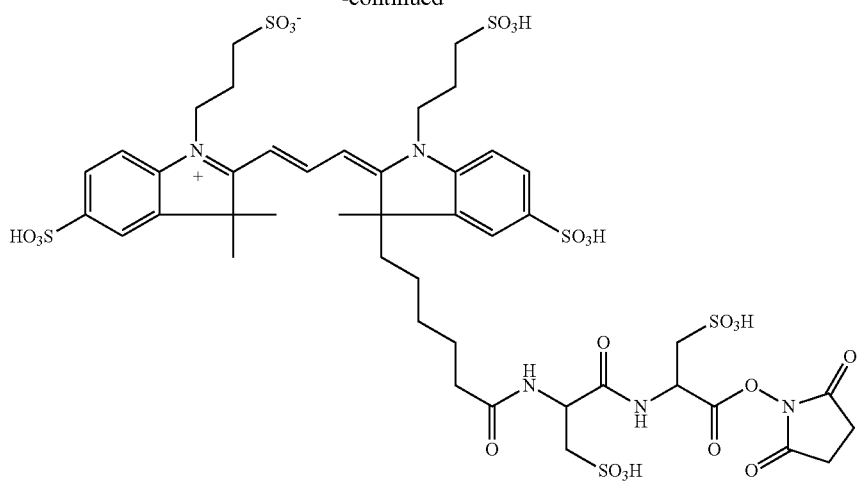
31
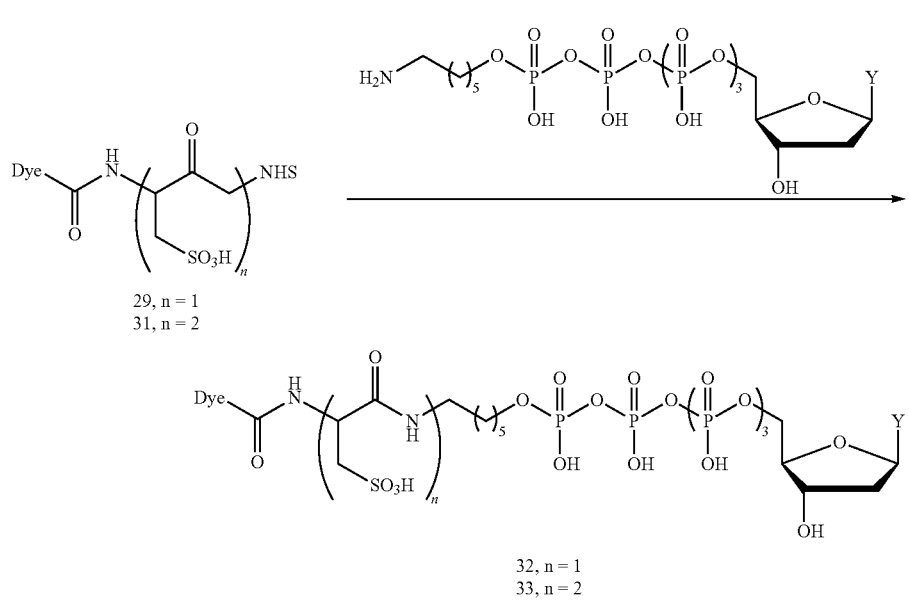
29, n = 1
31, n = 2
32, n = 1
33, n = 2
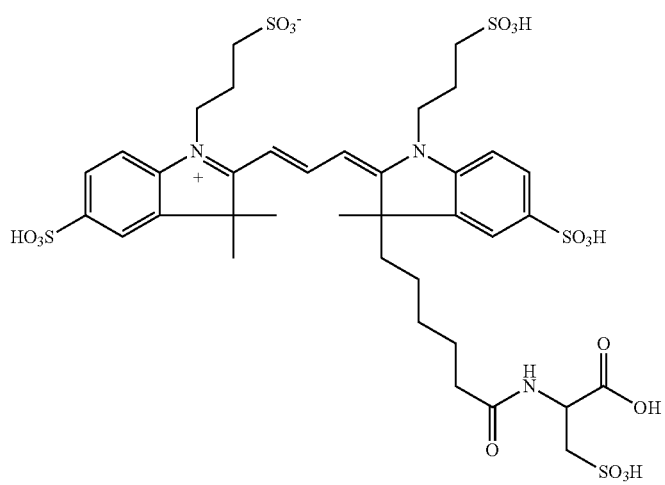
28

Preparation of Alexa555-SC (28)

To a solution of sulfocysteine (60 mg, 320 umol) in DMF (1.4 mL) was added a solution of Alexa555-NHS (16 mg, 13 umol) in DMF (1.0 mL), followed by addition of DIPEA (0.80 mL). The solution was stirred at room temperature in the dark for 18 h. After concentrating to dryness the residue was subjected to reverse-phase HPLC (acetonitrile/0.1 M TEAB gradient) purification to give the product (8.68 umol, 67% yield).

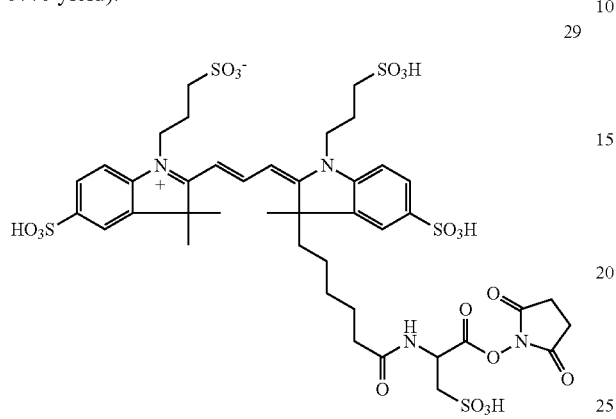

29

Preparation of Alexa555-SC-NHS (29)

To a solution of Alexa555-SC (2.0 umol) in DMF (200 uL) in an Eppendorf vial was added carbonyl diimidazole (CDI, 5 mg, excess) followed by N-hydroxysuccimide (NHS, 5 mg, excess) and vortexed. After standing in the dark for 18 h added ethyl acetate (1.3 mL) and vortexed. Centrifugation of the vial at high speed gave a pellet of product, and the solvent was decanted. The pellet was dried to give a crude product of the activated NHS ester. The product was used in the coupling reaction without further purification.

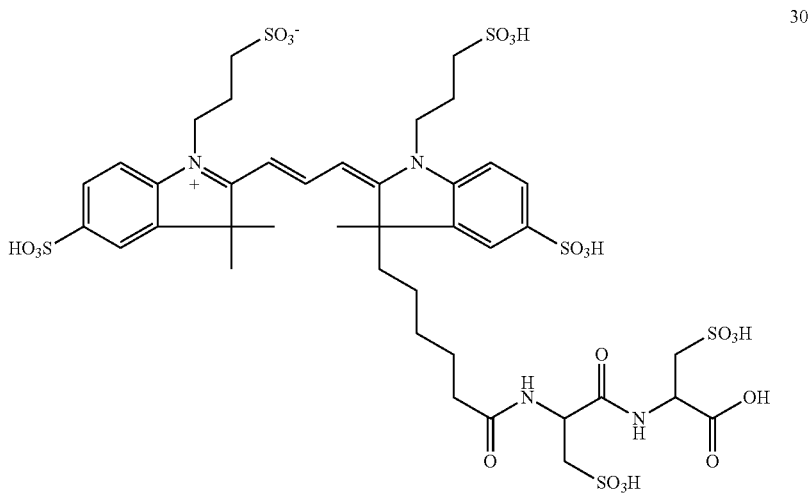

30

Preparation of Alexa555-SC-SC (30)

To a solution of sulfocysteine (10 mg, 53 umol) in 0.1 M NaHCO$_3$, pH 8.5 (200 uL) was added a solution of Alexa555-SC-NHS (2.0 umol) in DMF (200 uL). The solution was stood at room temperature in the dark for 18 h. After concentrating to dryness the residue was subjected to ion-exchange separation (1 M TEAB/0.05 TEAB) followed by reverse-phase HPLC (acetonitrile/0.1 M TEAB gradient) purification to give the product (1.38 umol, 69% yield).

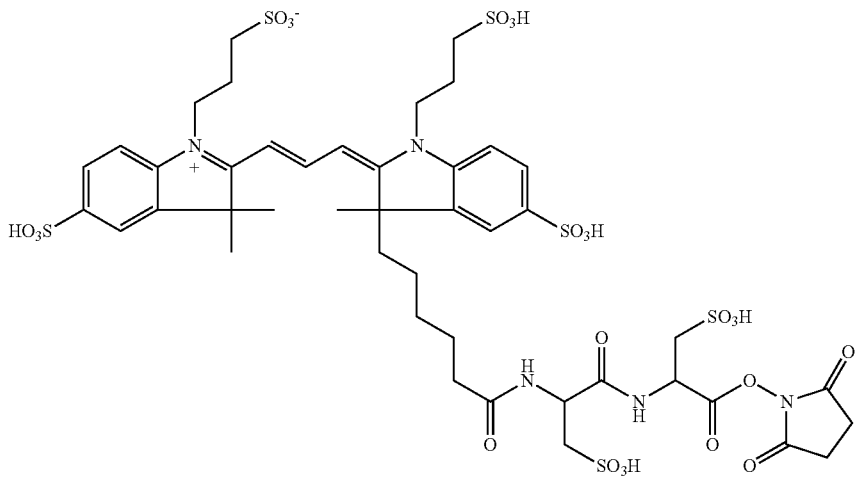

31

Preparation of Alexa555-SC-SC-NHS (31)

To a solution of Alexa555-SC-SC (1.38 umol) in DMF (100 uL) in an Eppendorf vial was added carbonyl diimidazole (CDI, 5 mg, excess) followed by N-hydroxysuccimide (NHS, 5 mg, excess) and vortexed. After standing in the dark for 18 h added ethyl acetate (1.3 mL) and vortexed. Centrifugation of the vial at high speed gave a pellet of product, and the solvent was decanted. The pellet was dried to give a crude product of the activated NHS ester. The product was used in the coupling reaction without further purification.

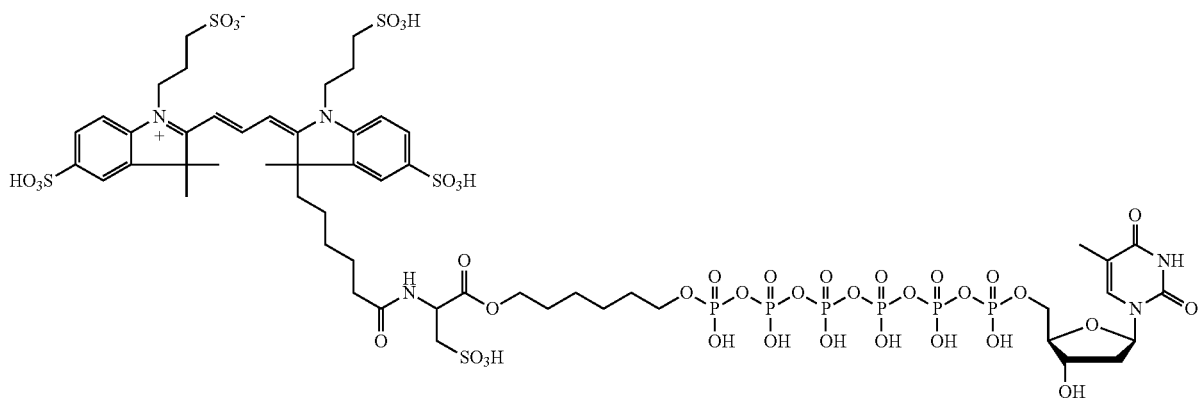

32

Preparation of Alexa555-SC-6C-dT6P (32)

To a solution of the activated ester of Alexa-SC-NHS (1 umol) in DMF (100 uL) in an Eppendorf tube was added a solution of dT6P-6C—$NH_2$ (1 umol) in 0.1 M $NaHCO_3$, pH 8.3 aqueous buffer (100 uL) at 0° C. After brief vortexing the solution was let stood for 18 h in the dark at ambient temperature. The solution was then subjected to ion-exchange separation (1 M TEAB/0.05 TEAB) followed by reverse-phase HPLC (acetonitrile/0.1 M TEAB gradient) purification to give the product (0.12 umol, 12% yield).

33

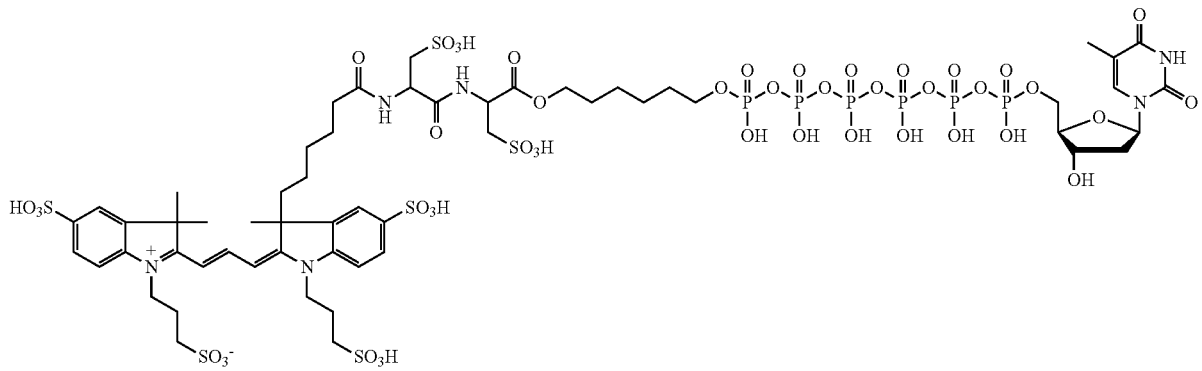

Preparation of Alexa555-SC-6C-dT6P (33) To a solution of the activated ester of Alexa-SC-SC-NHS (1.38 umol) in DMF (100 uL) in an Eppendorf tube was added a solution of dT6P-6C—NH$_2$ (1.5 umol) in 0.1 M NaHCO$_3$, pH 8.3 aqueous buffer (100 uL) at 0° C. After brief vortexing the solution was let stood for 18 h in the dark at ambient temperature. The solution was then subjected to ion-exchange separation (1 M TEAB/0.05 TEAB) followed by reverse-phase HPLC (acetonitrile/0.1 M TEAB gradient) purification to give the product (0.33 umol, 24% yield).

While this invention has been disclosed with reference to specific embodiments, it is apparent that other embodiments and variations of this invention may be devised by others skilled in the art without departing from the true spirit and scope of the invention.

All patents, patent applications, and other publications cited in this application are incorporated by reference in the entirety.

What is claimed is:

1. A fluorescent dye having the formula:

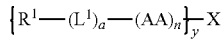

wherein
R$^1$ is a fluorescent dye moiety;
(AA)$_n$ is an amino acid linker;
n is selected from the integers 1, 2, 3, 4, 5, 6, 7, 8, 9, 10, 11 and 12, and when n is two or greater, each n amino acid is independently selected;
X is a polyvalent moiety, comprising a moiety having the structure:

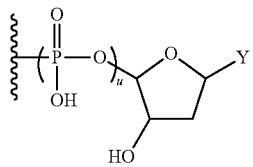

wherein
Y is a nucleobase; and
u is selected from the integers 1, 2, 3, 4, 5, 6, 7 and 8;
y is selected from the integers 1, 2, 3, 4, 5, 6, 7 and 8, such that when y is 2 or greater, X is a polyvalent moiety;
L$^1$ is selected from bonds and adaptors; and
a is selected from the integers 0 and 1.

2. The fluorescent dye according to claim 1 wherein said polyvalent moiety comprises bonded thereto a member selected from a second fluorescent dye moiety, a nucleic acid and a combination thereof.

3. The fluorescent dye according to claim 2, wherein said first fluorescent dye moiety and said second fluorescent dye moiety form a FRET pair.

4. The fluorescent dye of claim 1, wherein said amino acid linker includes amino acids selected from hydrophobic amino acids, cationic amino acids, and a combination thereof.

5. The fluorescent dye of claim 4, wherein said amino acid linker further comprises an anionic amino acid.

6. The fluorescent dye of claim 1, wherein n is 1, 2, 3, 4, 5, or 6.

7. The fluorescent dye of claim 1, wherein the amino acids forming (AA)$_n$ are the same amino acid or a different amino acid.

8. The fluorescent dye of claim 1, wherein said amino acid linker is other than Pro, Pro$_2$, Pro$_3$, Pro$_4$, Pro$_5$ or Pro$_6$.

9. The fluorescent dye of claim 1, wherein said amino acid linker is other than Lys, Lys$_4$, Lys$_5$ or Lys$_6$.

10. The fluorescent dye of claim 5, wherein said anionic amino acid is a member selected from, sulfocysteine, glutamic acid, and O-phosphoserine.

11. The fluorescent dye of claim 1, wherein L$^1$ comprises an adaptor selected from an alkyl amine and a nitrogen-containing heterocyclic moiety.

12. The fluorescent dye of claim 11, wherein said alkyl amine is:

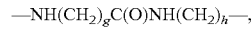

wherein
g and h are independently selected from the integers 0, 1, 2, 3, 4, 5, 6, 7, 8, 9, 10 or higher.

13. The fluorescent dye of claim 1, wherein each of said n amino acids is the same amino acid.

14. The fluorescent dye of claim 1, wherein said fluorescent dye moiety is a cyanine dye.

15. The fluorescent dye of claim 14, wherein said cyanine is selected from Cy3 and Cy5 cyanine dyes.

16. The fluorescent dye of claim 1, wherein said polyvalent moiety is a residue of a member selected from triazine, perylene, piperidine, phenylalanine, diaminopropanoic acid, aspartic acid, lysine, glutamic acid, serine, aminoadipic acid, 3,5-dihydroxybenzoic acid, 2-amino-4-hydroxy-butyric acid, 4-(1-amino-1-carboxyethyl)-benzoic acid, piperazine-2-carboxylic acid, 4-[4,6-bis-(piperidin-4-ylamino)-[1,3,5]triazin-2-ylamino]-cyclohexanecarboxylic acid and 3-amino-3[4-(3-amino-prop-1-ynyl)-phenyl]-propionic acid.

17. The fluorescent dye of claim 1, wherein said fluorescent dye binds to a DNA polymerase with a binding constant greater than an otherwise identical fluorescent dye in which $(AA)_n$ is absent.

18. The fluorescent dye of claim 1 wherein said amino acid comprises a side chain comprising a moiety having the formula:

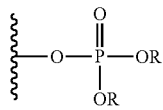

in which each R is independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl.

19. A method of monitoring an enzyme reaction, said method comprising:

(a) forming a reaction mixture by contacting said enzyme with a fluorescent dye according to claim 1, wherein said dye is a substrate for said enzyme under conditions sufficient for said enzyme and said dye to react; and (b) monitoring fluorescence of said reaction mixture.

20. The method according to claim 19, wherein said enzyme is a DNA polymerase and said dye comprises a nucleic acid moiety which is said substrate for said enzyme.

21. The method according to claim 19 wherein said enzyme reaction is template directed DNA synthesis.

22. The method according to claim 21, wherein said reaction is a component of a single molecule DNA sequencing analysis.

* * * * *